US012715888B2

(12) United States Patent
Choung et al.

(10) Patent No.: US 12,715,888 B2
(45) Date of Patent: Aug. 25, 2026

(54) ORGANOMETALLIC COMPOUND AND ORGANIC LIGHT-EMITTING DIODE INCLUDING THE SAME

(71) Applicants: LG DISPLAY CO., LTD., Seoul (KR); ROHM AND HAAS ELECTRONIC MATERIALS KOREA LTD., Cheonan-si (KR)

(72) Inventors: Kusun Choung, Seoul (KR); Hansol Park, Goyang-si (KR); Yoojeong Jeong, Seoul (KR); Kyoung-Jin Park, Hwaseong-si (KR); Hyun Kim, Hwaseong-si (KR); Jin Ri Hong, Hwaseong-si (KR); Yeon Gun Lee, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 939 days.

(21) Appl. No.: 17/872,763

(22) Filed: Jul. 25, 2022

(65) Prior Publication Data

US 2023/0110454 A1 Apr. 13, 2023

(30) Foreign Application Priority Data

Jul. 29, 2021 (KR) ........................ 10-2021-0099890

(51) Int. Cl.
*C07F 15/00* (2006.01)
*C07D 209/82* (2006.01)
(Continued)

(52) U.S. Cl.
CPC ........ *C07F 15/0033* (2013.01); *C07D 209/82* (2013.01); *H10K 50/131* (2023.02);
(Continued)

(58) Field of Classification Search
CPC ............. H10K 85/657; H10K 85/6572; H10K 85/6574; H10K 85/6576; H10K 85/342; H10K 50/12
See application file for complete search history.

(56) References Cited

U.S. PATENT DOCUMENTS 9,905,784 B2 2/2018 Xia et al.
10,033,000 B2 7/2018 Xia et al.
(Continued)

FOREIGN PATENT DOCUMENTS

CN 104650151 A 5/2015
CN 108530487 A * 9/2018 ............. C09K 11/06
(Continued)

OTHER PUBLICATIONS

Office Action issued on Oct. 29, 2024 in Chinese Patent Application No. 202210910303.1 with English tranlsation.
(Continued)

*Primary Examiner* — Michael M Dollinger
(74) *Attorney, Agent, or Firm* — Morgan, Lewis & Bockius LLP

(57) ABSTRACT

Disclosed is an organometallic compound represented by a following Chemical Formula 1. The organometallic compound acts as a dopant of a light-emitting layer of an organic light-emitting diode. Thus, operation voltage of the diode is lowered, and luminous efficiency and lifespan thereof are improved:

[Chemical Formula 1]

$$Ir(L_A)_m(L_B)_n$$

where in the Chemical Formula 1, $L_A$ represents a main ligand having an imidazole or benzimidazole group,
(Continued)

and includes one selected from a group consisting of following Chemical Formula 2-1, Chemical Formula 2-2, Chemical Formula 2-3, Chemical Formula 2-4, Chemical Formula 2-5, Chemical Formula 2-6, Chemical Formula 2-7 and Chemical Formula 2-8, $L_B$ denotes an ancillary ligand represented by a following Chemical Formula 3, each of m and n denotes a number of the ligands bound to Ir (iridium), and m is 1, 2 or 3, and n is 0, 1 or 2, and a sum of m and n is 3.

8 Claims, 3 Drawing Sheets

(51) Int. Cl.
*H10K 50/13* (2023.01)
*H10K 85/30* (2023.01)
*H10K 85/60* (2023.01)

(52) U.S. Cl.
CPC ....... *H10K 85/342* (2023.02); *H10K 85/6572* (2023.02); *C07B 2200/05* (2013.01)

(56) References Cited

U.S. PATENT DOCUMENTS 10,418,569 B2 9/2019 Kwong et al.
10,522,768 B2 12/2019 Egen et al.
2005/0260448 A1* 11/2005 Lin ........................ H05B 33/14 428/917
2013/0306940 A1 11/2013 Zeng
2013/0328037 A1 12/2013 Oshiyama
2014/0309428 A1 10/2014 Egen et al.
2015/0090981 A1 4/2015 Xia et al.
2015/0137095 A1 5/2015 Xia et al.
2016/0190483 A1 6/2016 Kim
2017/0084849 A1* 3/2017 Tsai .................... C07F 15/0033
2020/0136064 A1 4/2020 Egen et al.

FOREIGN PATENT DOCUMENTS

CN 108586539 A 9/2018
EP 2677561 A1 12/2013
EP 2874192 A2 * 5/2015 ............. C09K 11/06
KR 10-2007-0090953 A 9/2007
KR 10-2013-0131230 A 12/2013
KR 10-2015-0056467 A 5/2015
KR 10-2016-0081098 A 7/2016
KR 10-2016-0091832 A 8/2016
KR 20200145012 A * 12/2020 ............. C09K 11/06
WO WO-2015071473 A1 * 5/2015 ........... H10K 85/624

OTHER PUBLICATIONS

European Search Report issued in corresponding European patent application 22187159.3 dated Dec. 5, 2022.

* cited by examiner

ORGANOMETALLIC COMPOUND AND ORGANIC LIGHT-EMITTING DIODE INCLUDING THE SAME

CROSS-REFERENCE TO RELATED APPLICATION

This application claims priority from Korean Patent Application No. 10-2021-0099890 filed on Jul. 29, 2021, in the Korean Intellectual Property Office, and all the benefits accruing therefrom under 35 U.S.C. 119, the contents of which in its entirety are herein incorporated by reference.

BACKGROUND

Technical Field

The present disclosure relates to an organometallic compound, and more particularly, to an organometallic compound having phosphorescent properties and an organic light-emitting diode including the same.

Discussion of the Related Art

As a display device is applied to various fields, interest with the display device is increasing. One of the display devices is an organic light-emitting display device including an organic light-emitting diode (OLED) which is rapidly developing.

In the organic light-emitting diode, when electric charges are injected into a light-emitting layer formed between a positive electrode and a negative electrode, an electron and a hole are recombined with each other in the light-emitting layer to form an exciton and thus energy of the exciton is converted to light. Thus, the organic light-emitting diode emits the light. Compared to conventional display devices, the organic light-emitting diode may operate at a low voltage, consume relatively little power, render excellent colors, and may be used in a variety of ways because a flexible substrate may be applied thereto. Further, a size of the organic light-emitting diode may be freely adjustable.

SUMMARY

The organic light-emitting diode (OLED) has superior viewing angle and contrast ratio compared to a liquid crystal display (LCD), and is lightweight and is ultra-thin because the OLED does not require a backlight. The organic light-emitting diode includes a plurality of organic layers between a negative electrode (electron injection electrode; cathode) and a positive electrode (hole injection electrode; anode). The plurality of organic layers may include a hole injection layer, a hole transport layer, a hole transport auxiliary layer, an electron blocking layer, and a light-emitting layer, an electron transport layer, etc.

In this organic light-emitting diode structure, when a voltage is applied across the two electrodes, electrons and holes are injected from the negative and positive electrodes, respectively, into the light-emitting layer and thus excitons are generated in the light-emitting layer and then fall to a ground state to emit light.

Organic materials used in the organic light-emitting diode may be largely classified into light-emitting materials and charge-transporting materials. The light-emitting material is an important factor determining luminous efficiency of the organic light-emitting diode. The luminescent material must have high quantum efficiency, excellent electron and hole mobility, and must exist uniformly and stably in the light-emitting layer. The light-emitting materials may be classified into light-emitting materials emitting light of blue, red, and green colors based on colors of the light. A color-generating material may include a host and dopants to increase the color purity and luminous efficiency through energy transfer.

In recent years, there is a trend to use phosphorescent materials rather than fluorescent materials for the light-emitting layer. When the fluorescent material is used, singlets as about 25% of excitons generated in the light-emitting layer are used to emit light, while most of triplets as 75% of the excitons generated in the light-emitting layer are dissipated as heat. However, when the phosphorescent material is used, singlets and triplets are used to emit light.

In the related art, an organometallic compound is used as the phosphorescent material used in the organic light-emitting diode. Research and development of the phosphorescent material to solve low efficiency and lifetime problems are continuously required.

Accordingly, embodiments of the present disclosure are directed to an organometallic compound and an organic light-emitting diode including the same that substantially obviate one or more of the problems due to limitations and disadvantages of the related art.

Accordingly, an aspect of the present invention is to provide an organometallic compound capable of lowering operation voltage, and improving efficiency, and lifespan, and an organic light-emitting diode including an organic light-emitting layer containing the same.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

To achieve these and other aspects of the inventive concepts, as embodied and broadly described, the present disclosure provides an organometallic compound having a novel structure represented by a following Chemical Formula 1, and an organic light-emitting diode in which a light-emitting layer contains the same as dopants thereof:

[Chemical Formula 1]

$$Ir(L_A)_m(L_B)_n$$

where in the Chemical Formula 1, $L_A$ represents a main ligand having an imidazole or benzimidazole group, and is one selected from a group consisting of following Chemical Formula 2-1, Chemical Formula 2-2, Chemical Formula 2-3, Chemical Formula 2-4, Chemical Formula 2-5, Chemical Formula 2-6, Chemical Formula 2-7 and Chemical Formula 2-8, $L_B$ denotes an ancillary ligand represented by a following Chemical Formula 3, each of m and n denotes a number of the ligands bound to Ir (iridium), and m is 1, 2 or 3, and n is 0, 1 or 2, and a sum of m and n is 3,

[Chemical Formula 2-1]
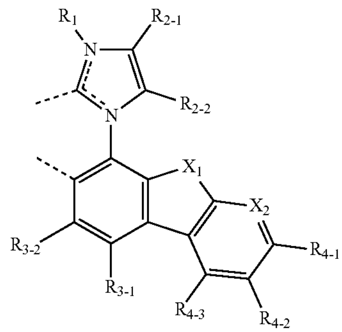
[Chemical Formula 2-2]
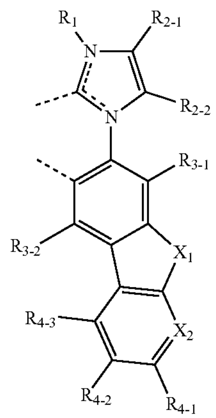
[Chemical Formula 2-3]
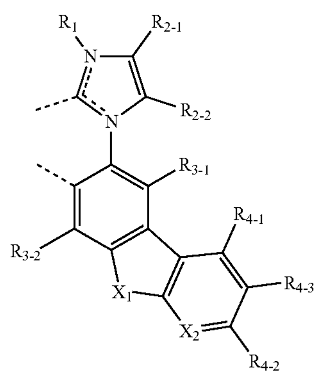
[Chemical Formula 2-4]
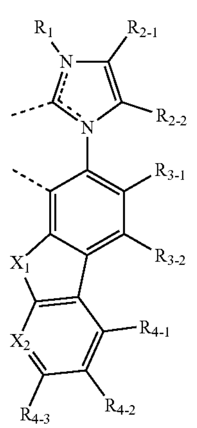
-continued
[Chemical Formula 2-5]
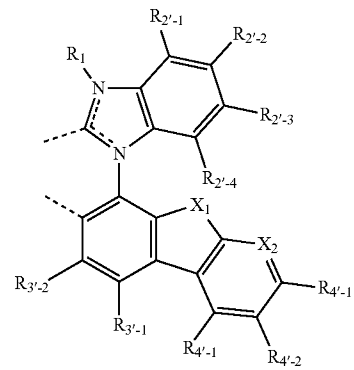
[Chemical Formula 2-6]
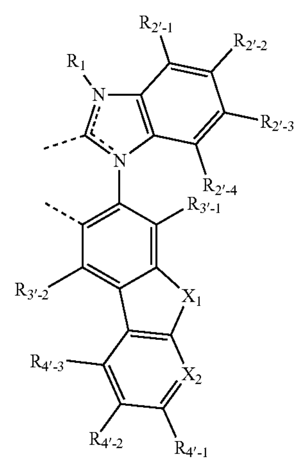
[Chemical Formula 2-7]
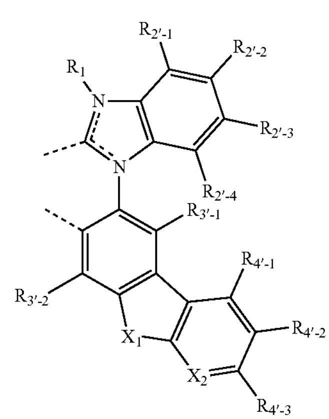

-continued

[Chemical Formula 2-8]

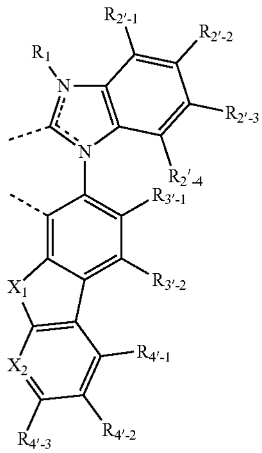

[Chemical Formula 3]

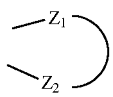

wherein in each of the Chemical Formulas 2-1 to 2-8, each of $X_1$ and $X_2$ independently represents one selected from a group consisting of oxygen, sulfur, $C(R)_2$ and NR, each of R, $R_1$, $R_{2-1}$, $R_{2-2}$, $R_{2'-1}$, $R_{2'-2}$, $R_{2'-3}$, $R_{2'-4}$, $R_{3-1}$, $R_{3-2}$, $R_{3'-1}$, $R_{3'-2}$, $R_{4-1}$, $R_{4-2}$, $R_{4-3}$, $R_{4'-1}$, $R_{4'-2}$ and $R_{4'-3}$ independently represents one selected from a group consisting of hydrogen, deuterium, halide, deuterated or undeuterated alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, and phosphino, in each of the Chemical Formulas 2-1 to 2-8, two functional groups $R_{2-1}$ and $R_{2-2}$ adjacent to each other may be combined with each other to form a ring structure, two functional groups adjacent to each other among $R_{2'}$-1, $R_{2'-2}$, $R_{2'-3}$ and $R_{2'-4}$ may be combine with each other to form a ring structure, two functional groups $R_{3-1}$ and $R_{3-2}$ adjacent to each other may be combined with each other to form a ring structure, two functional groups $R_{3'-1}$ and $R_{3'-2}$ adjacent to each other may be combined with each other to form a ring structure, two functional groups adjacent to each other among $R_{4-1}$, $R_{4-2}$ and $R_{4-3}$ may be combined with each other to form a ring structure, and two functional groups adjacent to each other among $R_{4'4}$, $R_{4'-2}$ and $R_{4'-3}$ may be combined with each other to form a ring structure, wherein the ancillary ligand represented by the Chemical Formula 3 is a bidentate ligand, and the ancillary ligand is one represented by a following Chemical Formula 4 or a following Chemical Formula 5:

[Chemical Formula 4]

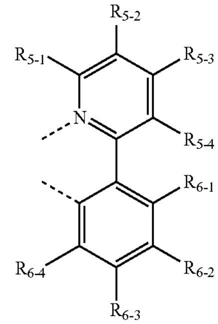

[Chemical Formula 5]

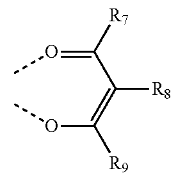

wherein in the Chemical Formula 4, each of $R_{5-1}$, $R_{5-2}$, $R_{5-3}$, $R_{5-4}$, $R_{6-1}$, $R_{6-2}$, $R_{6-3}$ and $R_{6-4}$ independently represents one selected from a group consisting of hydrogen, deuterium, a C1 to C5 linear alkyl group, and C1 to C5 branched alkyl group, wherein the C1 to C5 linear alkyl group or the C1 to C5 branched alkyl group may be substituted with at least one selected from deuterium and a halogen element, two functional groups adjacent to each other among $R_{5-1}$, $R_{5-2}$, $R_{5-3}$ and $R_{5-4}$ may be combined with each other to form a ring structure, and two functional groups adjacent to each other among $R_{6-1}$, $R_{6-2}$, $R_{6-3}$ and $R_{6-4}$ may be combined with each other to form a ring structure, wherein in the Chemical Formula 5, each of $R_7$, $R_8$ and $R_9$ independently represents one selected from a group consisting of hydrogen, deuterium, C1 to C5 linear alkyl group and C1 to C5 branched alkyl group, wherein the C1 to C5 linear alkyl group or the C1 to C5 branched alkyl group may be substituted with at least one selected from deuterium and a halogen element, and two functional groups adjacent to each other among $R_7$, $R_8$ and $R_9$ may combine with each other to form a ring structure.

The organometallic compound according to the present disclosure may be used as the dopant of the light-emitting layer of the organic light-emitting diode, such that the operation voltage of the organic light-emitting diode may be lowered and the efficiency and lifespan characteristics of the organic light-emitting diode may be improved.

It is to be understood that both the foregoing general description and the following detailed description are exemplary and explanatory and are intended to provide further explanation of the inventive concepts as claimed.

BRIEF DESCRIPTION OF DRAWINGS

The accompanying drawings, which are included to provide a further understanding of the disclosure and are incorporated in and constitute a part of this application, illustrate embodiments of the disclosure and together with the description serve to explain various principles.

DETAILED DESCRIPTION

Figure 1:
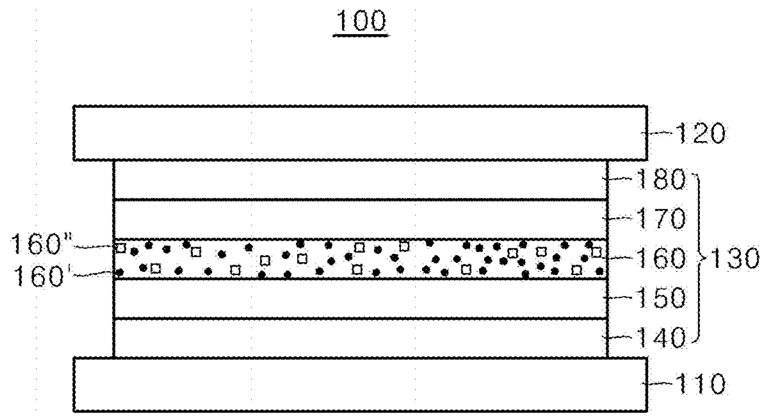
FIG. 1 is a cross-sectional view schematically showing an organic light-emitting diode in which a light-emitting layer contains an organometallic compound according to an illustrative embodiment of the present disclosure.

Advantages and features of the present disclosure, and a method of achieving the advantages and features will become apparent with reference to embodiments described later in detail together with the accompanying drawings. However, the present disclosure is not limited to the embodiments as disclosed below, but may be implemented in various different forms. Thus, these embodiments are set forth only to make the present disclosure complete, and to completely inform the scope of the present disclosure to those of ordinary skill in the technical field to which the present disclosure belongs, and the present disclosure is only defined by the scope of the claims.

A shape, a size, a ratio, an angle, a number, etc. disclosed in the drawings for describing the embodiments of the present disclosure are illustrative, and the present disclosure is not limited thereto. The same reference numerals refer to the same elements herein. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The terminology used herein is directed to the purpose of describing particular embodiments only and is not intended to be limiting of the present disclosure. As used herein, the singular constitutes "a" and "an" are intended to include the plural constitutes as well, unless the context clearly indicates otherwise. It will be further understood that the terms "comprise", "comprising", "include", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list. In interpretation of numerical values, an error or tolerance therein may occur even when there is no explicit description thereof.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

In descriptions of temporal relationships, for example, temporal precedent relationships between two events such as "after", "subsequent to", "before", etc., another event may occur therebetween unless "directly after", "directly subsequent" or "directly before" is not indicated.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

The features of the various embodiments of the present disclosure may be partially or entirely combined with each other, and may be technically associated with each other or operate with each other. The embodiments may be implemented independently of each other and may be implemented together in an association relationship.

In interpreting a numerical value, the value is interpreted as including an error range unless there is no separate explicit description thereof.

It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

The features of the various embodiments of the present disclosure may be partially or entirely combined with each other, and may be technically associated with each other or operate with each other. The embodiments may be implemented independently of each other and may be implemented together in an association relationship.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

An organometallic compound according to some embodiments of the present disclosure may be represented by a following Chemical Formula 1. When the organometallic compound is used as a dopant of a light emission layer of an organic light-emitting diode, luminous efficiency and lifetime of the diode may be improved:

[Chemical Formula 1]

$Ir(L_A)_m(L_B)_n$ where in the Chemical Formula 1, $L_A$ represents a main ligand having an imidazole or benzimidazole group, and is one selected from a group consisting of following Chemical Formula 2-1, Chemical Formula 2-2, Chemical Formula 2-3, Chemical Formula 2-4, Chemical Formula 2-5, Chemical Formula 2-6, Chemical Formula 2-7 and Chemical Formula 2-8, $L_B$ denotes an ancillary ligand represented by a following Chemical Formula 3, each of m and n denotes a number of the ligands bound to Ir (iridium), and m is 1, 2 or 3, and n is 0, 1 or 2, and a sum of m and n is 3,

[Chemical Formula 2-1]

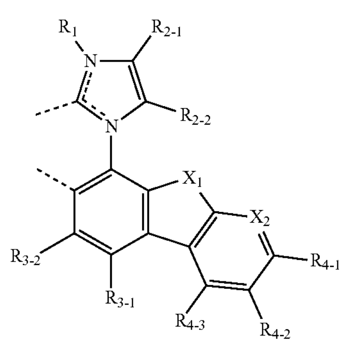

-continued

[Chemical Formula 2-2]

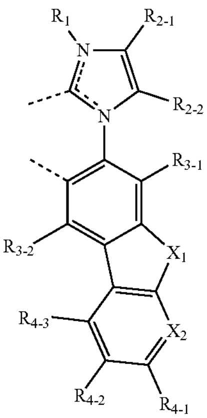

[Chemical Formula 2-3]

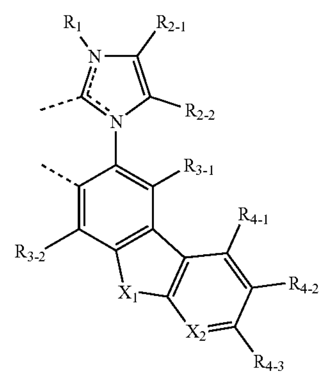

[Chemical Formula 2-4]

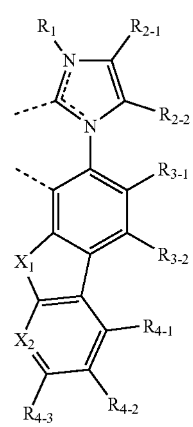

-continued

[Chemical Formula 2-5]

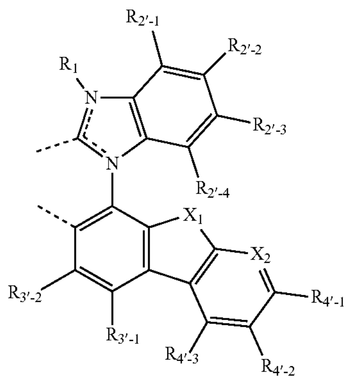

[Chemical Formula 2-6]

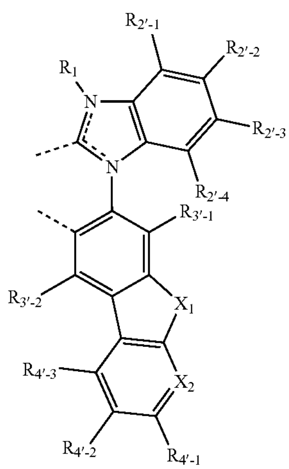

[Chemical Formula 2-7]

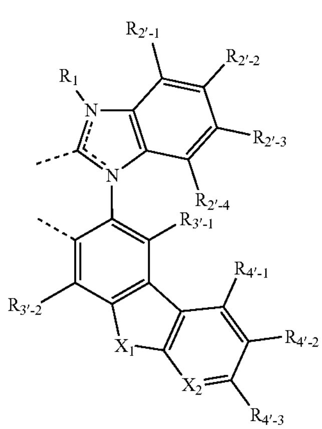

-continued

[Chemical Formula 2-8]

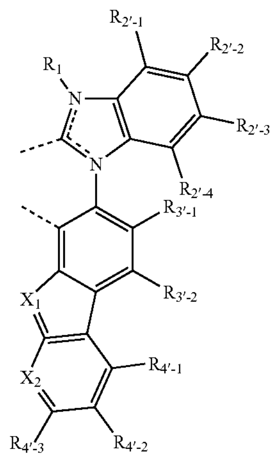

[Chemical Formula 3]

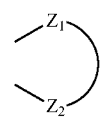

wherein in each of the Chemical Formulas 2-1 to 2-8, each of $X_1$ and $X_2$ independently represents one selected from a group consisting of oxygen, sulfur, $C(R)_2$ and NR, each of R, $R_1$, $R_{2-1}$, $R_{2-2}$, $R_{2'-1}$, $R_{2'-2}$, $R_{2'-3}$, $R_{2'-4}$, $R_{3-1}$, $R_{3-2}$, $R_{3'-1}$, $R_{3'-2}$, $R_{4-1}$, $R_{4-2}$, $R_{4-3}$, $R_{4'-1}$, $R_{4'-2}$ and $R_{4'-3}$ independently represents one selected from a group consisting of hydrogen, deuterium, halide, deuterated or undeuterated alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, and phosphino, in each of the Chemical Formulas 2-1 to 2-8, two functional groups $R_{2-1}$ and $R_{2-2}$ adjacent to each other may be combined with each other to form a ring structure, two functional groups adjacent to each other among $R_{2'-1}$, $R_{2'-2}$, $R_{2'-3}$ and $R_{2'-4}$ may be combined with each other to form a ring structure, two functional groups $R_{3-1}$ and $R_{3-2}$ adjacent to each other may be combined with each other to form a ring structure, two functional groups $R_{3'-1}$ and $R_{3'-2}$ adjacent to each other may be combined with each other to form a ring structure, two functional groups adjacent to each other among $R_{4-1}$, $R_{4-2}$ and $R_{4-3}$ may be combined with each other to form a ring structure, and two functional groups adjacent to each other among $R_{4'-1}$, $R_{4'-2}$ and $R_{4'-3}$ may be combined with each other to form a ring structure, wherein the ancillary ligand represented by the Chemical Formula 3 is a bidentate ligand, and the bidentate ligand is represented by a following Chemical Formula 4 or a following Chemical Formula 5:

[Chemical Formula 4]

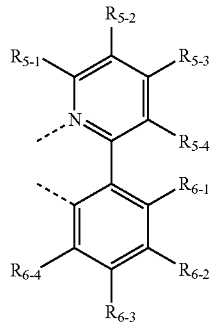

[Chemical Formula 5]

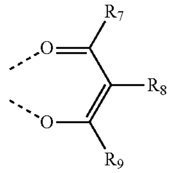

wherein in the Chemical Formula 4, each of $R_{5-1}$, $R_{5-2}$, $R_{5-3}$, $R_{5-4}$, $R_{6-1}$, $R_{6-2}$, $R_{6-3}$ and $R_{64}$ independently represents one selected from a group consisting of hydrogen, deuterium, a C1 to C5 linear alkyl group, and C1 to C5 branched alkyl group, wherein the C1 to C5 linear alkyl group or the C1 to C5 branched alkyl group may be substituted with at least one selected from deuterium and a halogen element, two functional groups adjacent to each other among $R_{5-1}$, $R_{5-2}$, $R_{5-3}$ and $R_{5-4}$ may be combined with each other to form a ring structure, and two functional groups adjacent to each other among $R_{6-1}$, $R_{6-2}$, $R_{6-3}$ and $R_{6-4}$ may be combined with each other to form a ring structure, wherein in the Chemical Formula 5, each of $R_7$, $R_8$ and $R_9$ independently represents one selected from a group consisting of hydrogen, deuterium, C1 to C5 linear alkyl group and C1 to C5 branched alkyl group, wherein the C1 to C5 linear alkyl group or the C1 to C5 branched alkyl group may be substituted with at least one selected from deuterium and a halogen element, and two functional groups adjacent to each other among $R_7$, $R_8$ and $R_9$ may combine with each other to form a ring structure.

As described above, the ancillary ligand bound to iridium (Ir) as a central coordination metal may be the bidentate ligand. The bidentate ligand may contain an electron donor, thereby increasing an amount of MLCT (metal to ligand charge transfer), thereby allowing the organic light-emitting diode to exhibit improved luminous properties such as high luminous efficiency and high external quantum efficiency.

The organometallic compound according to an embodiment of the present disclosure may have a heteroleptic or homoleptic structure. Specifically, the organometallic compound according to an embodiment of the present disclosure may have a heteroleptic structure in which in the Chemical Formula 1, m is 1 and n is 2; or a heteroleptic structure where m is 2 and n is 1; or a homoleptic structure where m is 3 and n is 0.

A specific example of the compound represented by the Chemical Formula 1 of the present disclosure may include one selected from a group consisting of following compounds 1 to 510. However, the specific example of the compound represented by the Chemical Formula 1 of the present disclosure is not limited thereto as long as it meets the above definition of the Chemical Formula 1:

1

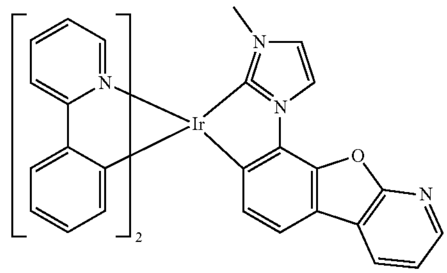

2

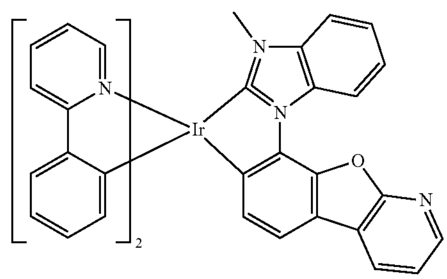

3

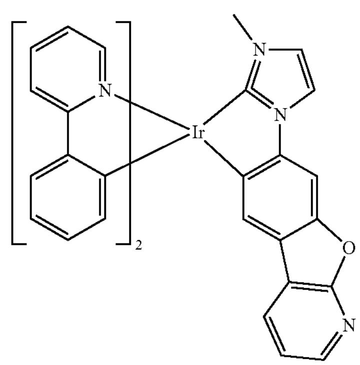

4

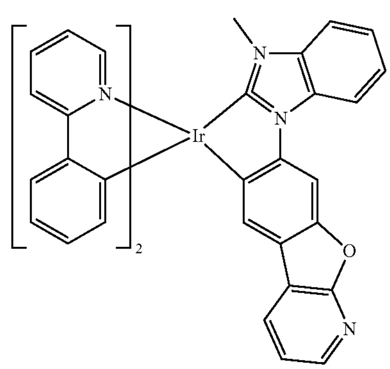

-continued
5
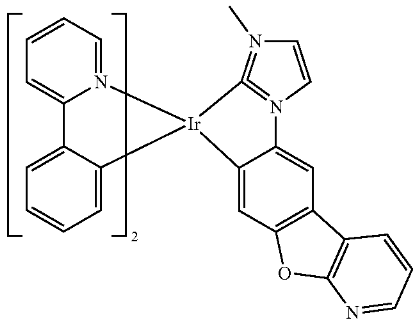
6
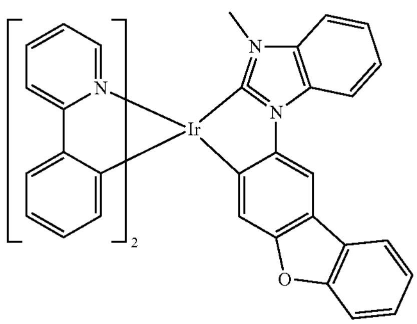
7
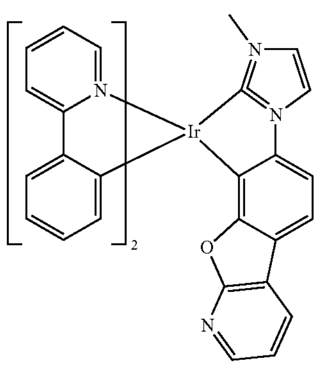
8
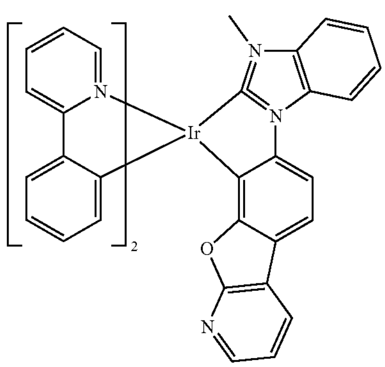
9
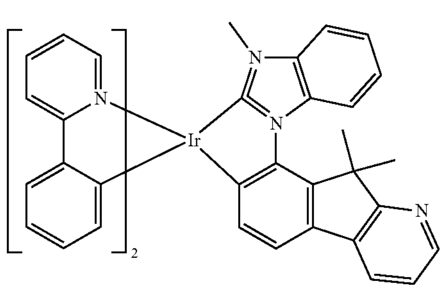
-continued
10
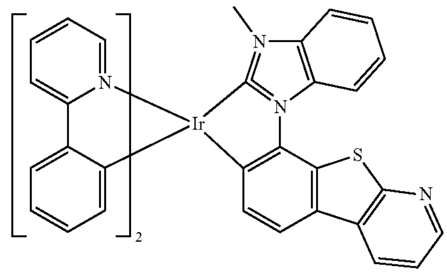
11
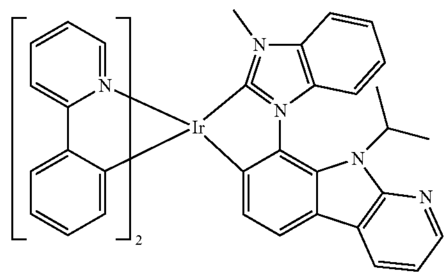
12
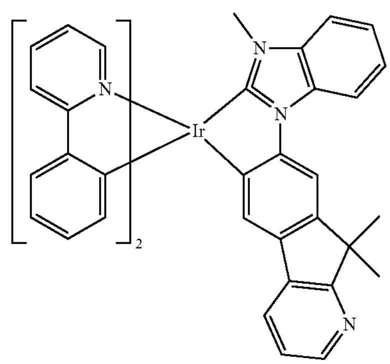
13
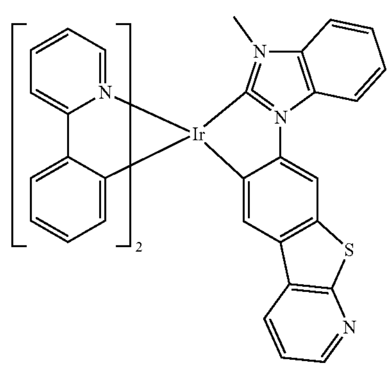
14
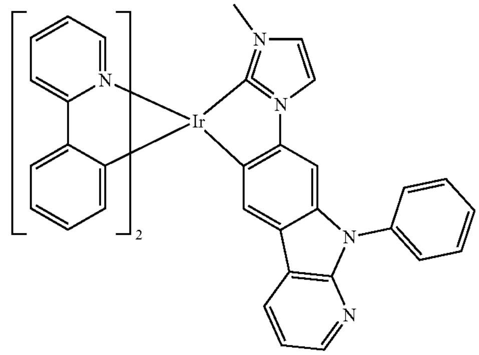

-continued
15
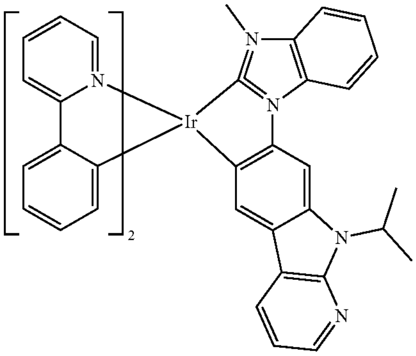
16
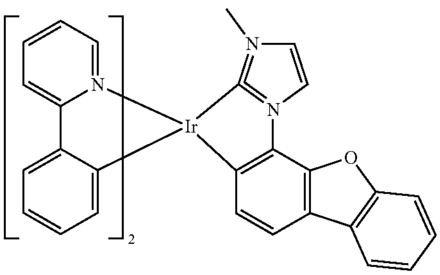
17
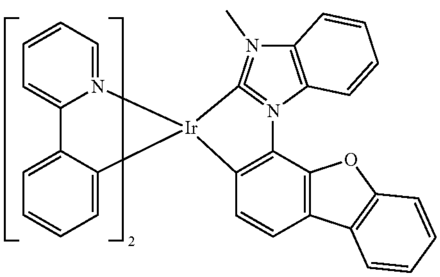
18
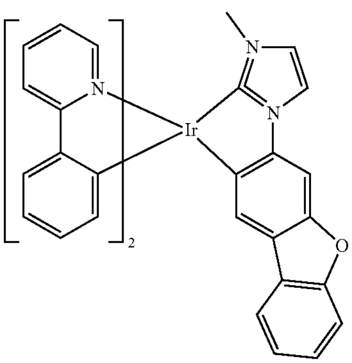
19
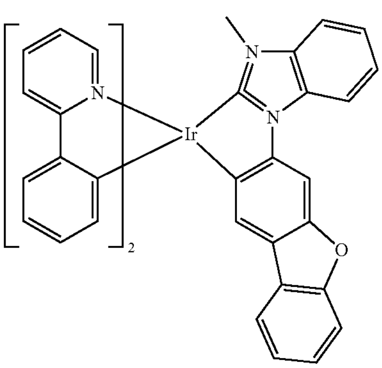
-continued
20
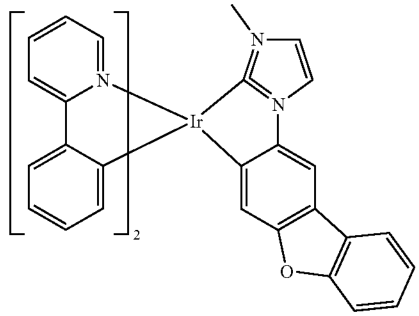
21
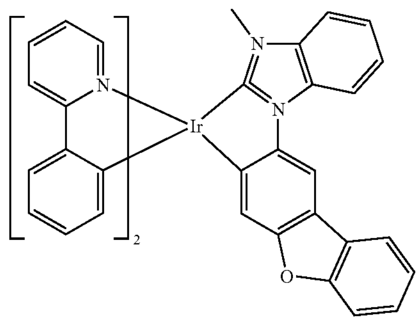
22
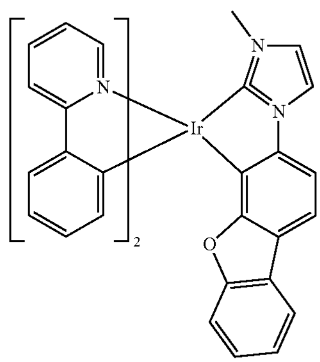
23
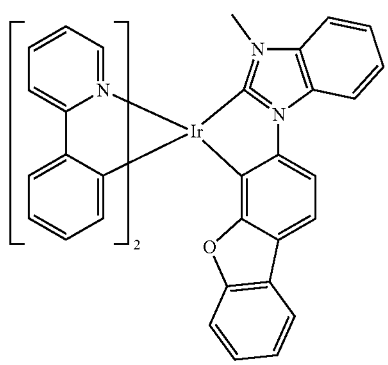
24
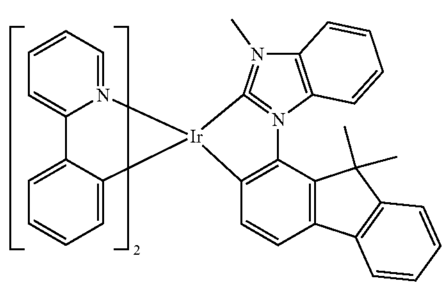

-continued
25
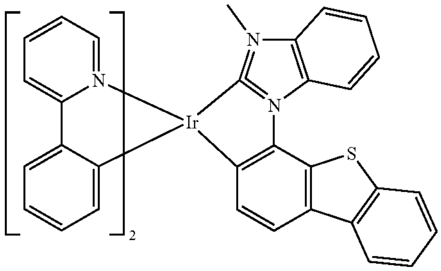
26
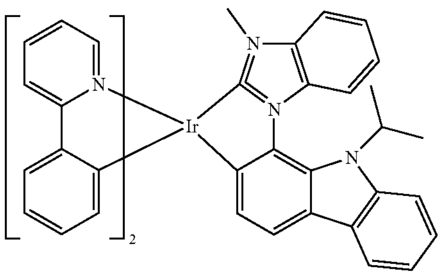
27
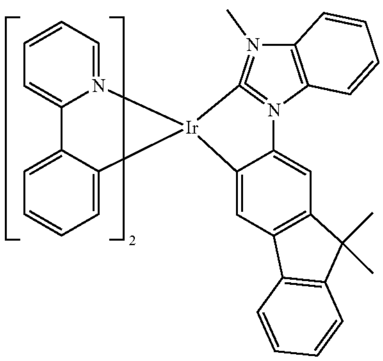
28
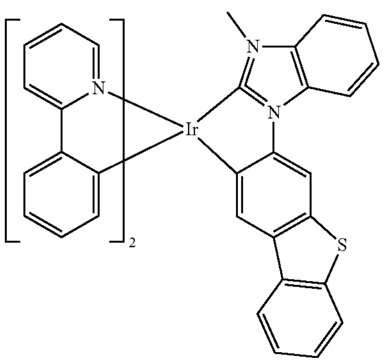
29
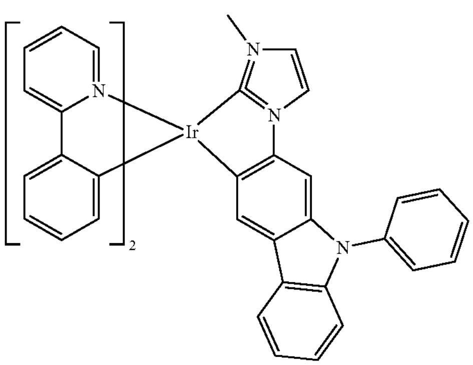
-continued
30
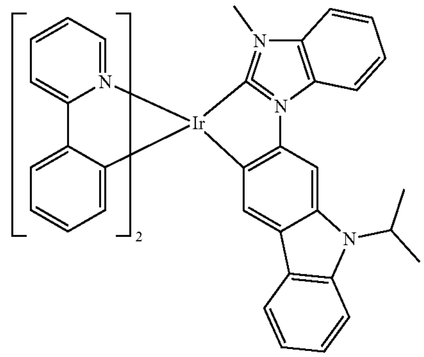
31
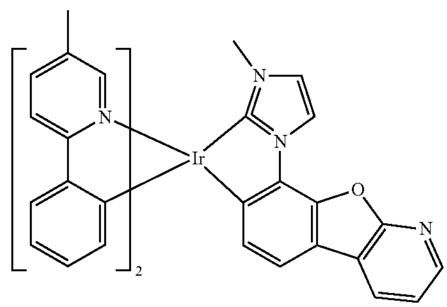
32
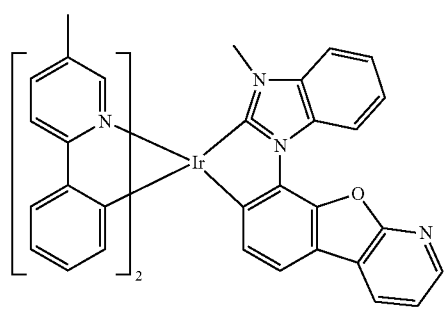
33
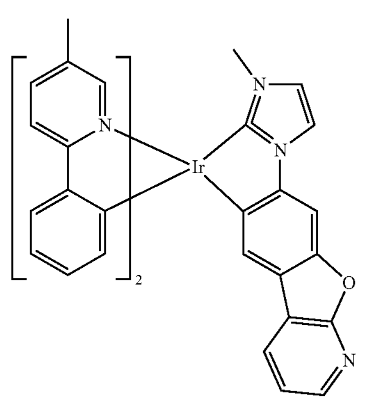

-continued
34
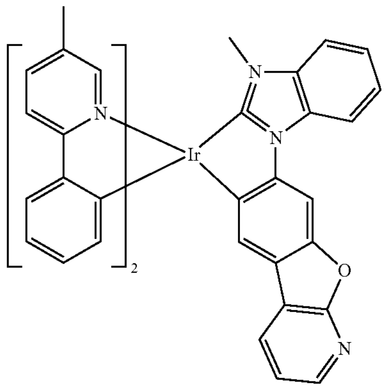
35
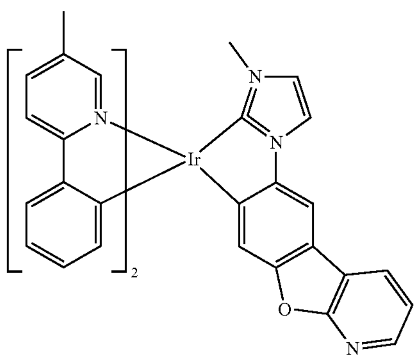
36
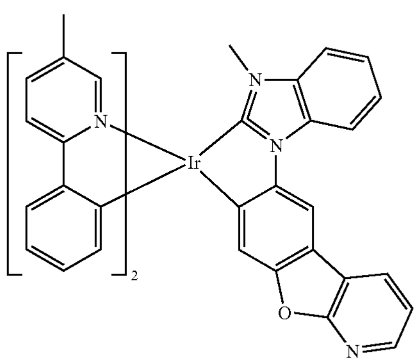
37
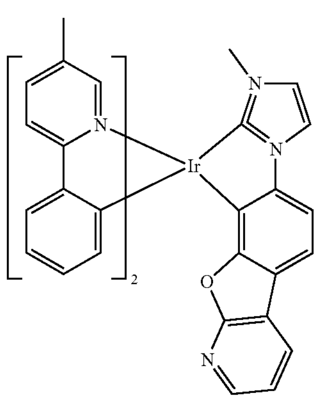
-continued
38
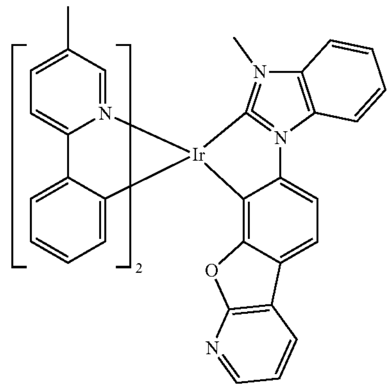
39
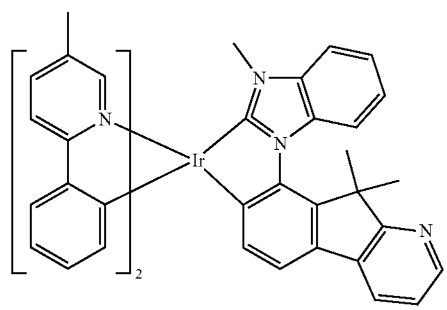
40
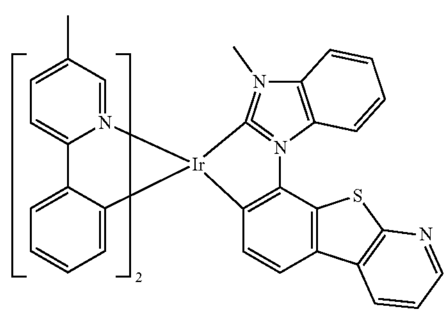
41
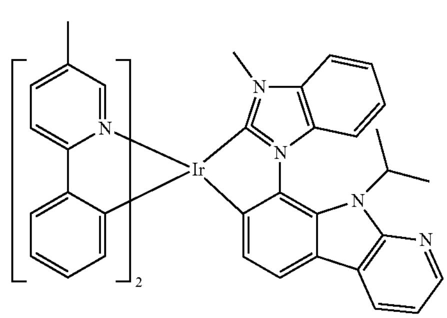

-continued
42
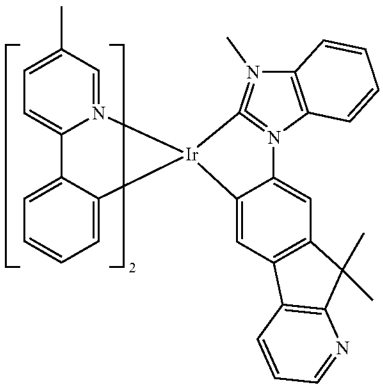
43
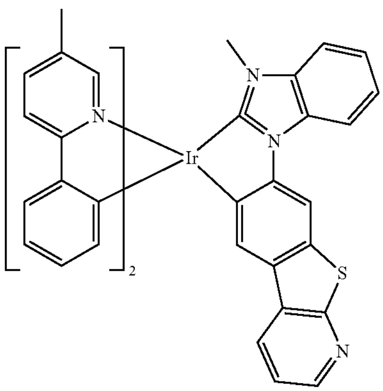
44
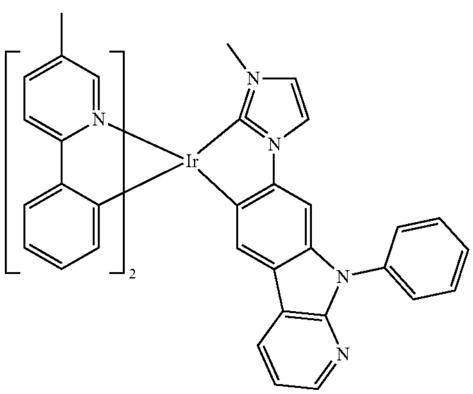
45
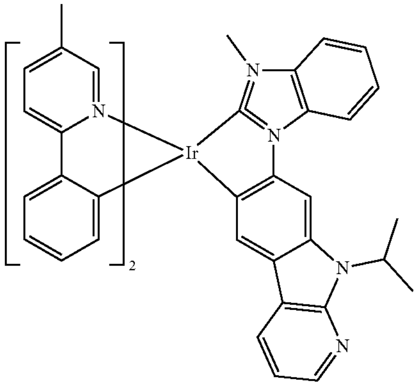
-continued
46
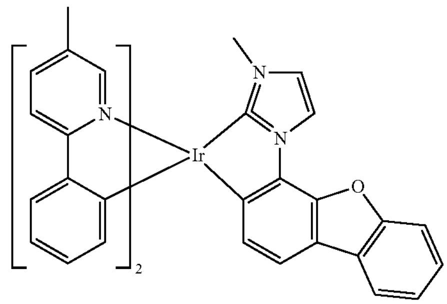
47
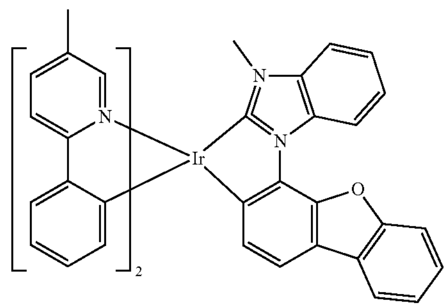
48
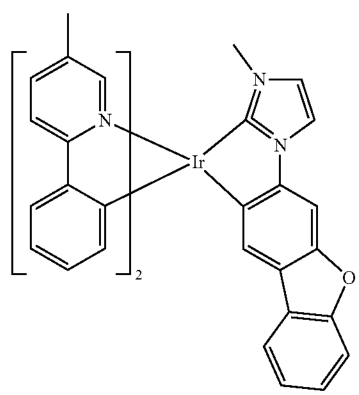
49
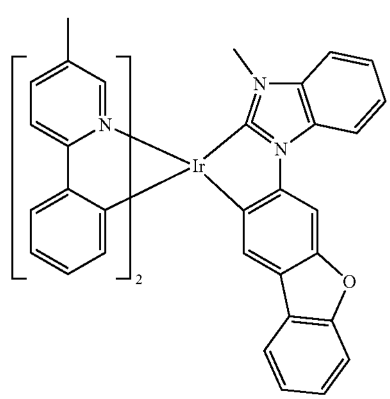

-continued
50
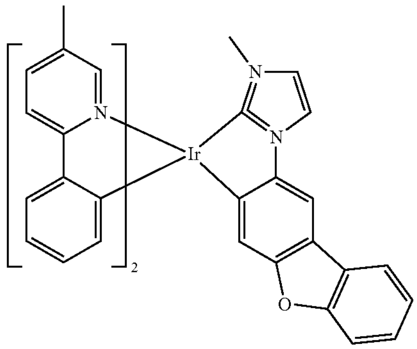
51
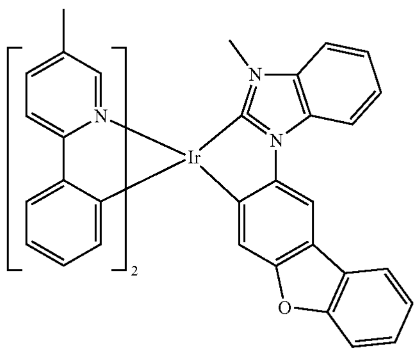
52
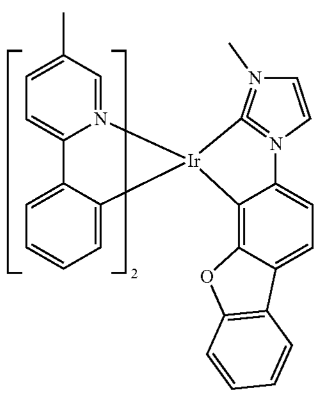
53
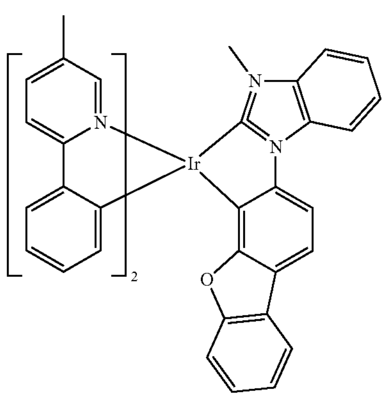
-continued
54
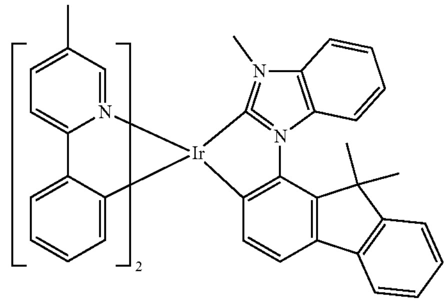
55
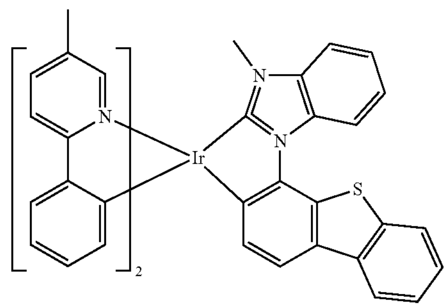
56
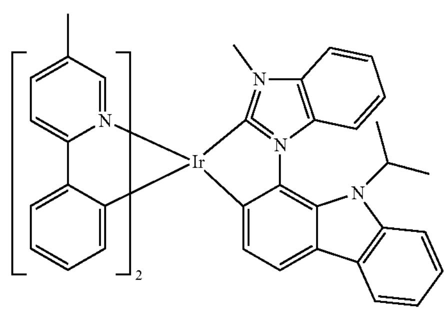
57
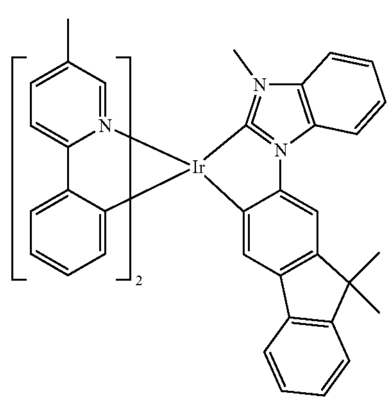

-continued
58
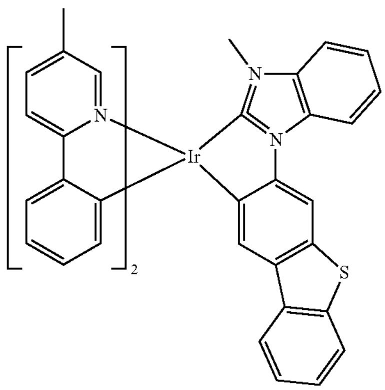
59
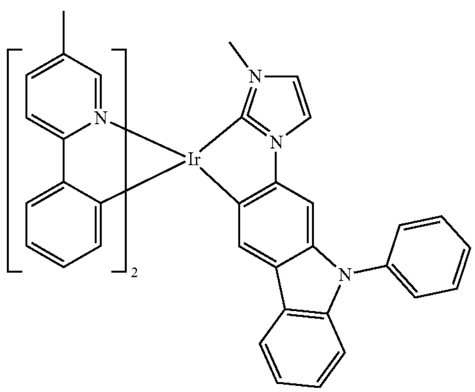
60
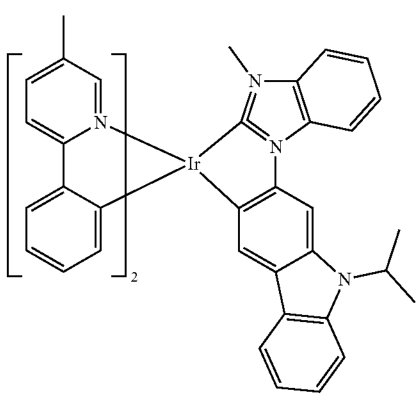
61
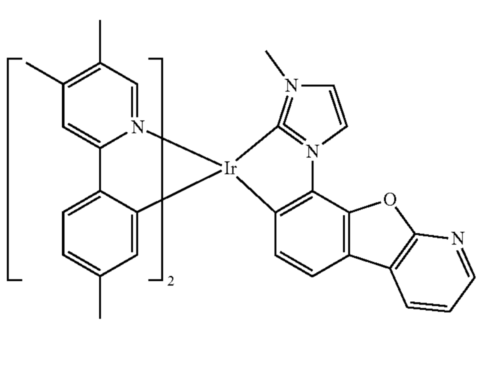
-continued
62
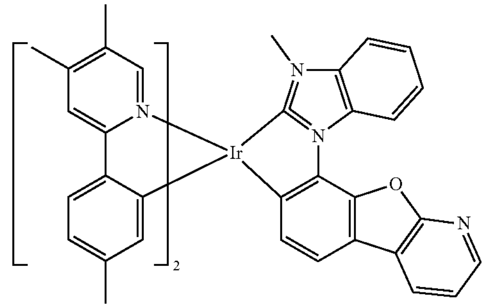
63
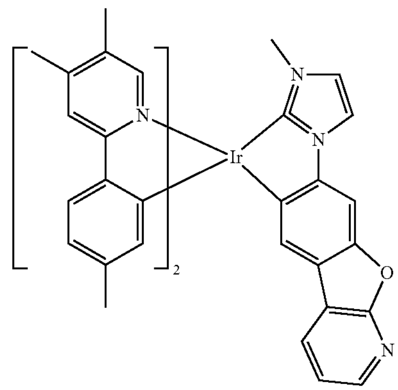
64
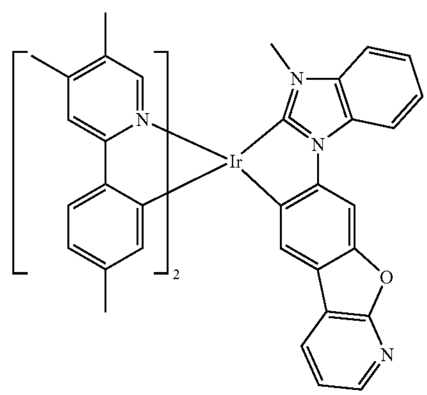
65
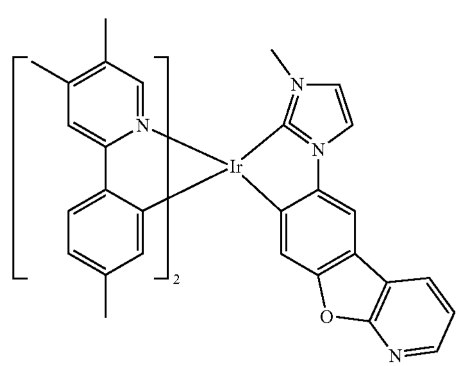

-continued
66
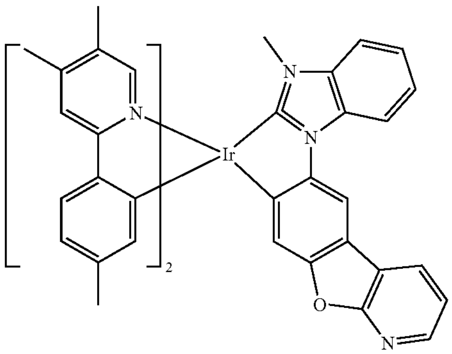
67
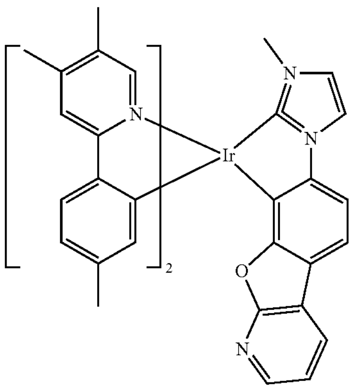
68
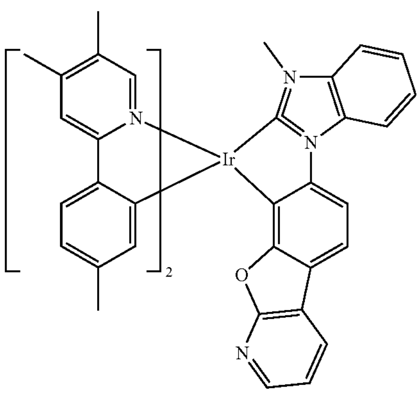
69
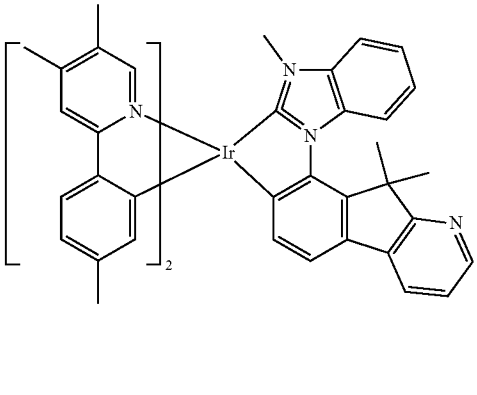
-continued
70
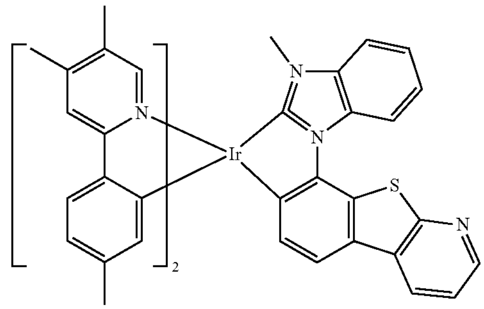
71
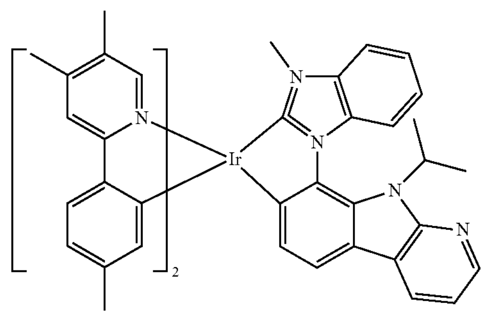
72
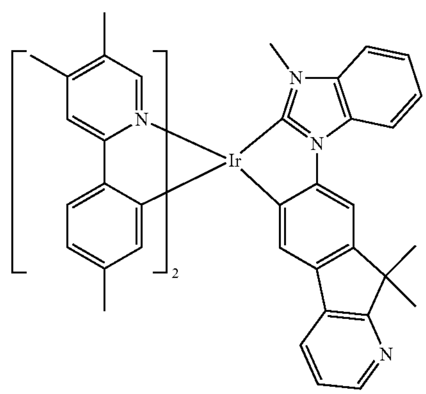
73
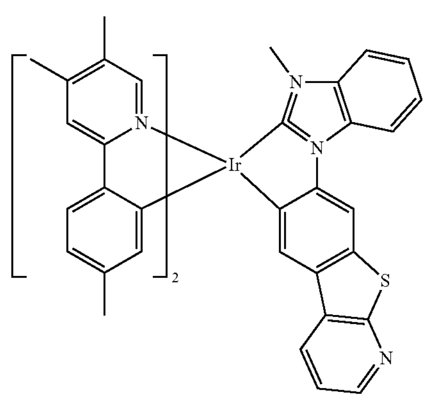

74
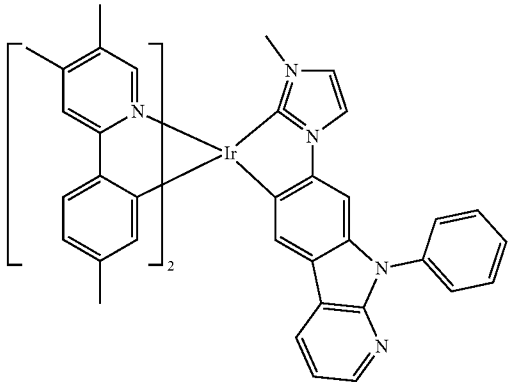
75
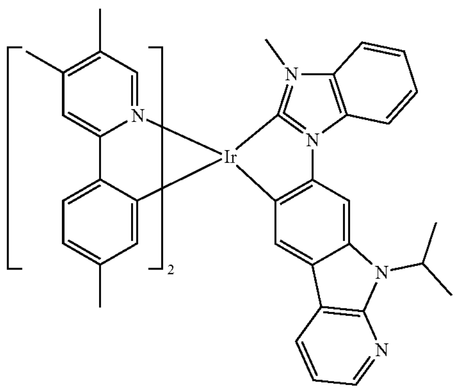
76
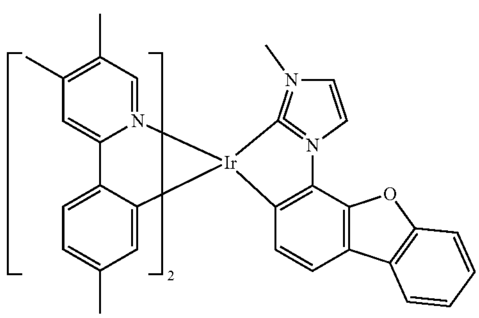
77
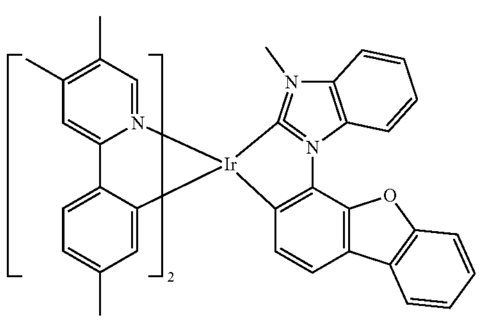
78
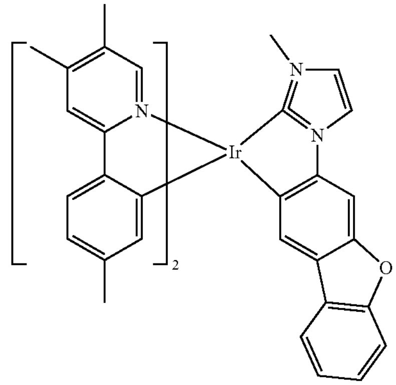
79
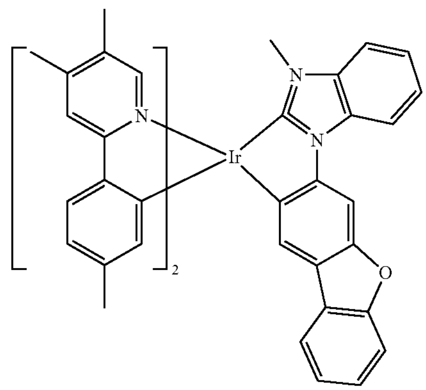
80
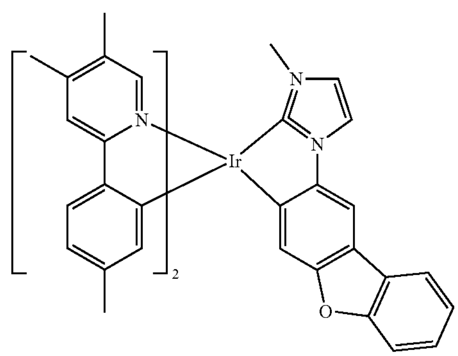
81
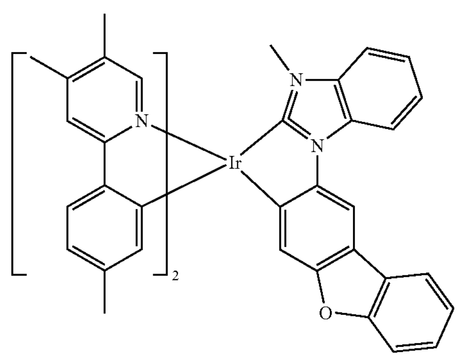

-continued
82
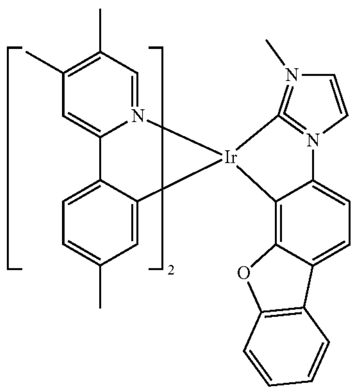
83
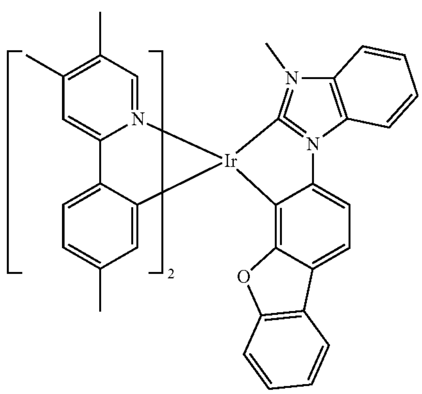
84
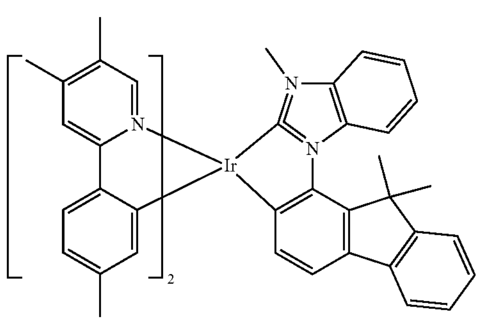
85
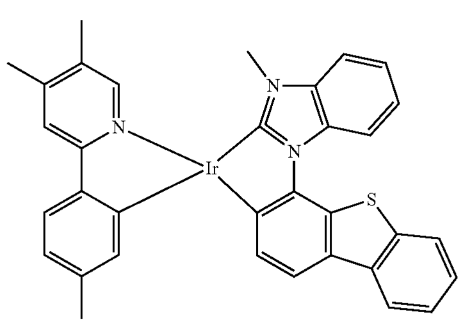
-continued
86
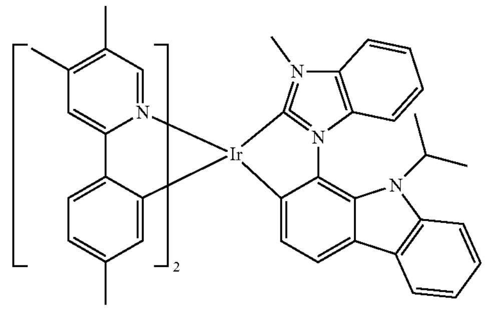
87
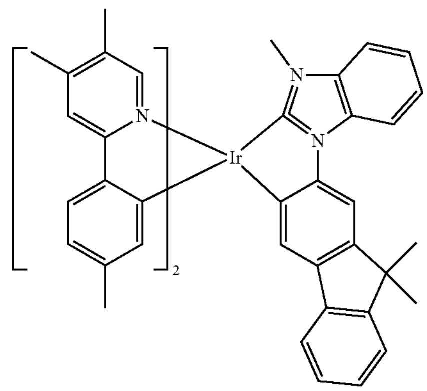
88
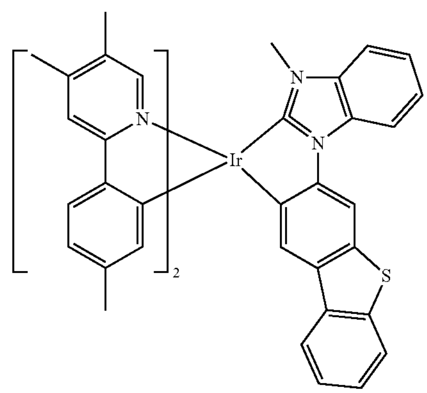
89
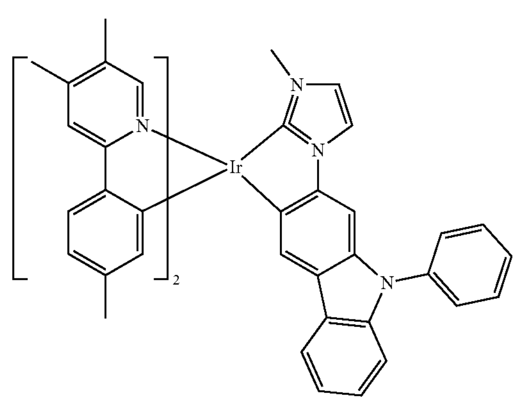

-continued
90
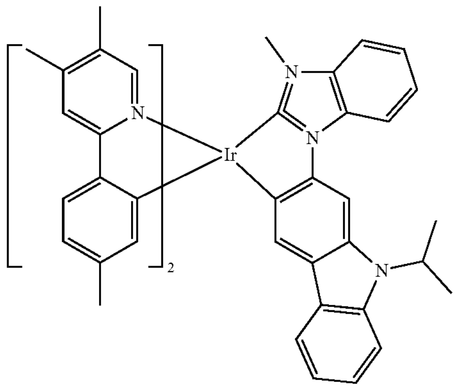
91
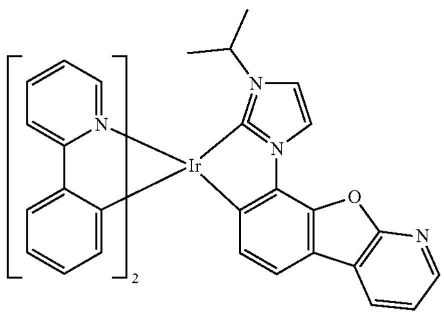
92
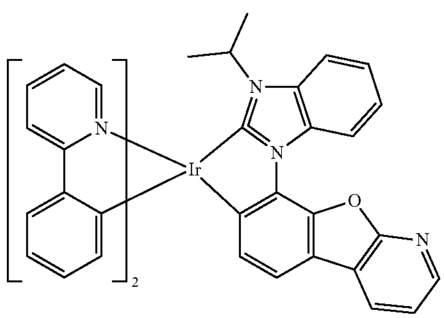
93
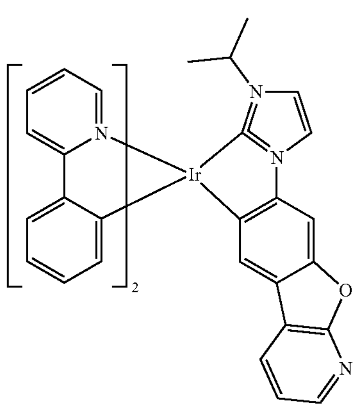
-continued
94
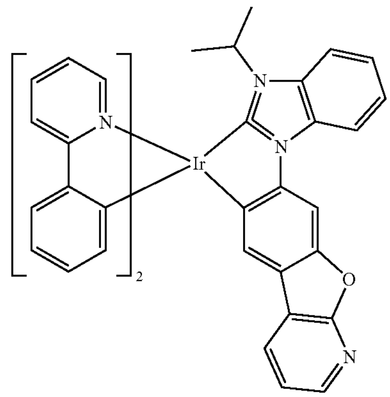
95
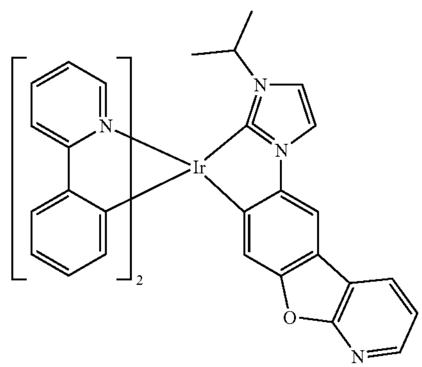
96
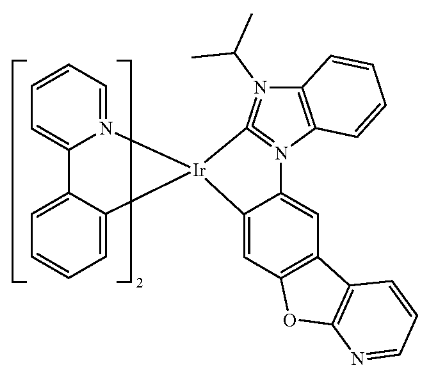
97
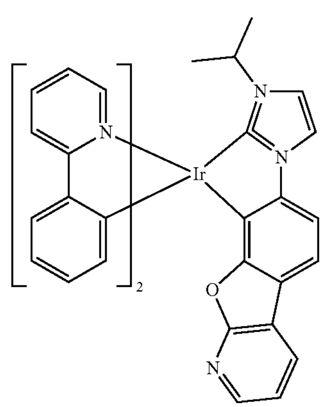

-continued
98
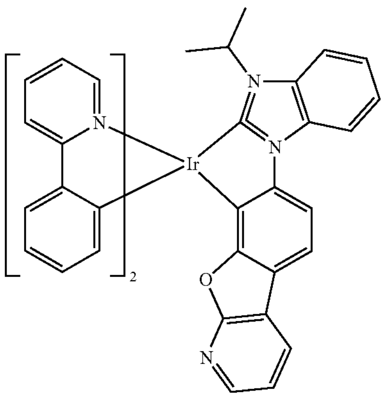
99
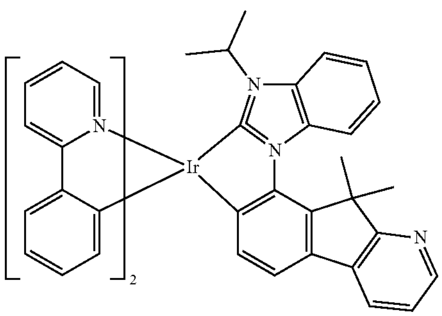
100
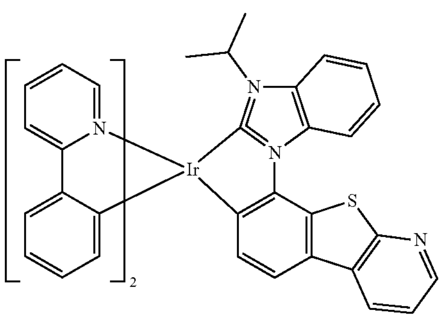
101
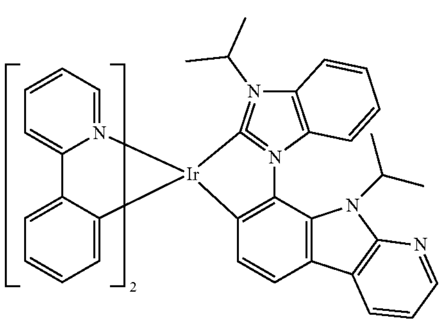
-continued
102
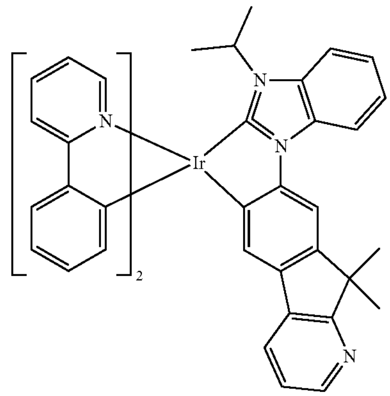
103
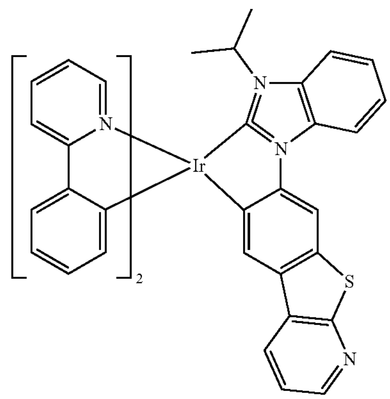
104
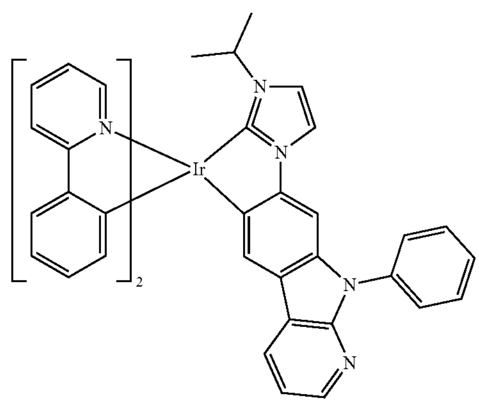
105
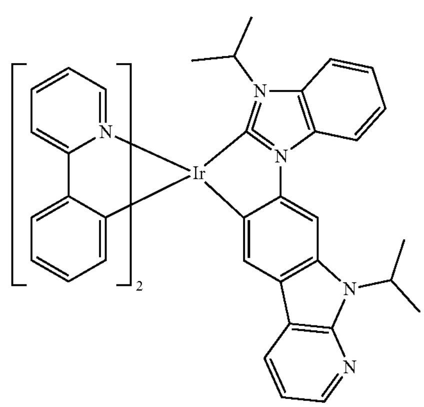

-continued
106
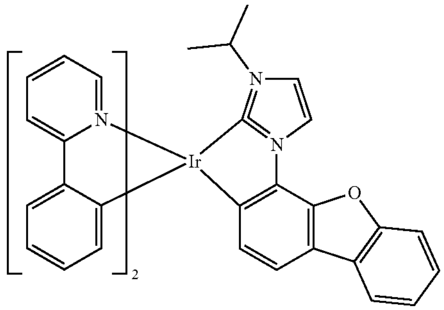
107
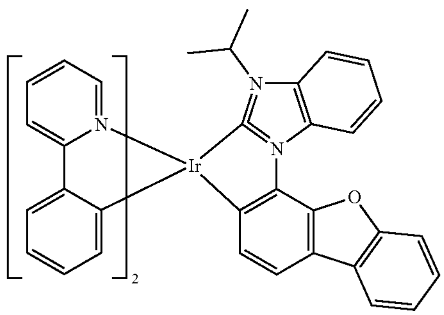
108
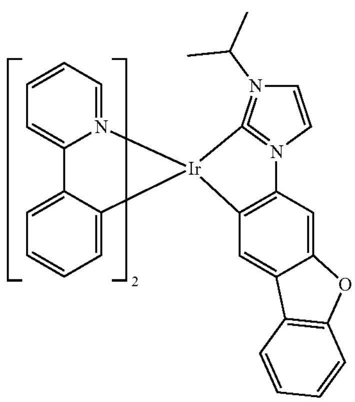
109
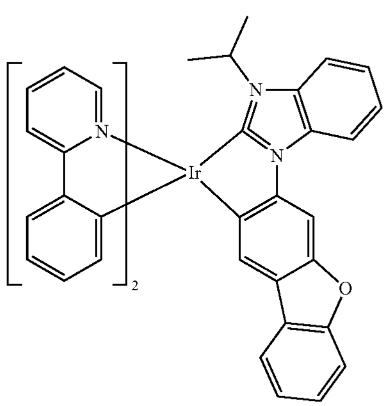
-continued
110
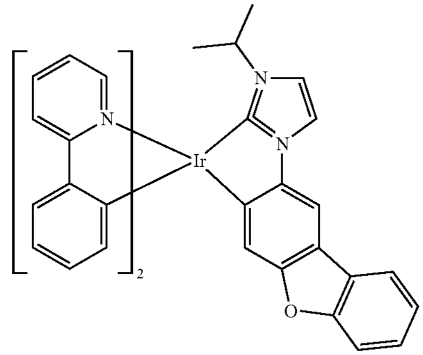
111
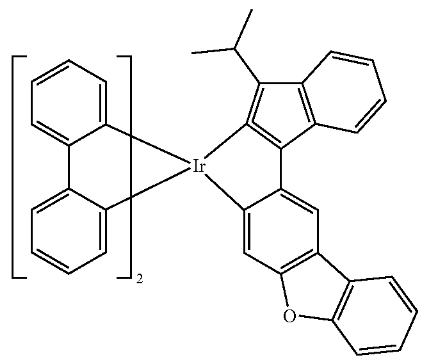
112
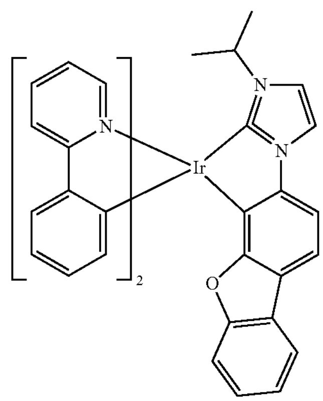
113
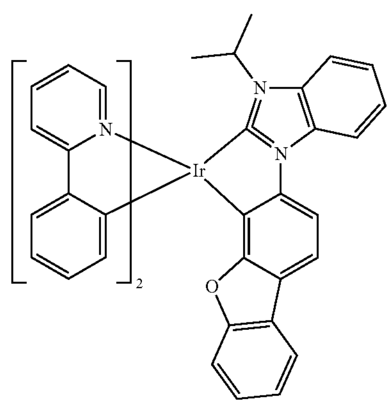

-continued
114
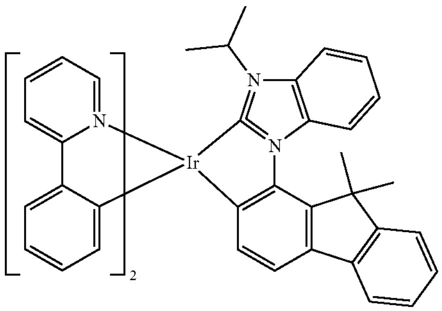
115
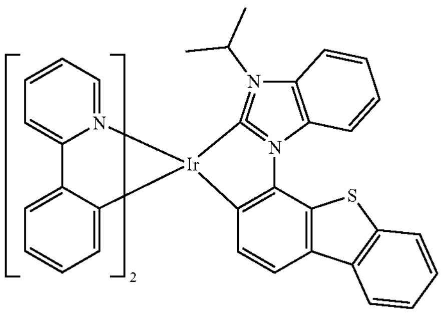
116
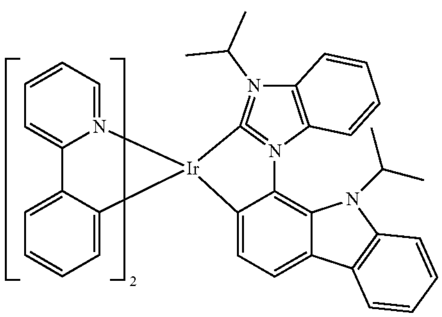
117
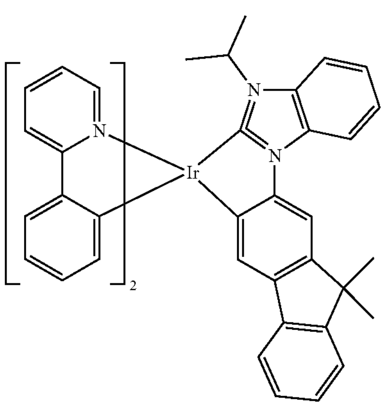
-continued
118
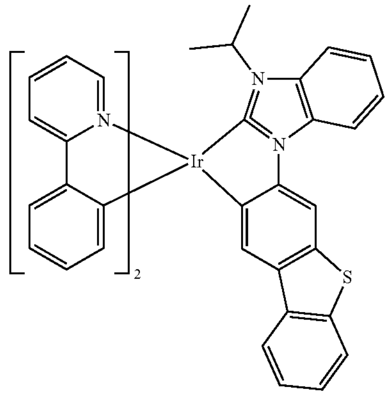
119
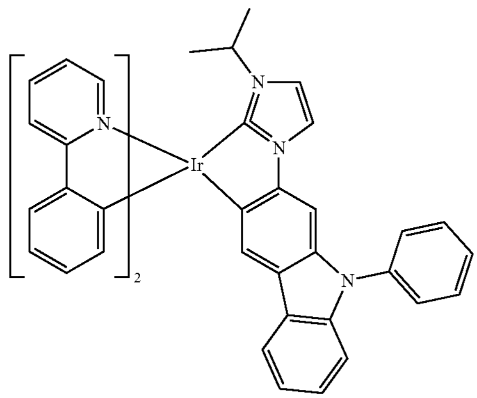
120
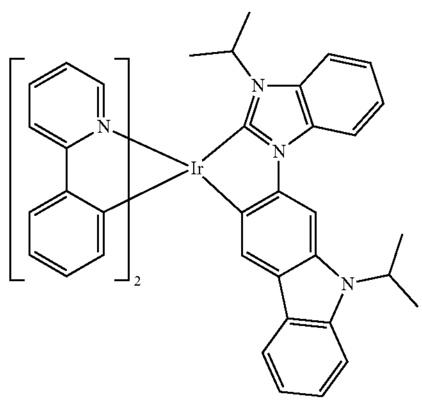
121
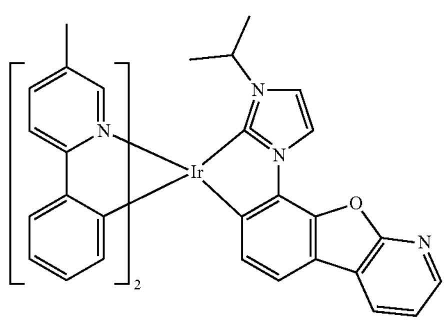

-continued
122
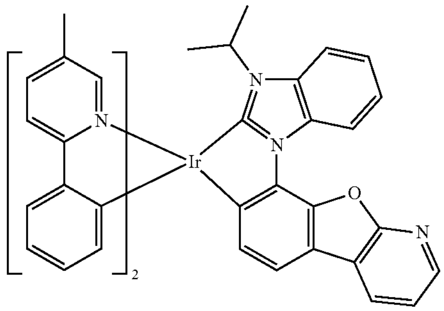
123
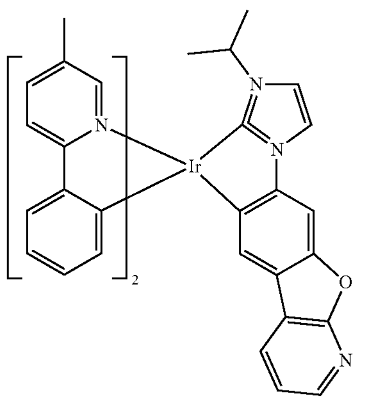
124
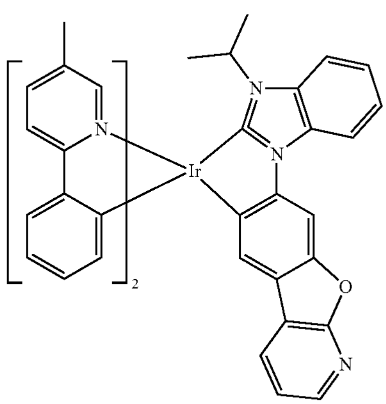
125
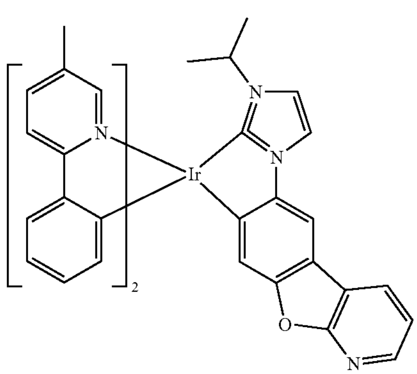
-continued
126
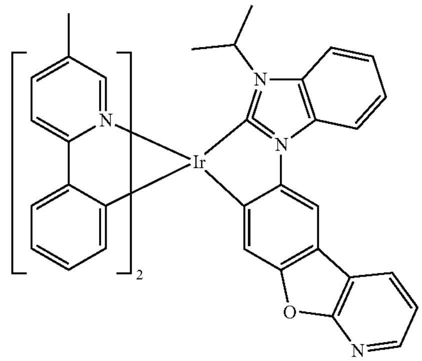
112
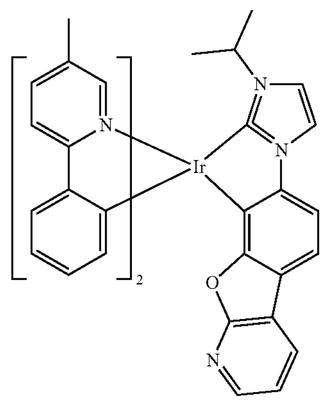
128
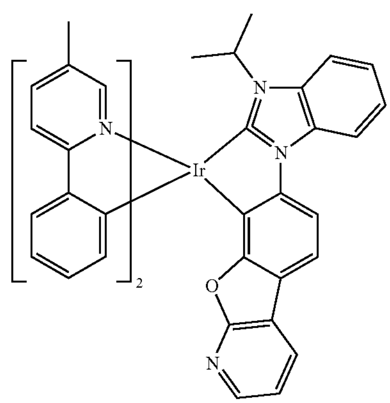
129
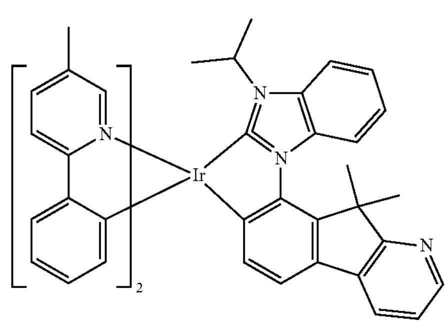

-continued
130
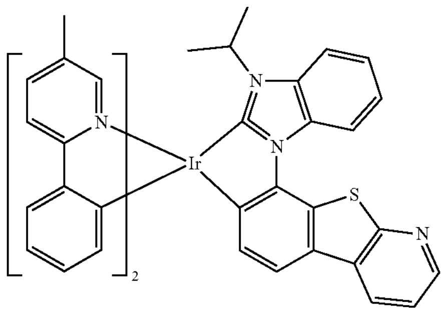
131
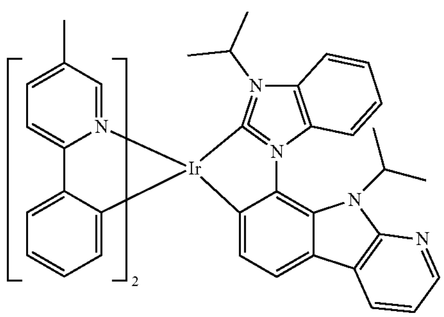
132
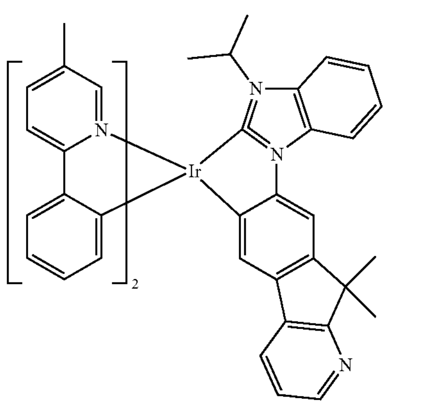
133
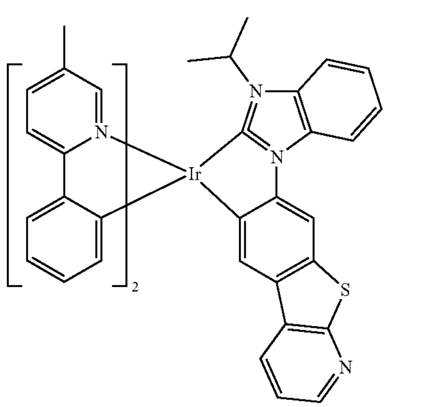
-continued
134
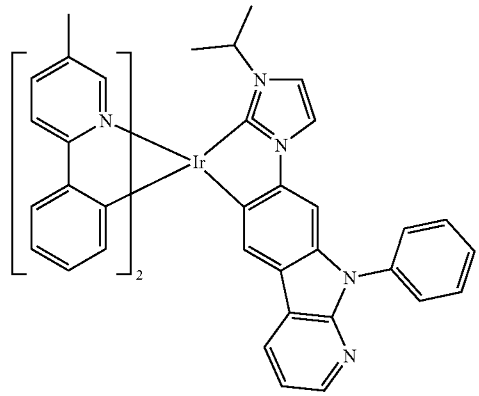
135
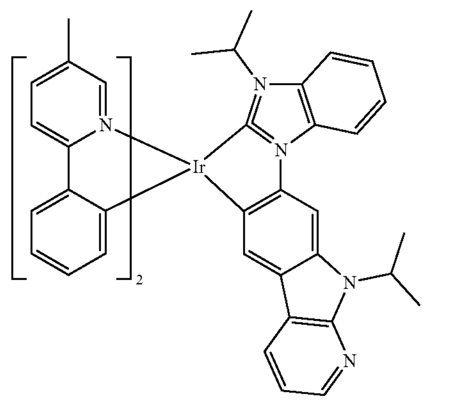
136
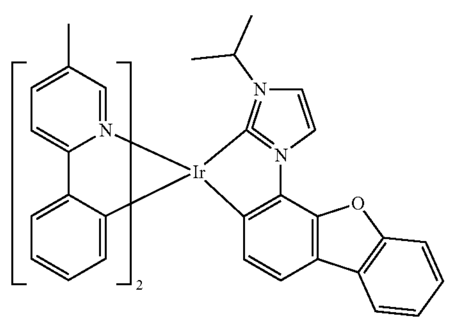
137
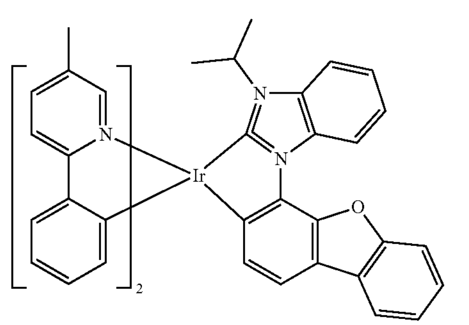

-continued
138
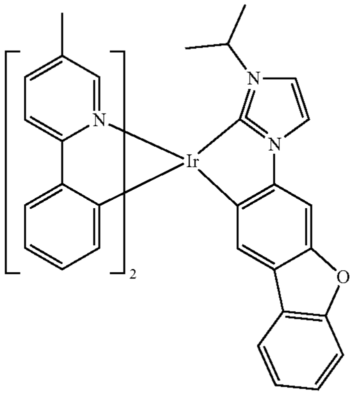
139
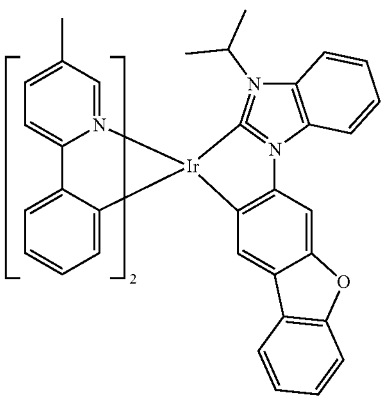
140
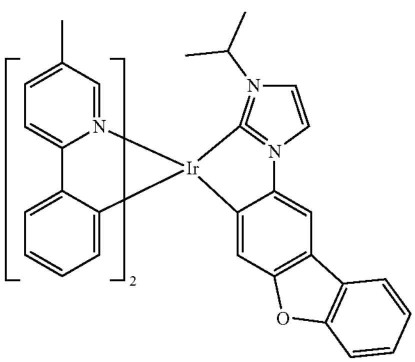
141
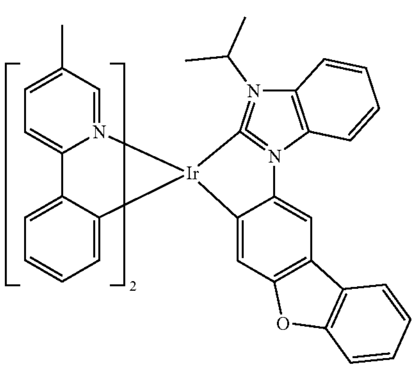
-continued
142
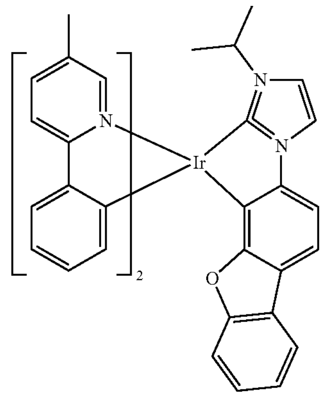
143
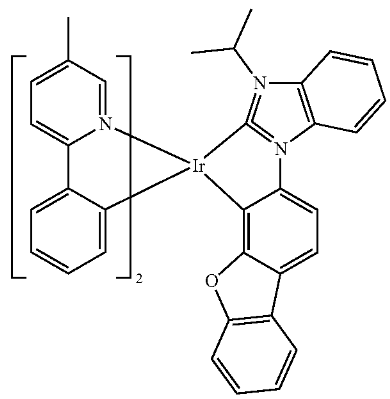
144
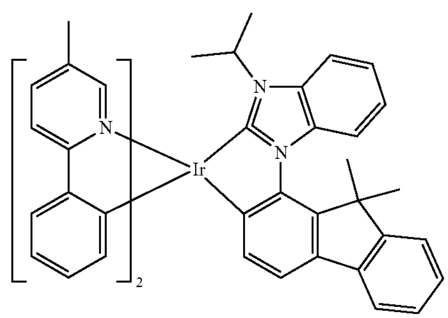
145
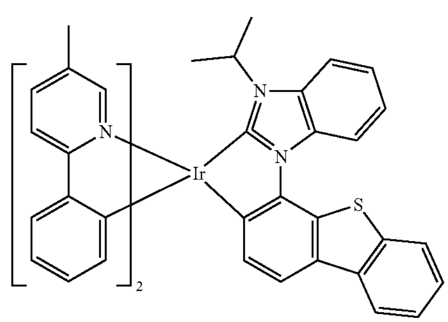

-continued
146
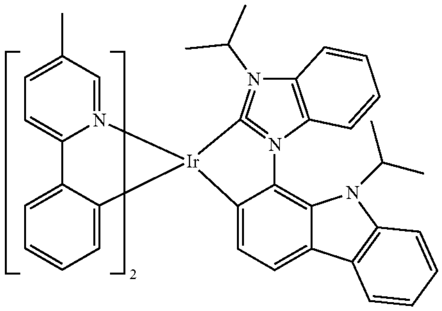
147
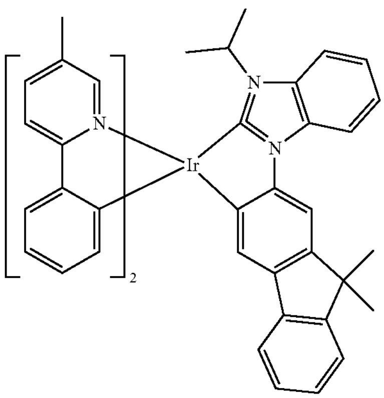
148
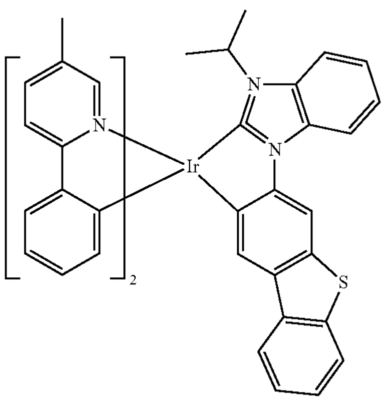
149
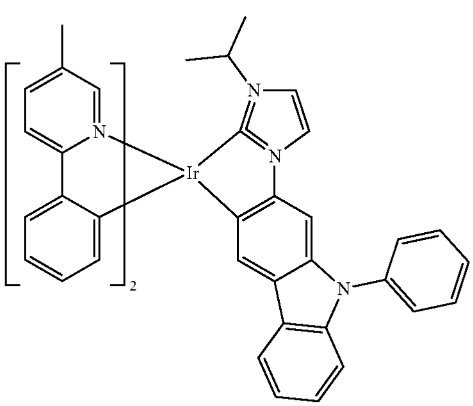
-continued
150
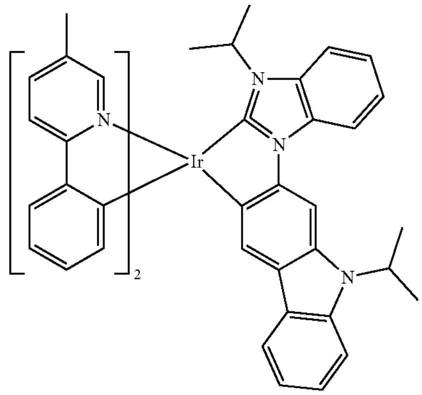
151
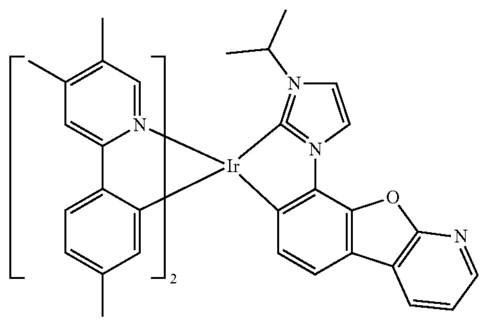
152
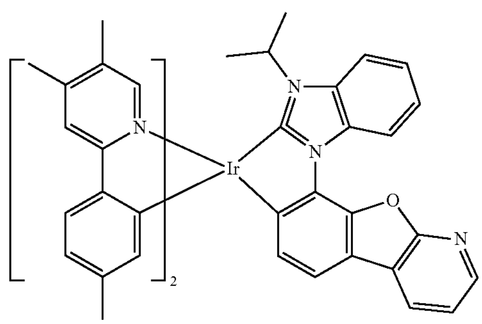
153
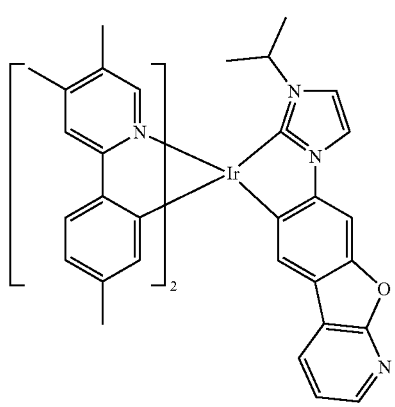

-continued
154
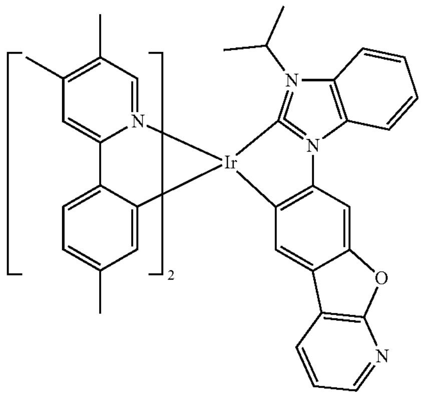
155
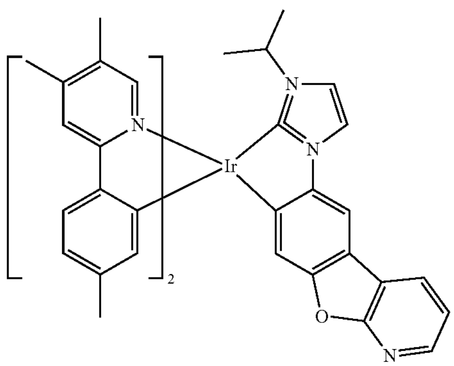
156
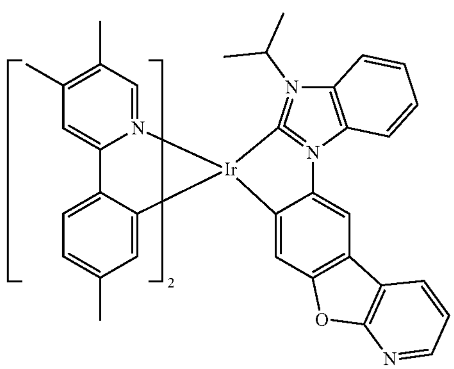
157
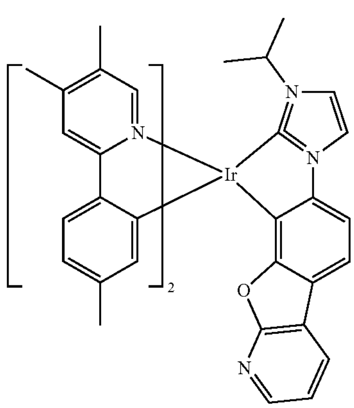
-continued
158
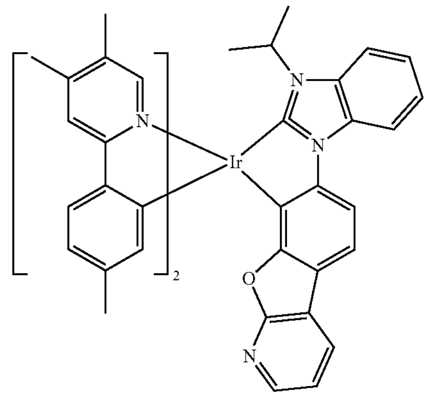
159
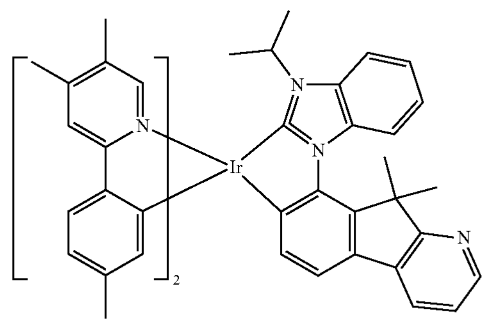
160
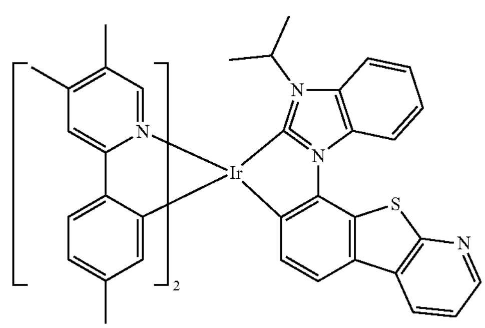
161
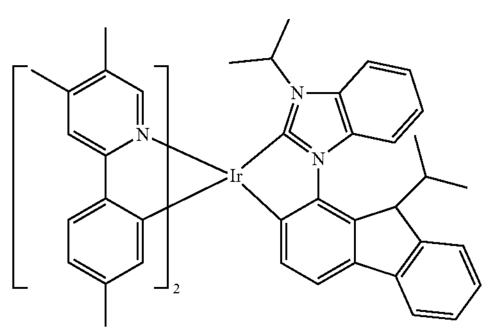

-continued
162
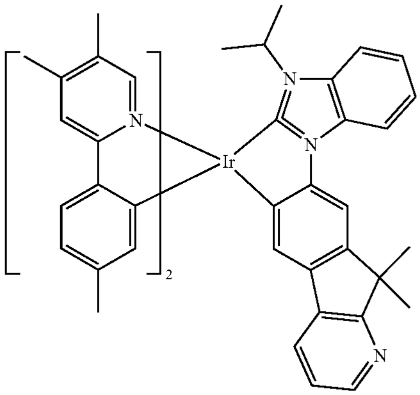
163
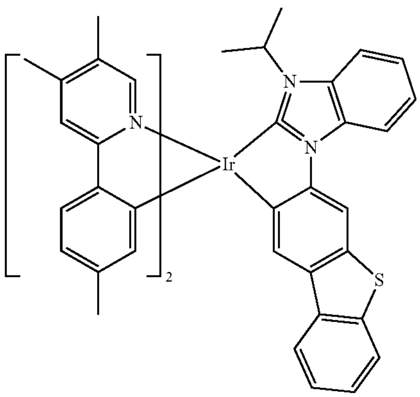
164
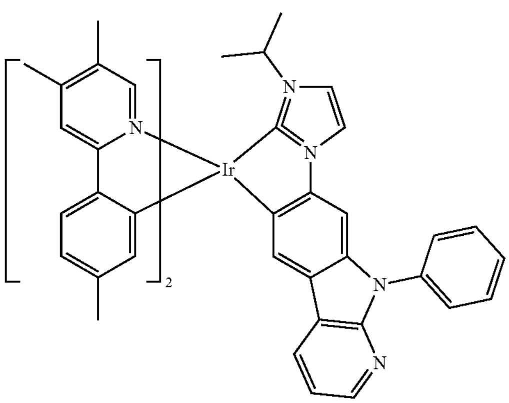
165
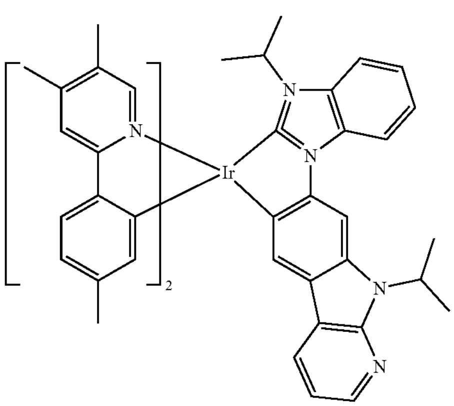
-continued
166
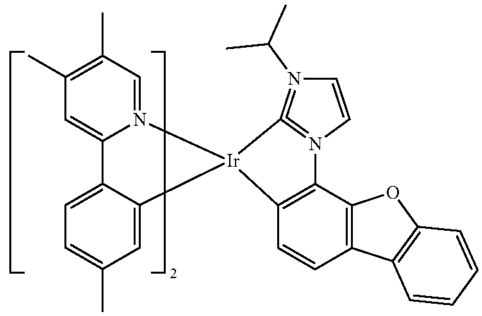
167
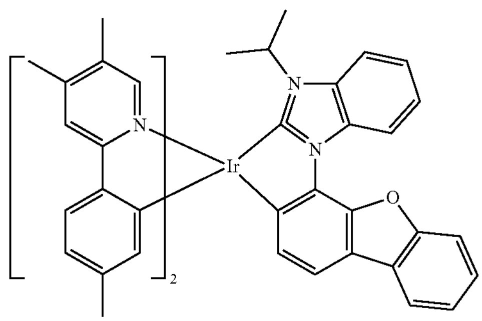
168
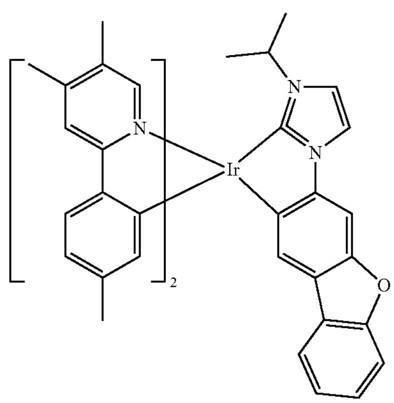
169
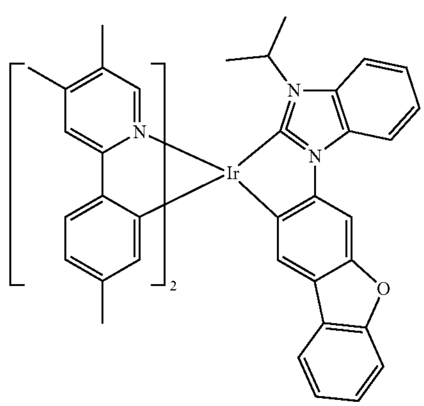

-continued
170
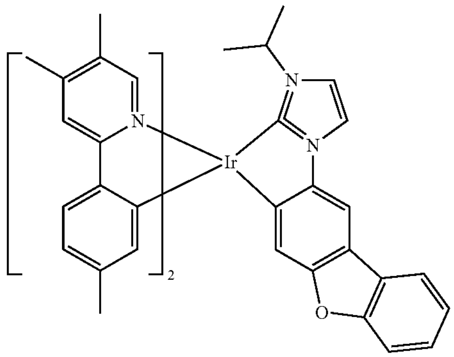
171
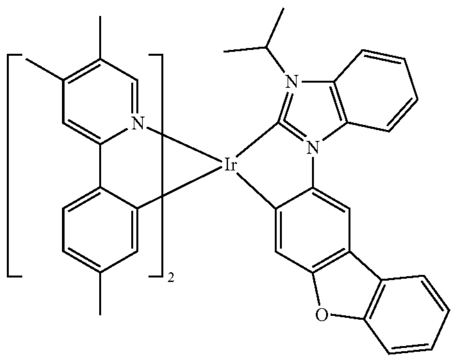
172
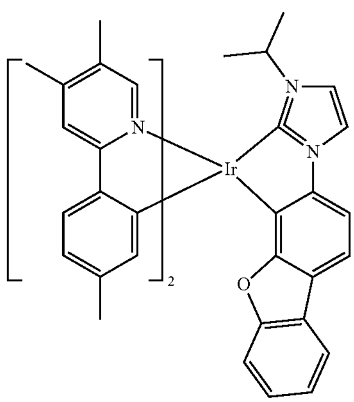
173
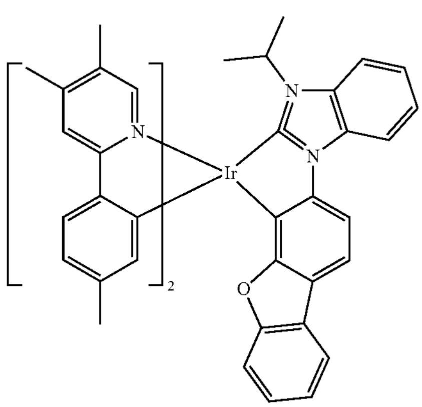
-continued
174
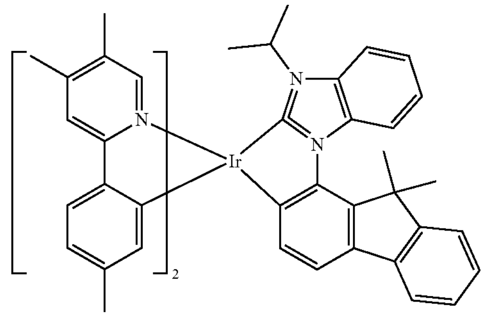
175
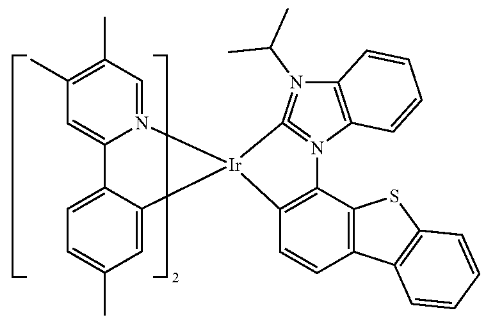
176
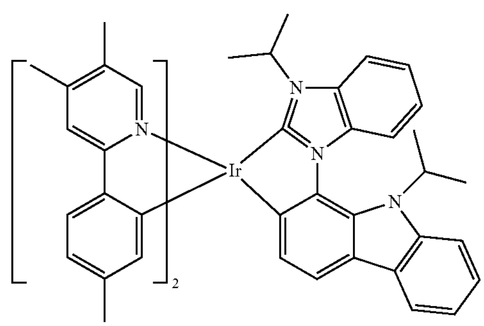
177
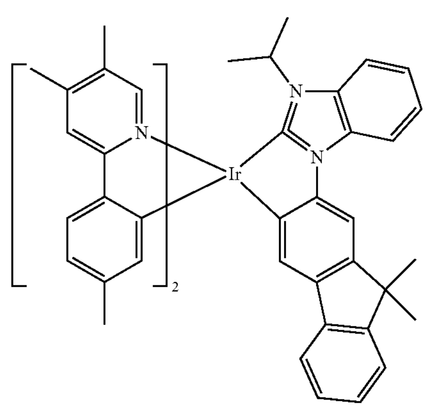

-continued
178
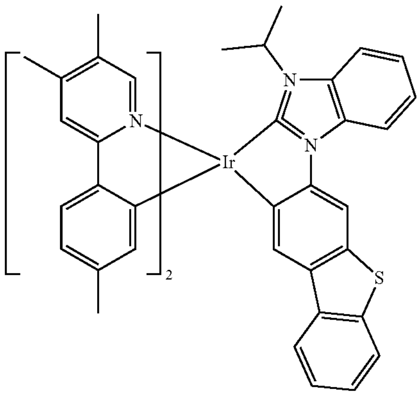
179
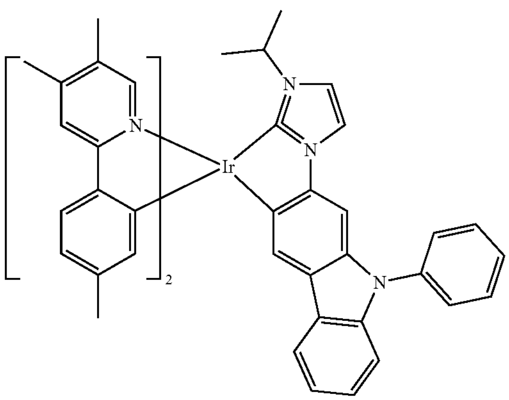
180
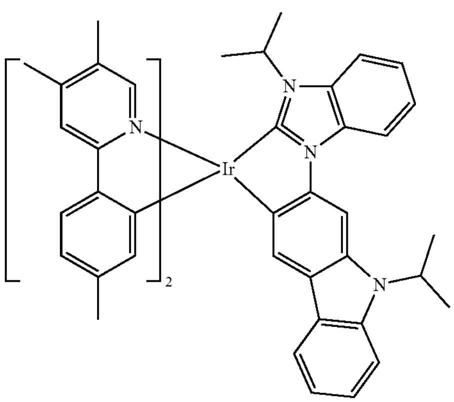
181
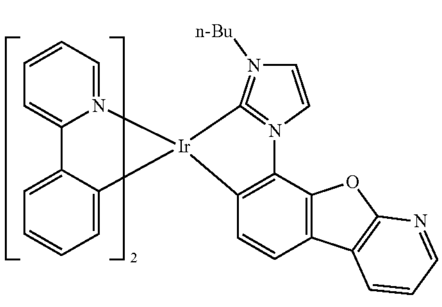
-continued
182
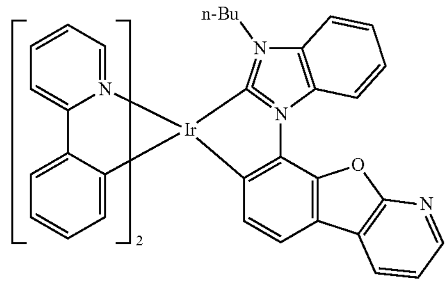
183
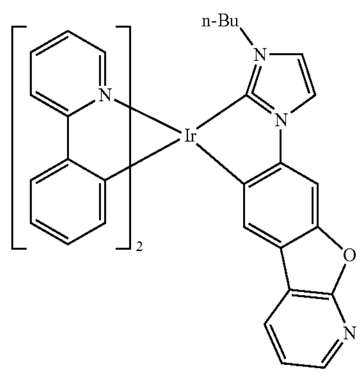
184
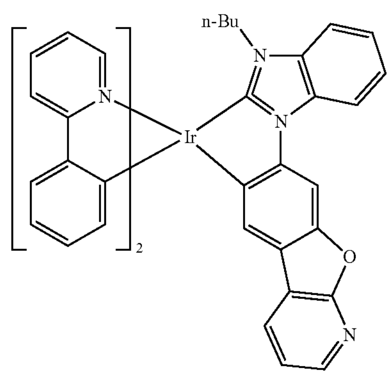
185
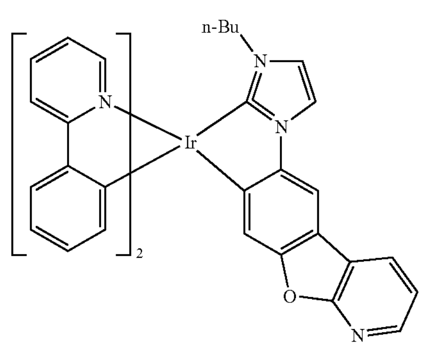

-continued
186
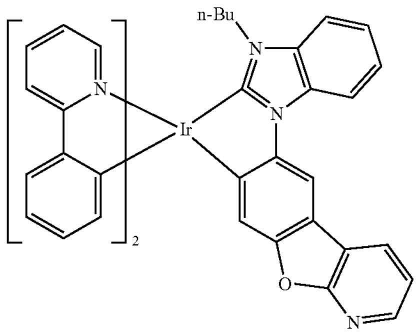
187
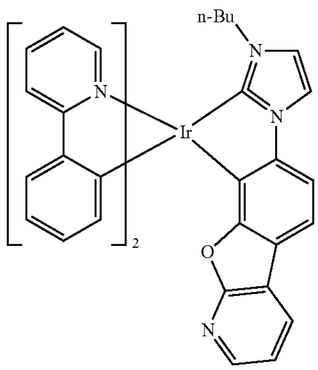
188
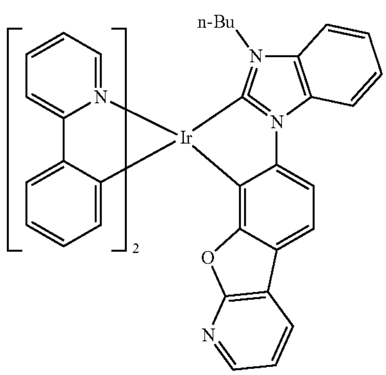
189
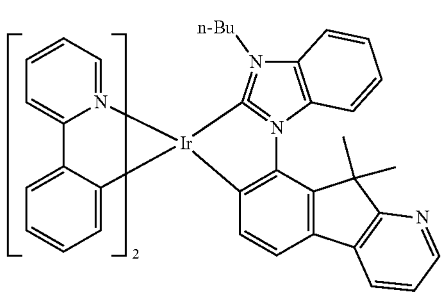
190
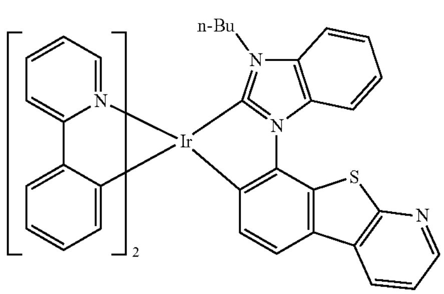
-continued
191
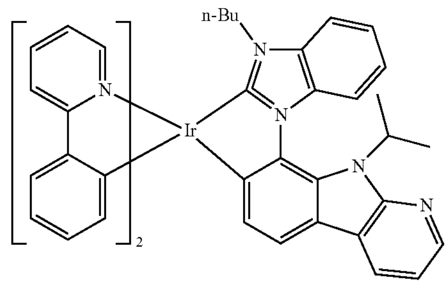
192
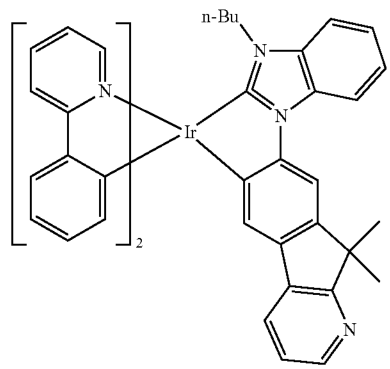
193
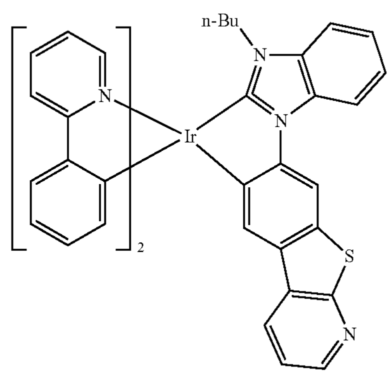
194
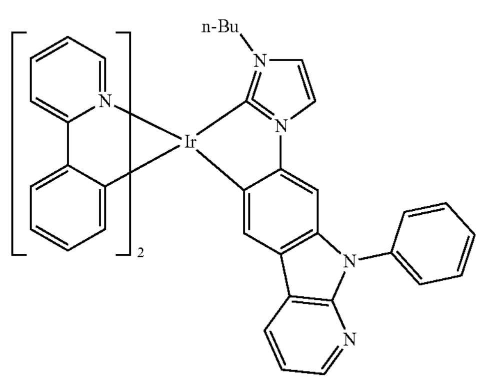

-continued
195
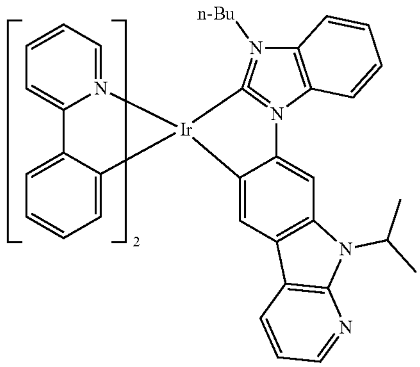
196
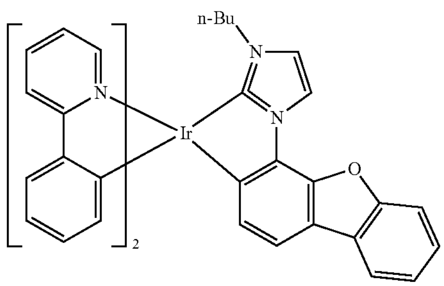
197
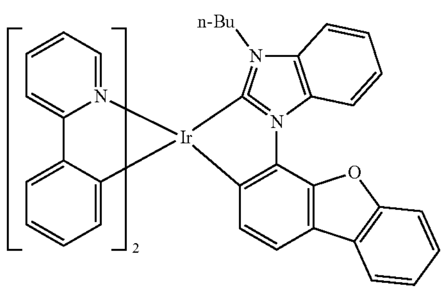
198
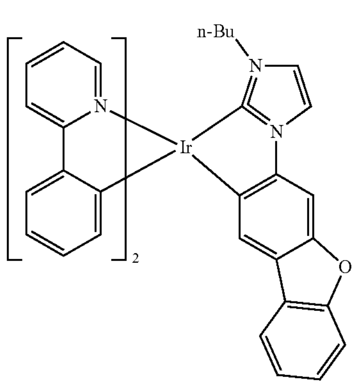
-continued
199
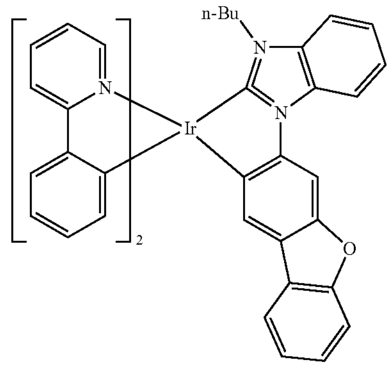
200
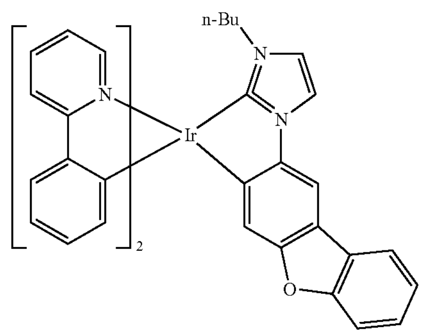
201
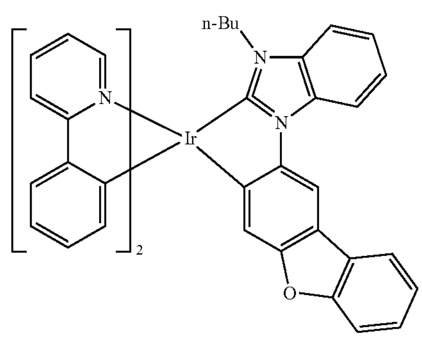
202
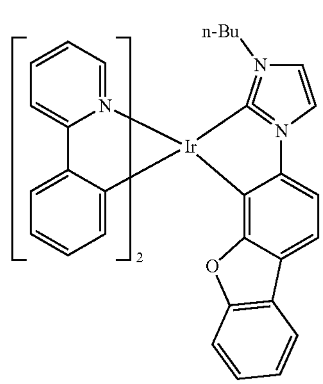

-continued
203
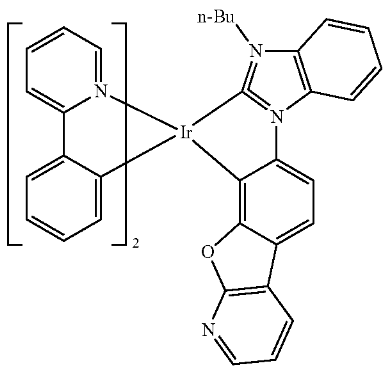
204
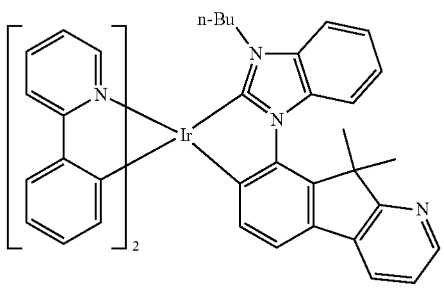
205
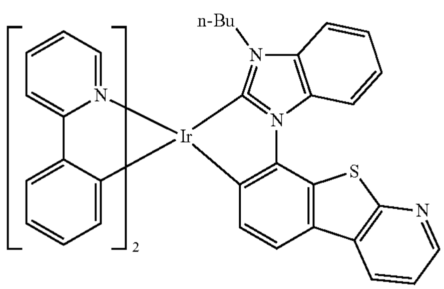
206
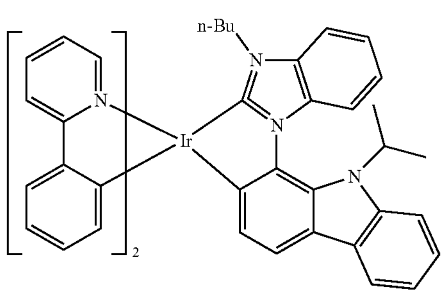
207
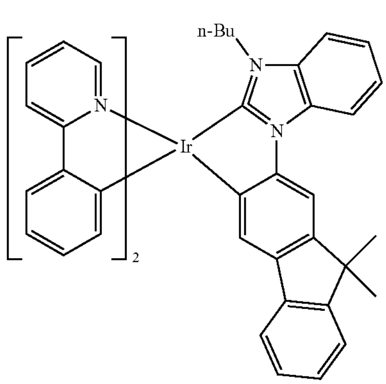
-continued
208
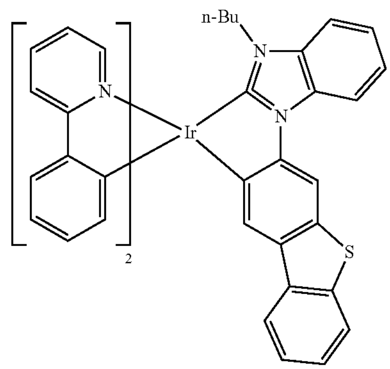
209
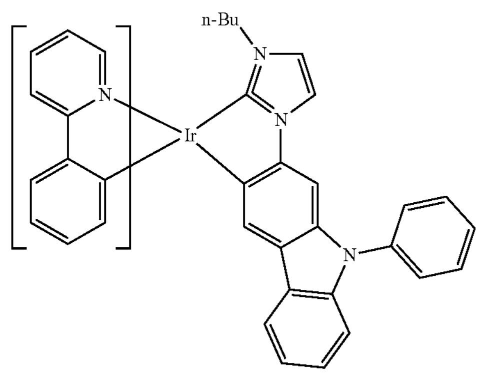
210
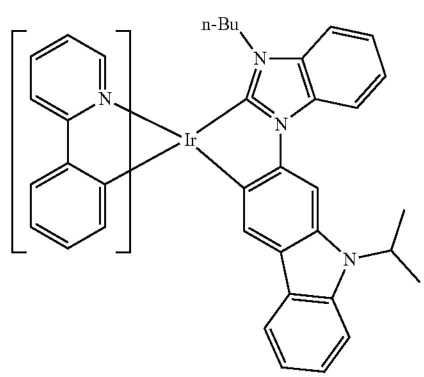
211
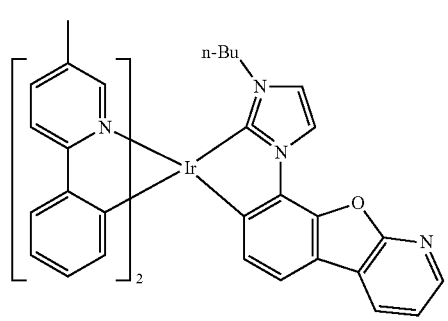

-continued
212
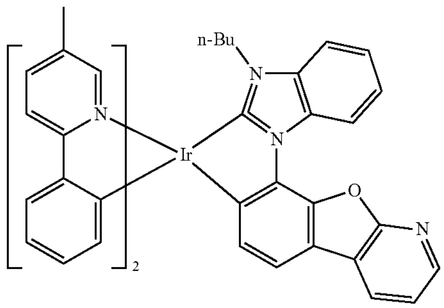
213
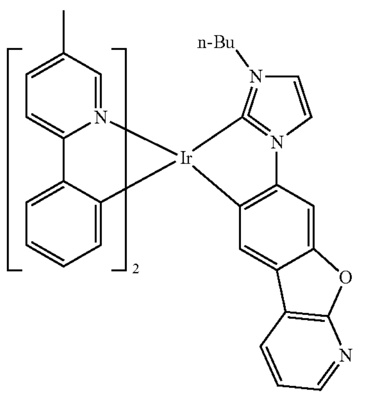
214
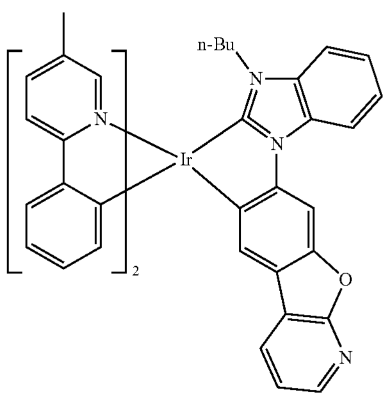
215
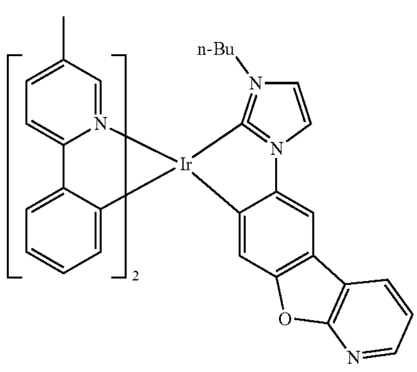
-continued
216
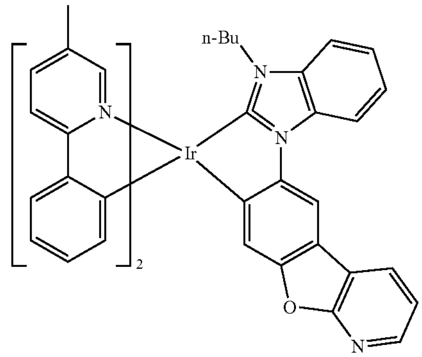
217
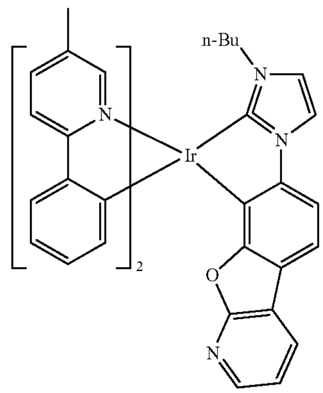
218
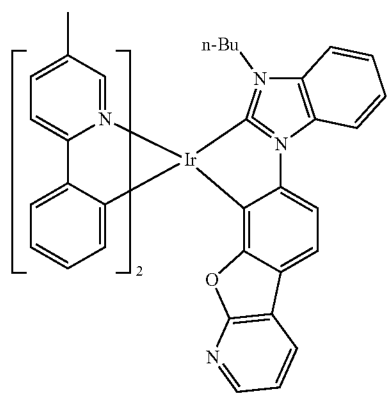
219
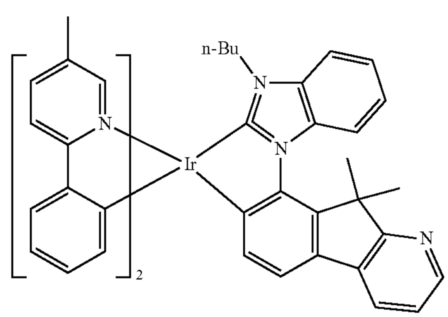

-continued
220
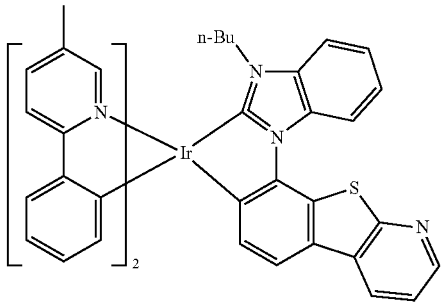
221
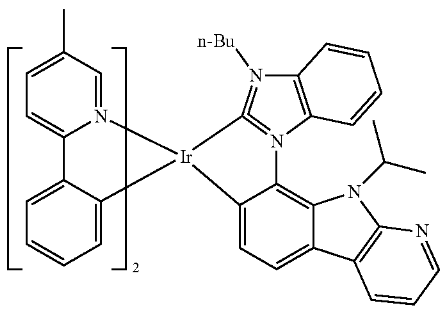
222
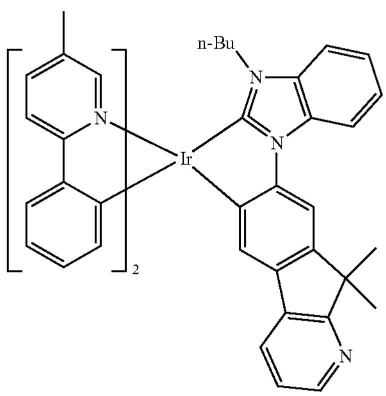
223
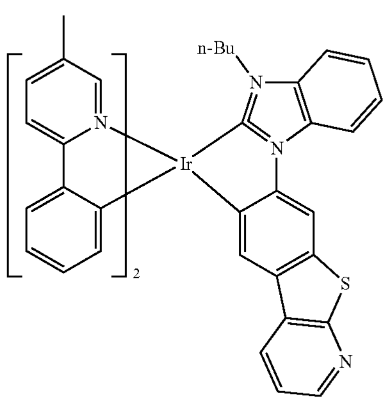
-continued
224
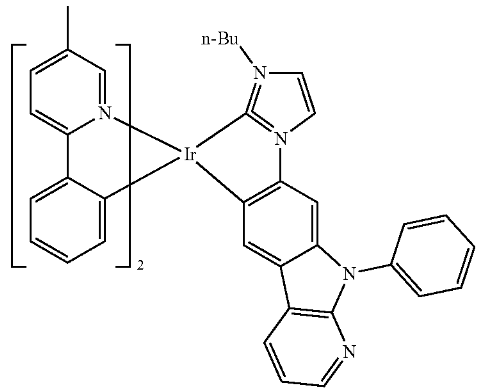
225
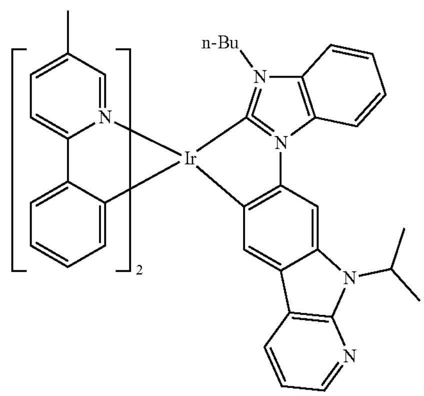
226
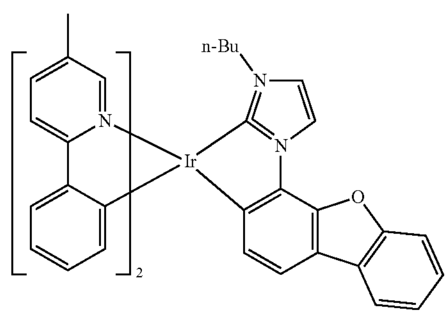
227
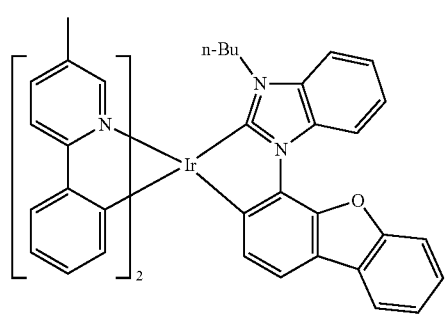

-continued
228
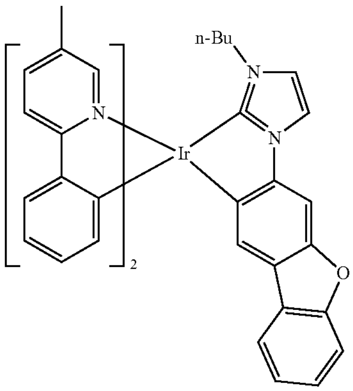
229
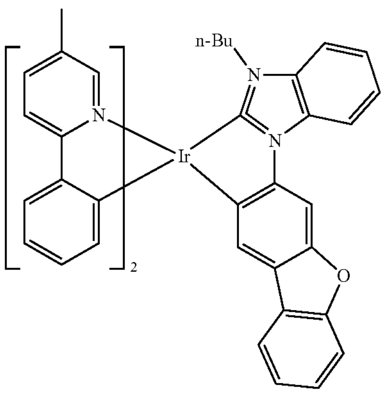
230
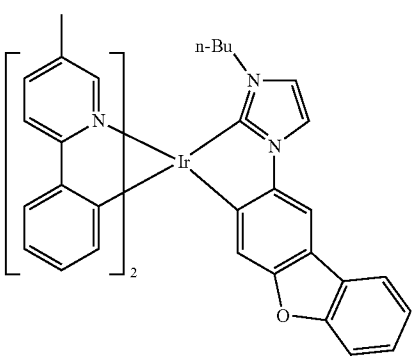
231
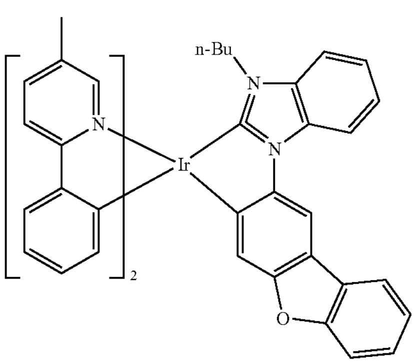
-continued
232
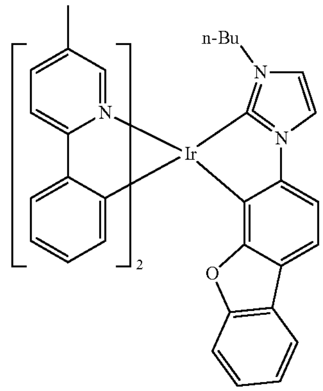
233
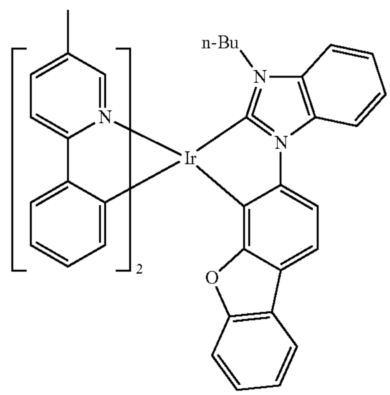
234
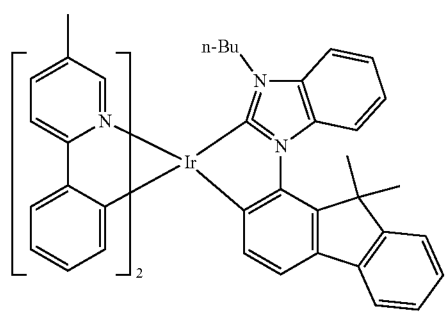
235
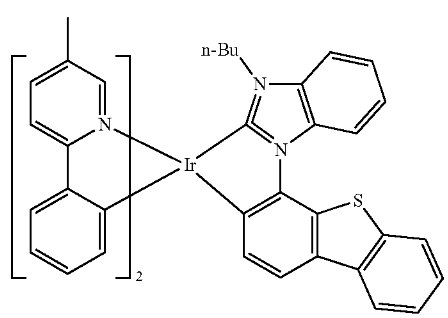

-continued
236
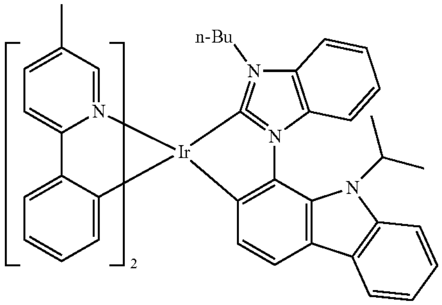
237
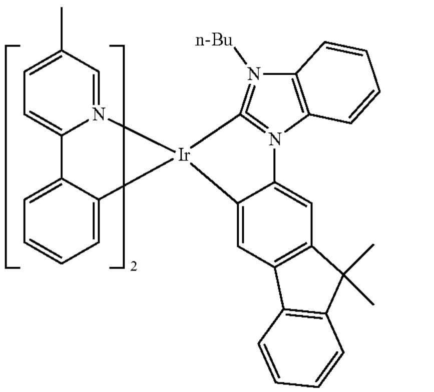
238
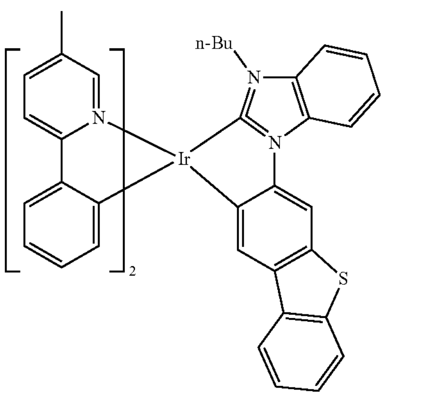
239
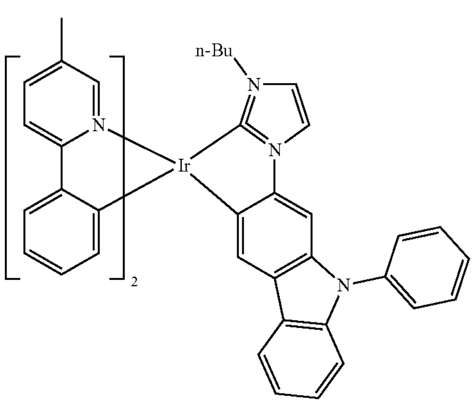
-continued
240
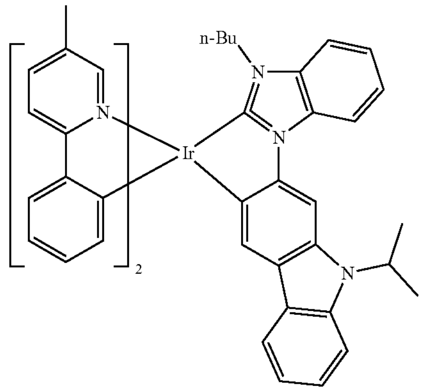
241
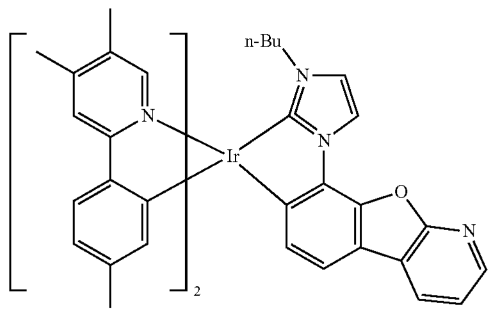
242
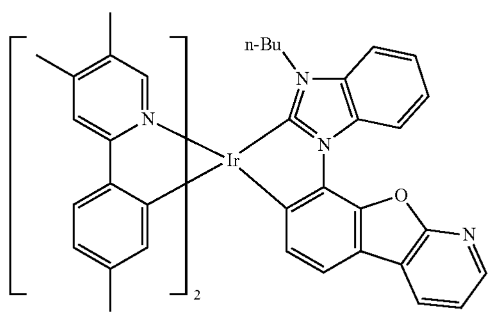
243
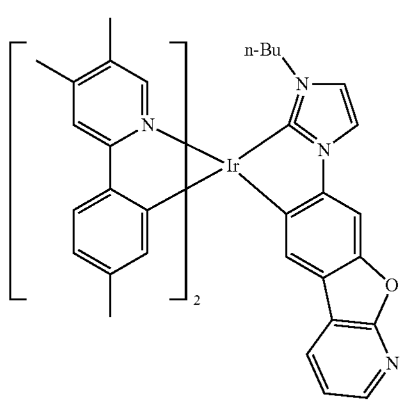

-continued
244
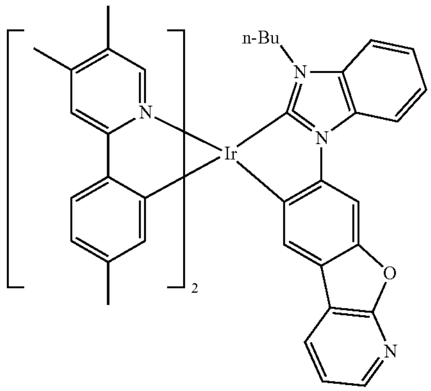
245
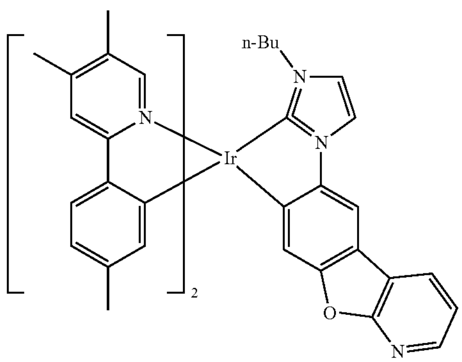
246
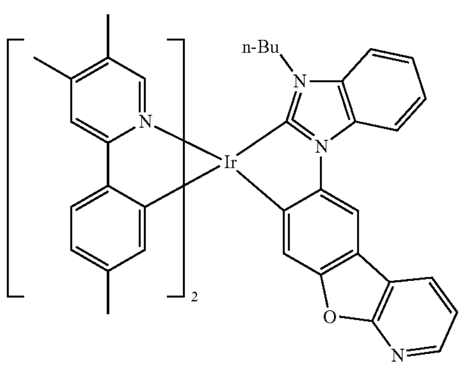
247
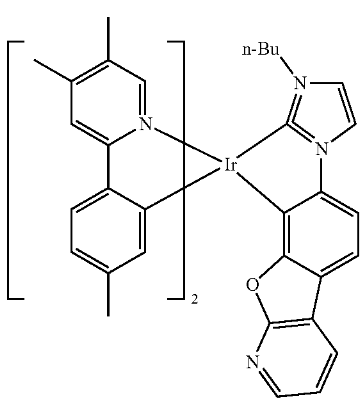
-continued
248
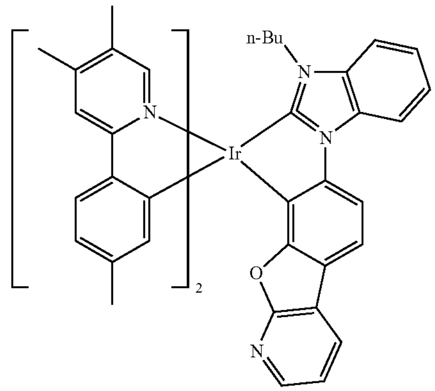
249
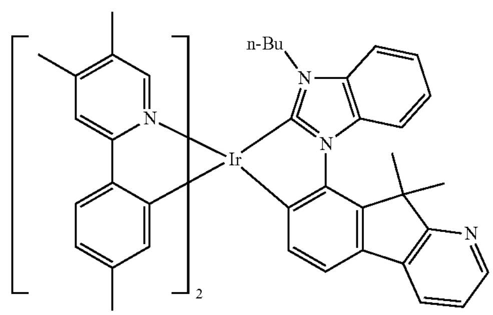
250
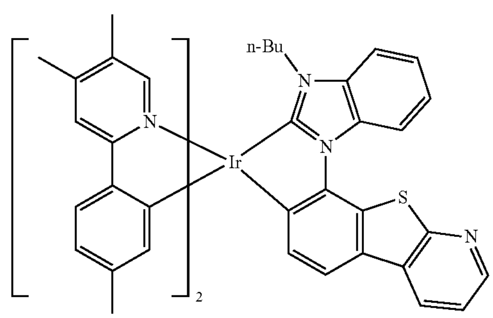
251
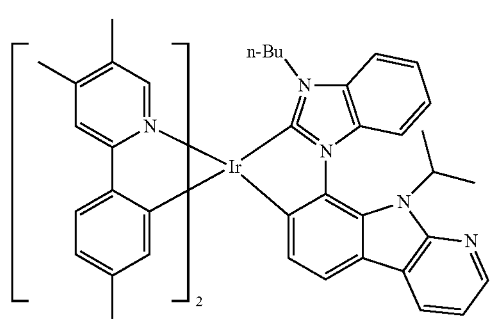

-continued
252
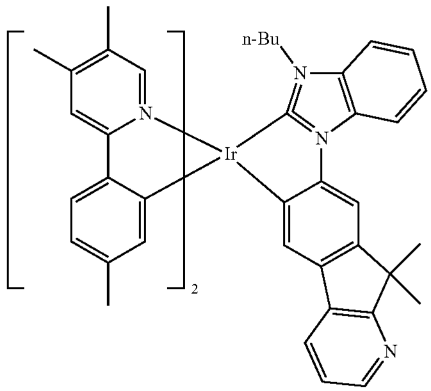
253
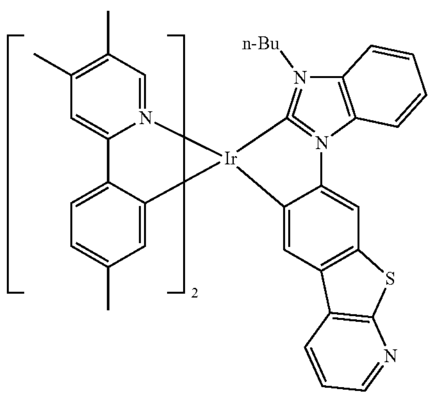
254
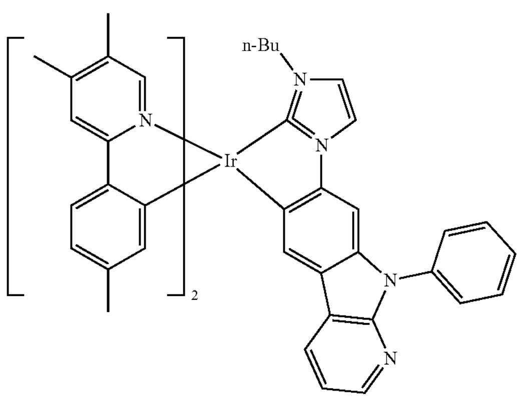
255
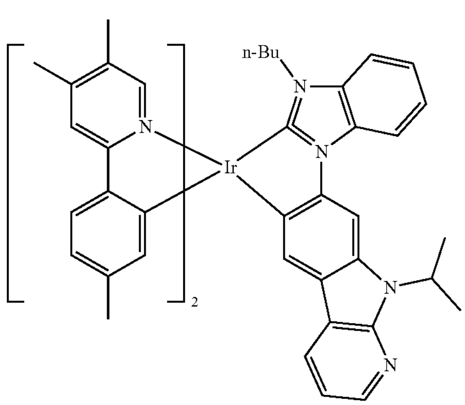
-continued
256
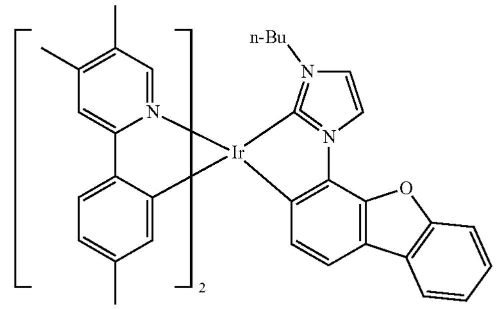
257
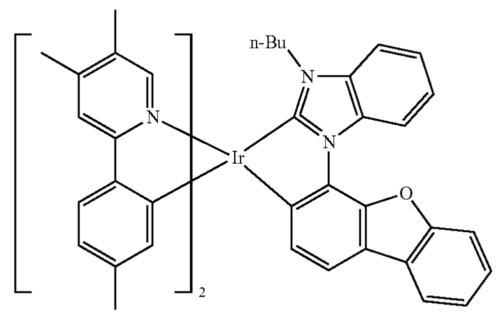
258
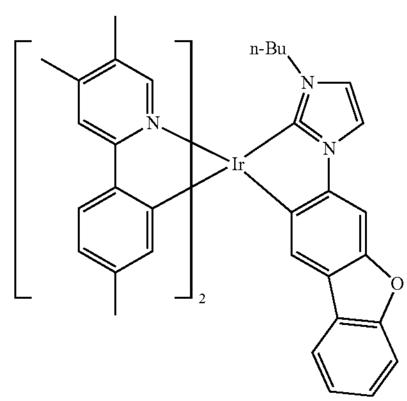
259
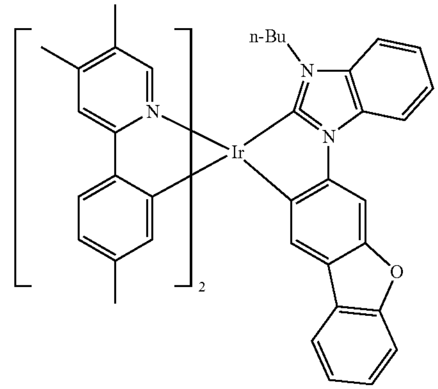

-continued
260
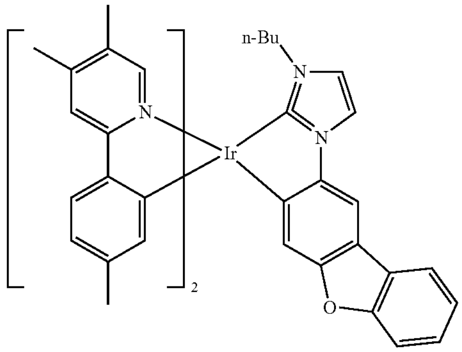
261
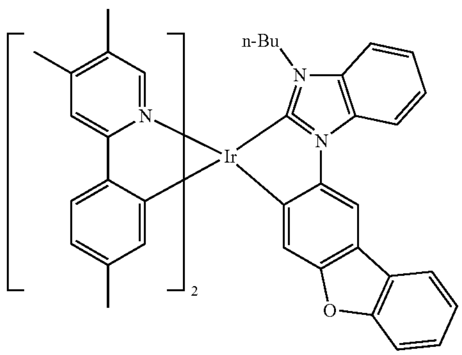
262
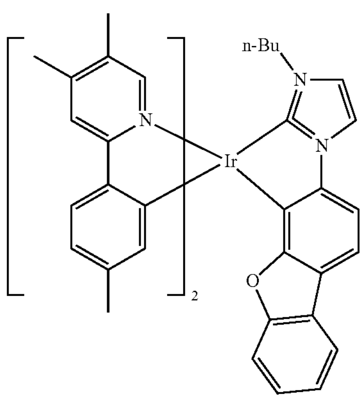
263
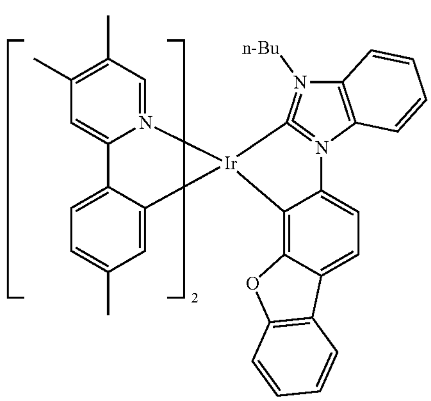
-continued
264
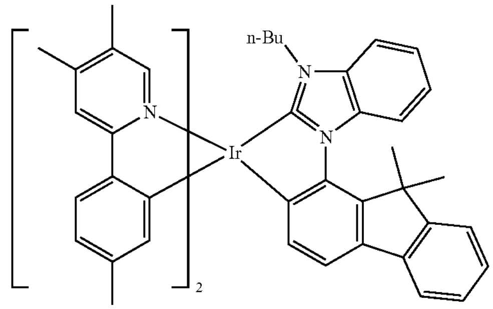
265
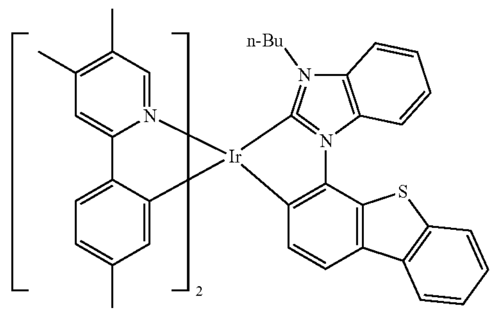
266
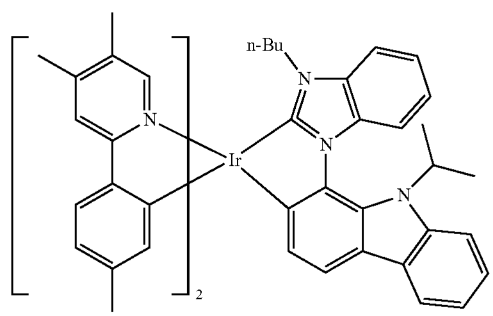
267
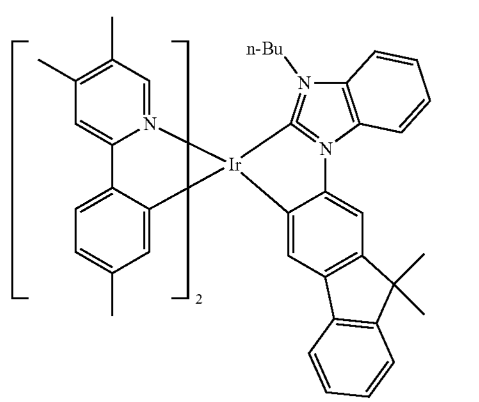

-continued
268
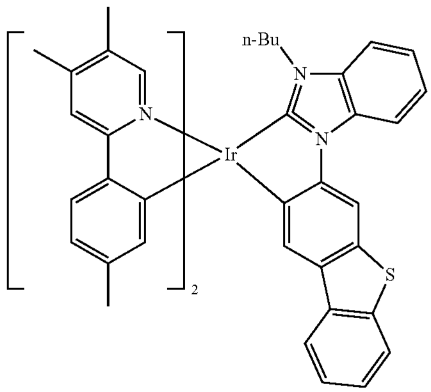
269
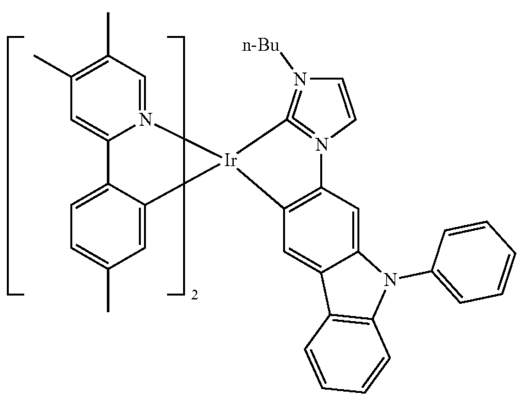
270
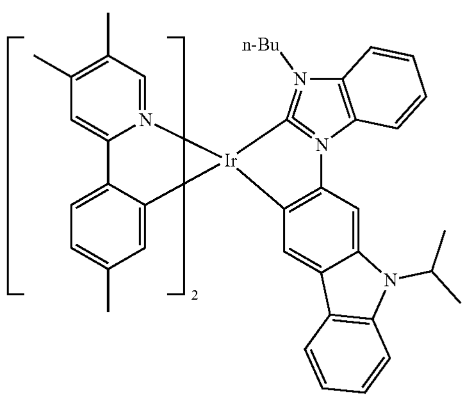
271
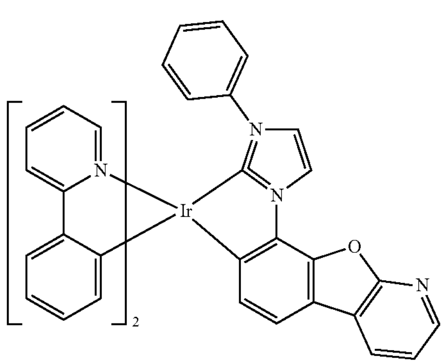
-continued
272
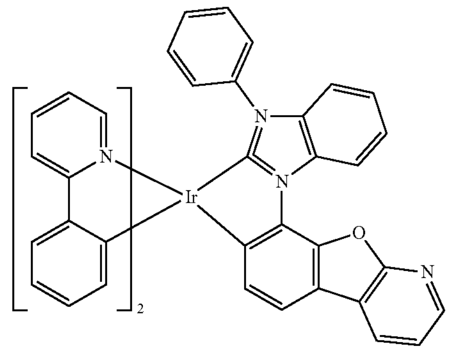
273
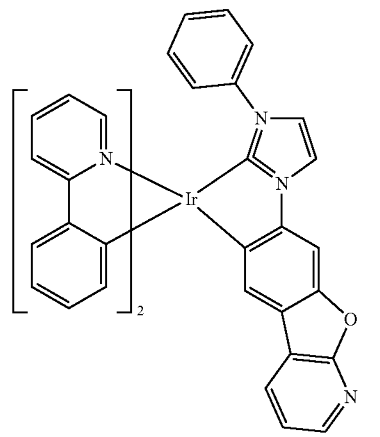
274
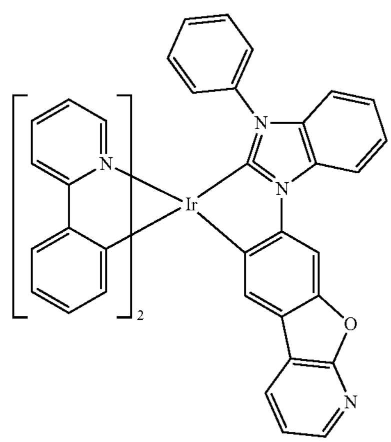
274
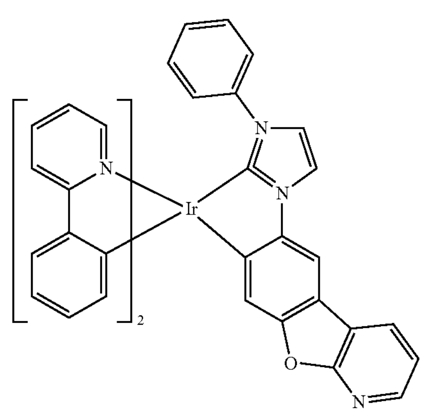

-continued
276
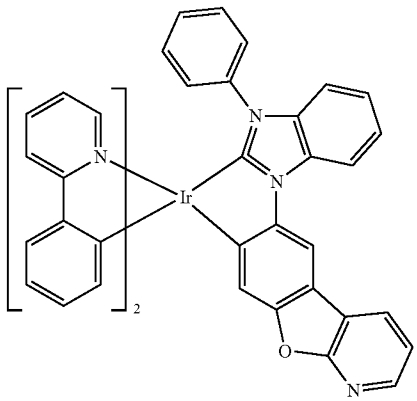
277
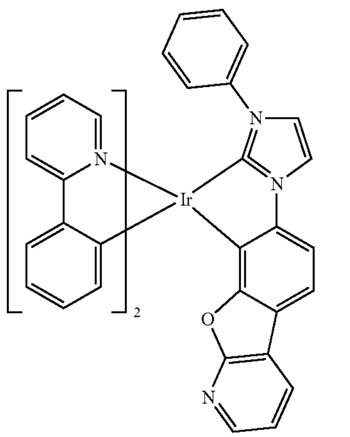
278
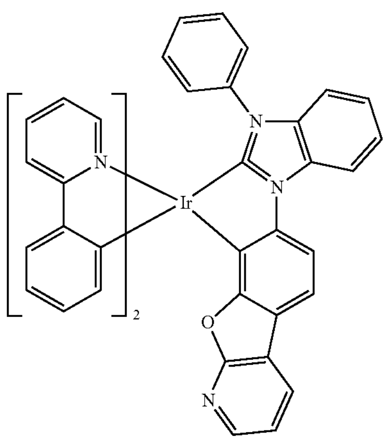
279
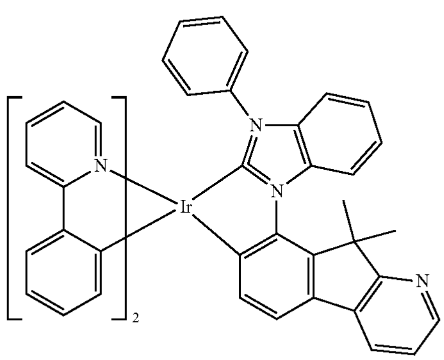
-continued
280
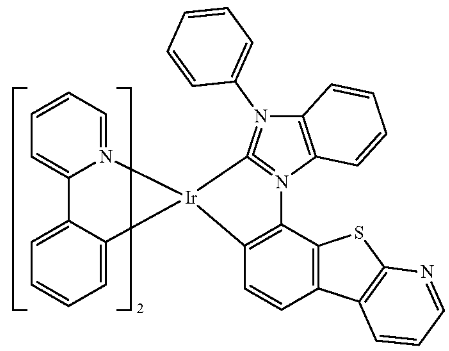
281
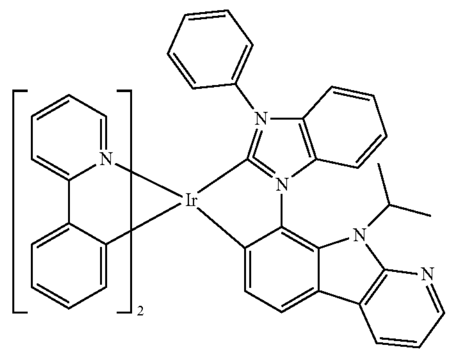
282
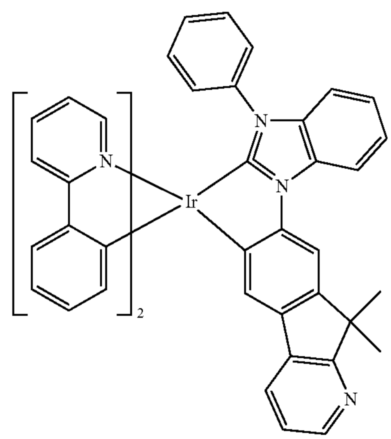
283
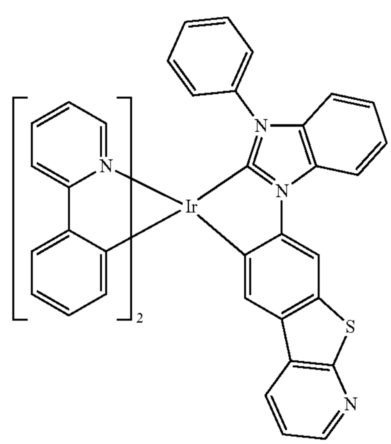

-continued
284
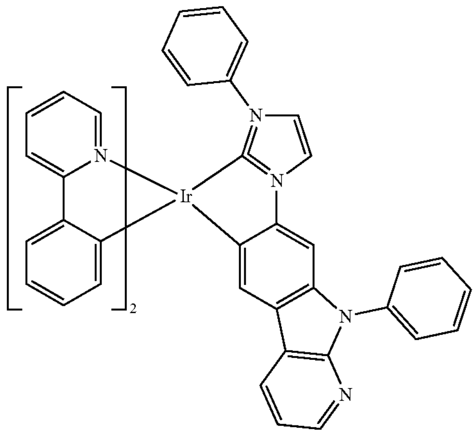
285
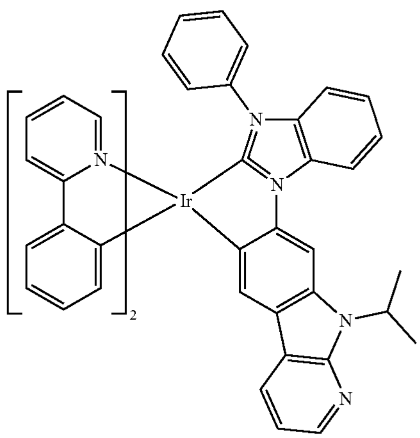
286
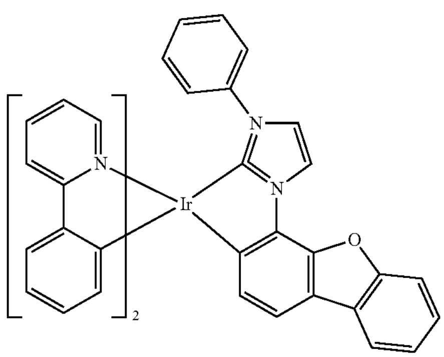
287
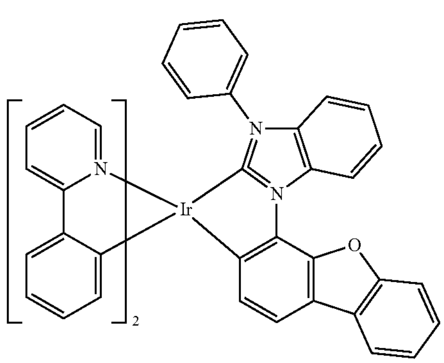
-continued
288
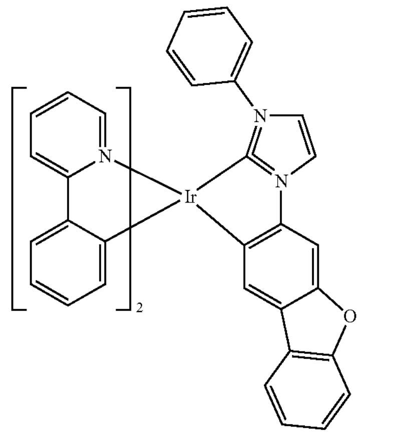
289
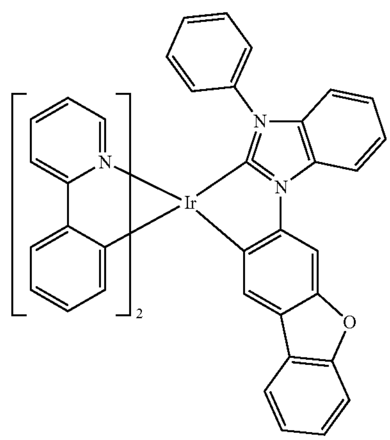
290
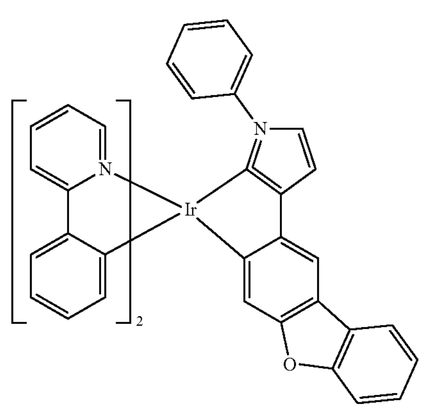

-continued
291
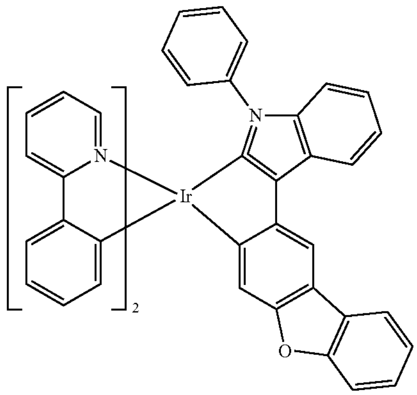
292
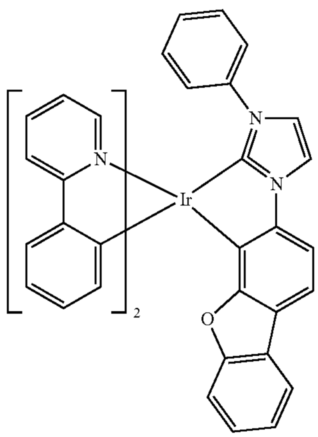
293
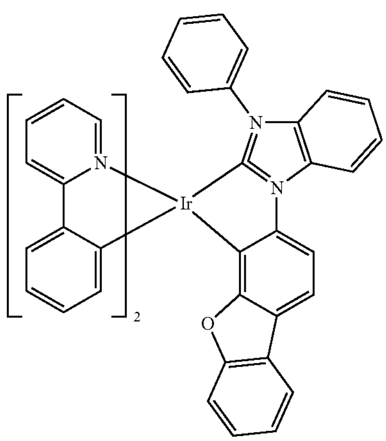
294
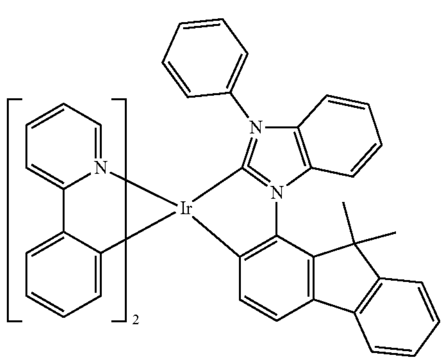
-continued
295
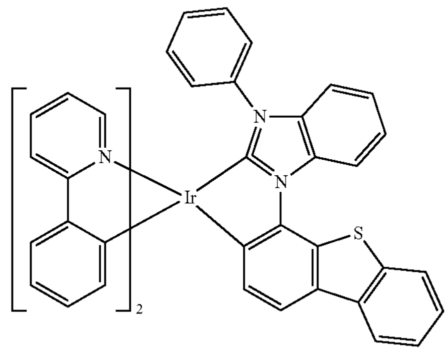
296
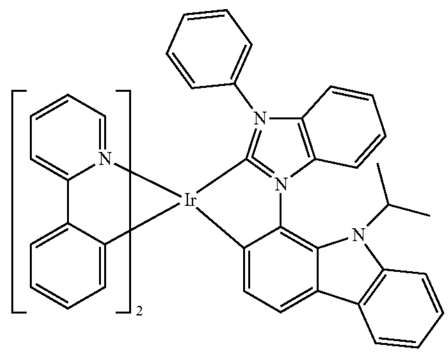
297
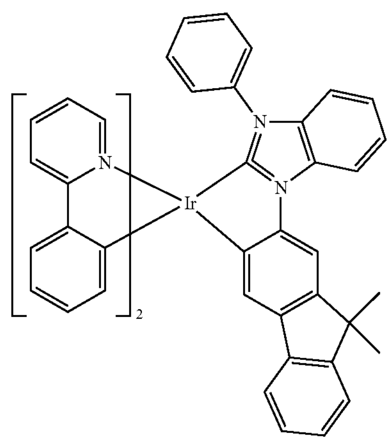
298
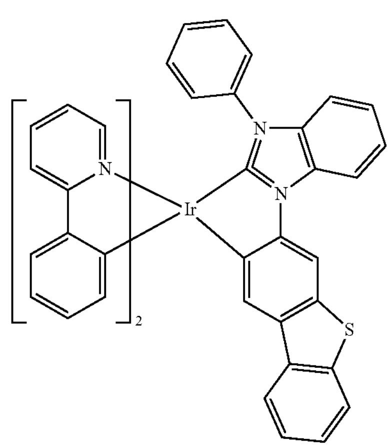

-continued
299
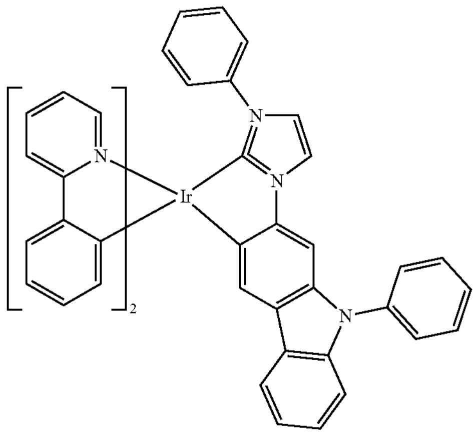
300
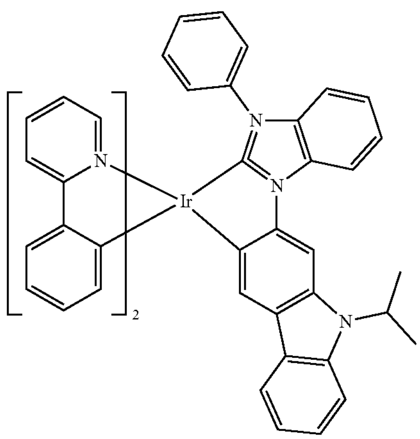
301
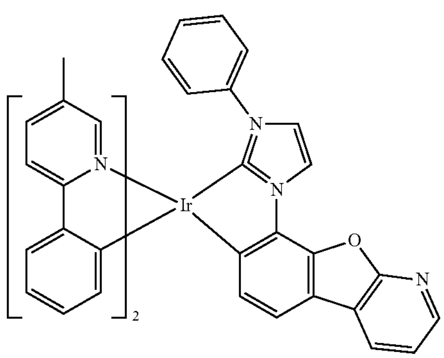
302
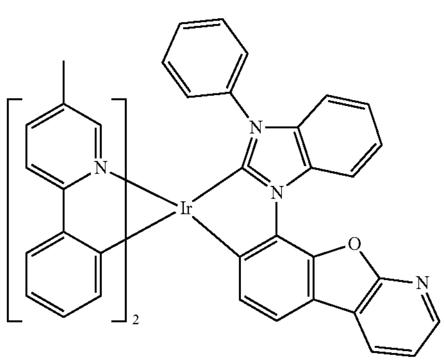
-continued
303
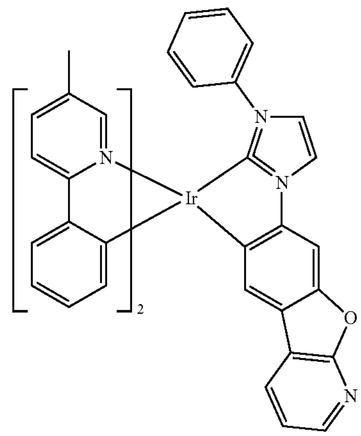
304
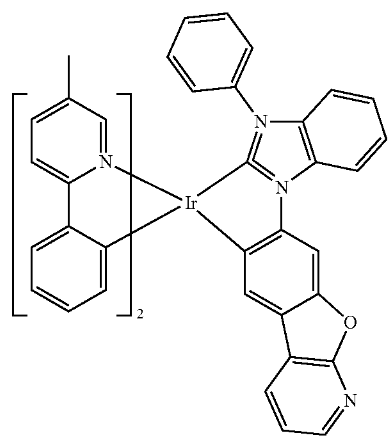
305
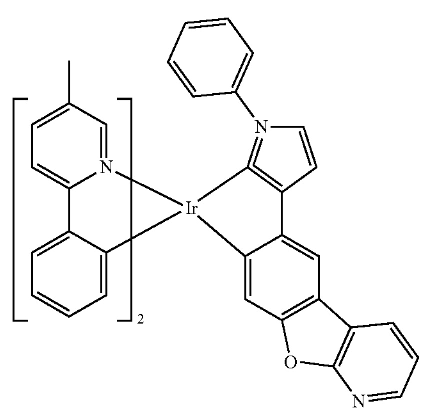

-continued
306
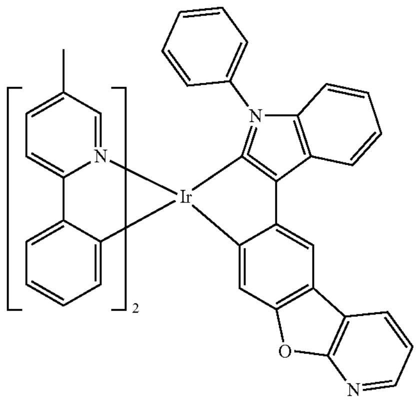
307
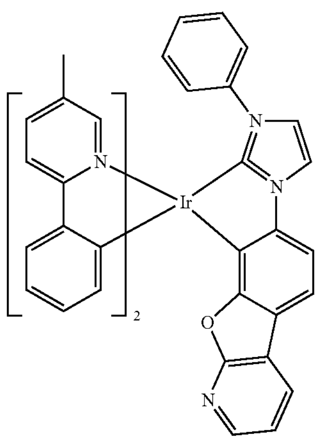
308
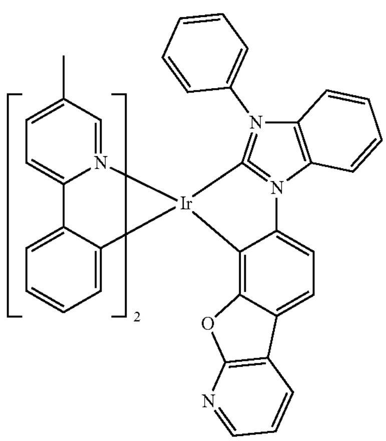
309
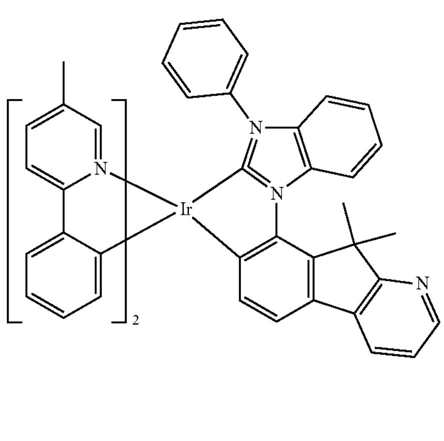
-continued
310
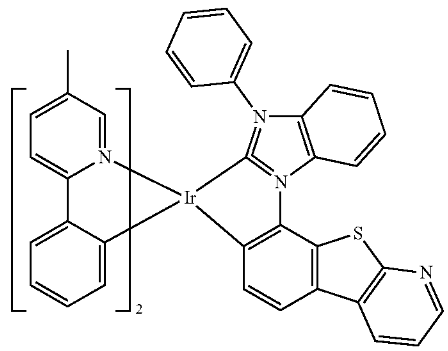
311
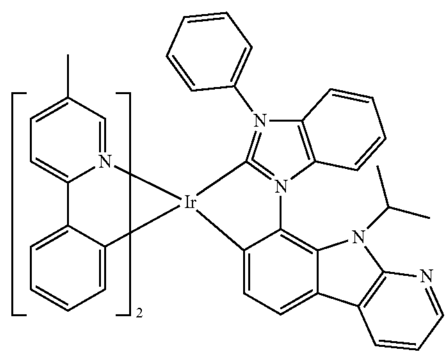
312
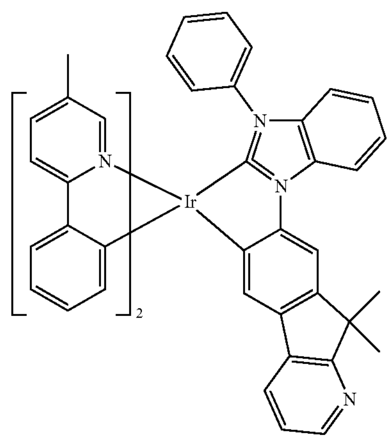
313
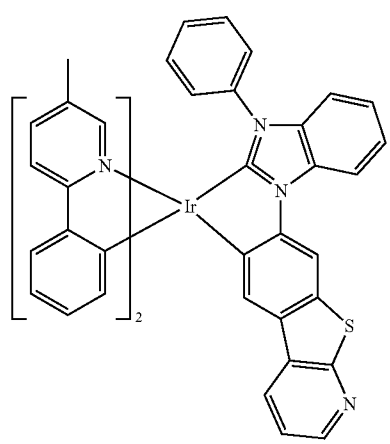

-continued
314
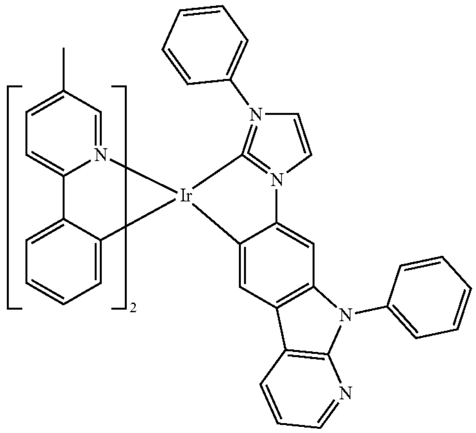
315
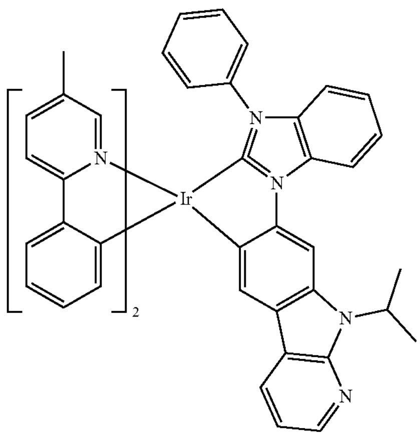
316
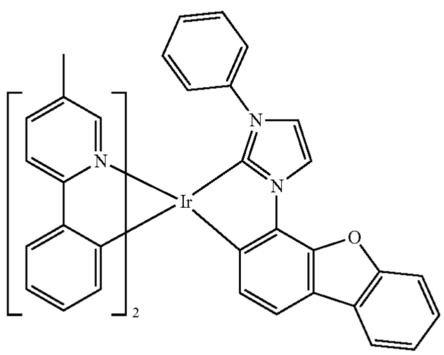
317
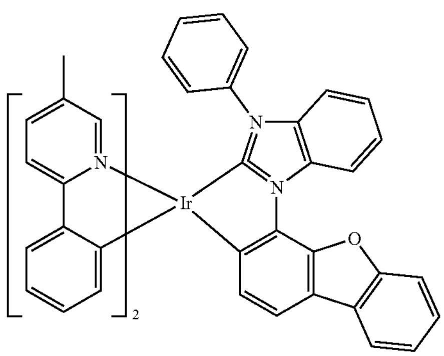
-continued
318
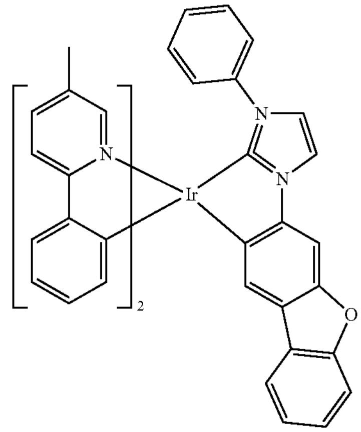
319
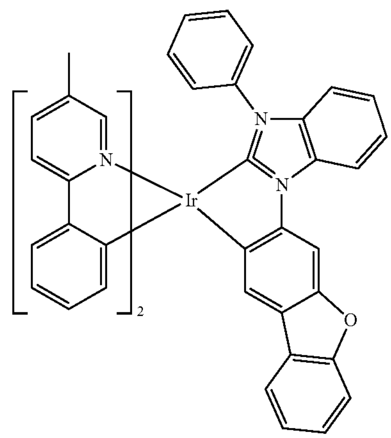
320
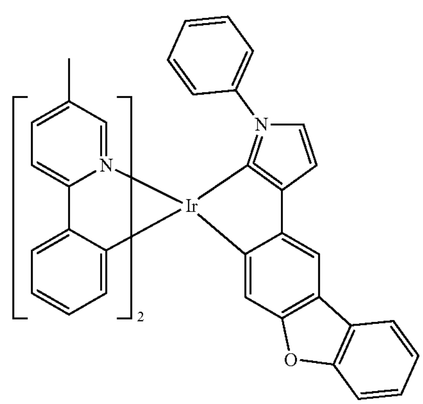

-continued
321
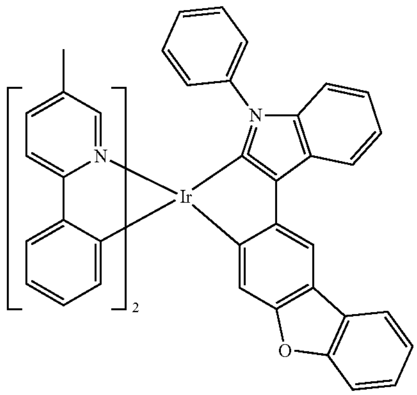
322
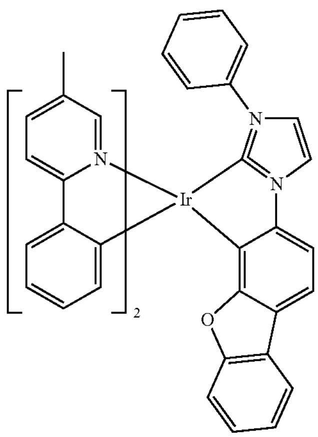
323
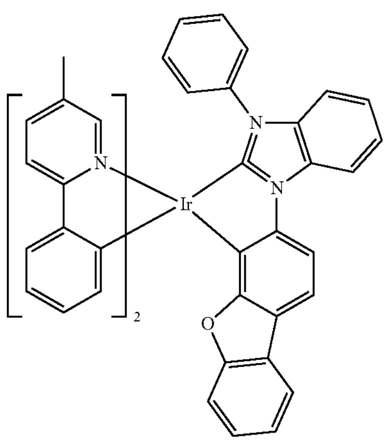
324
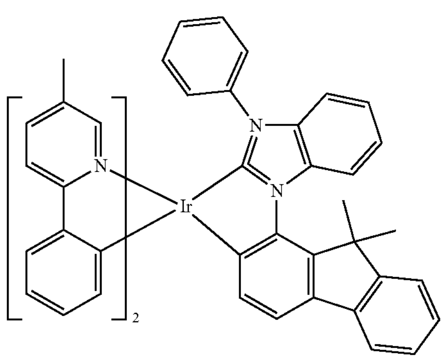
-continued
325
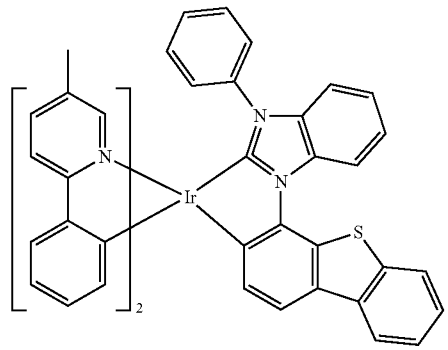
326
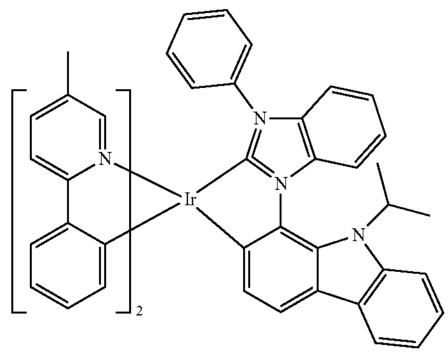
327
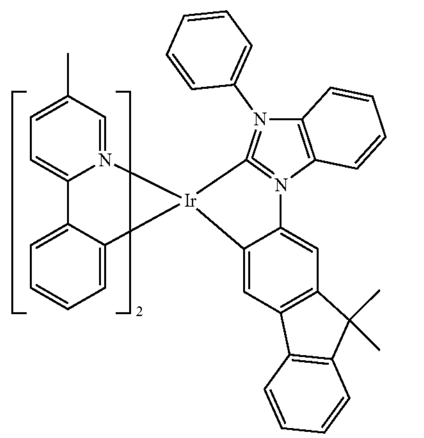
328
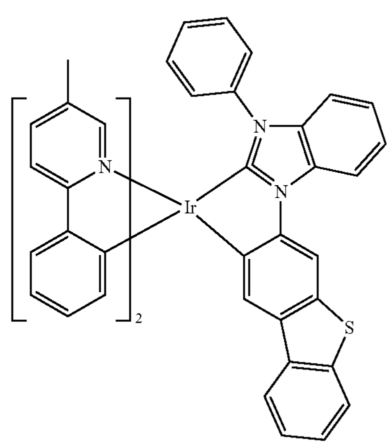

-continued
329
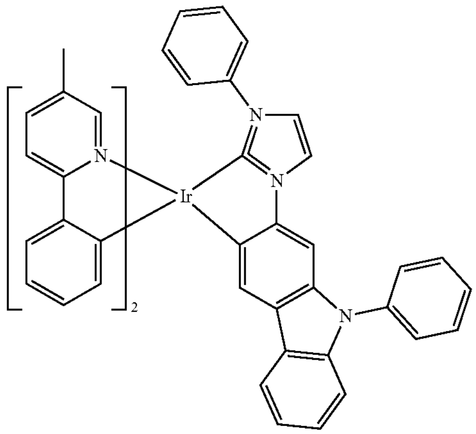
330
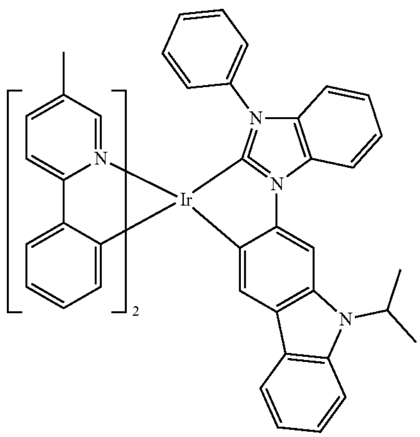
331
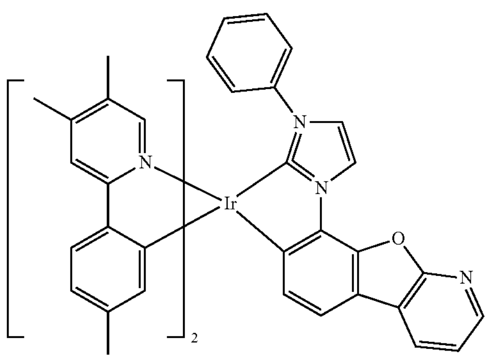
332
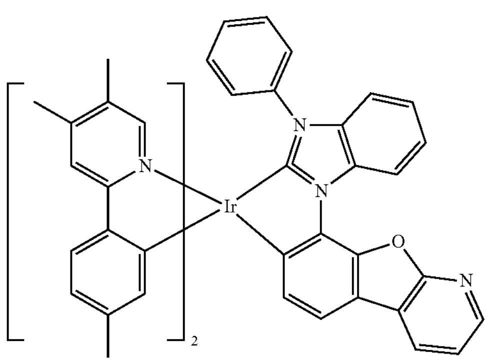
-continued
333
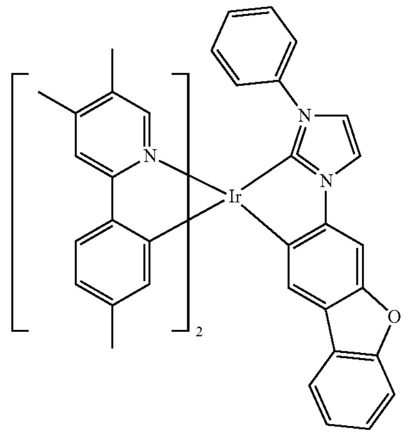
334
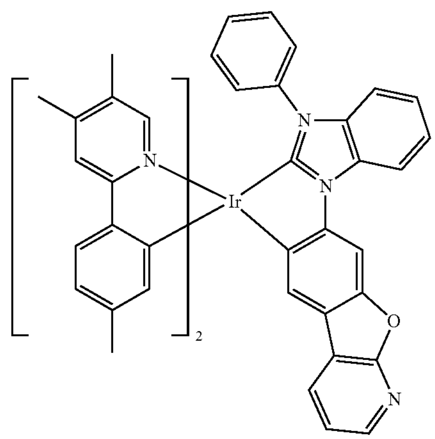
335
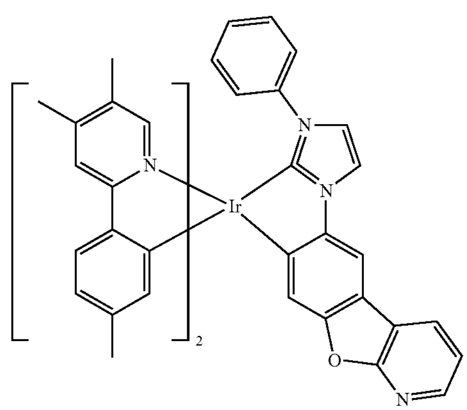

-continued
336
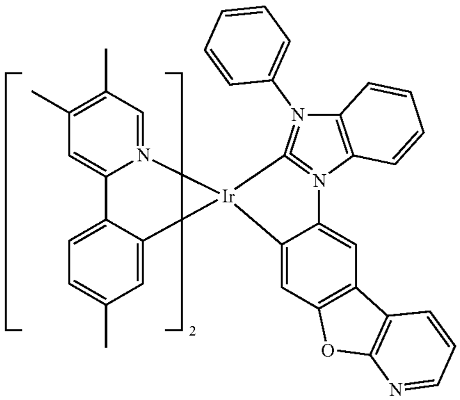
337
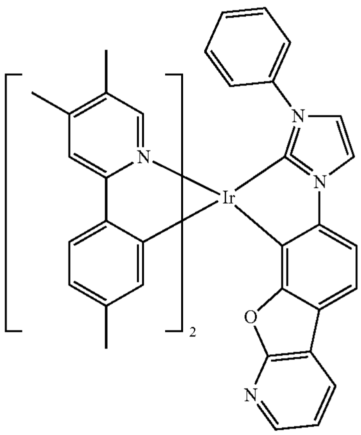
338
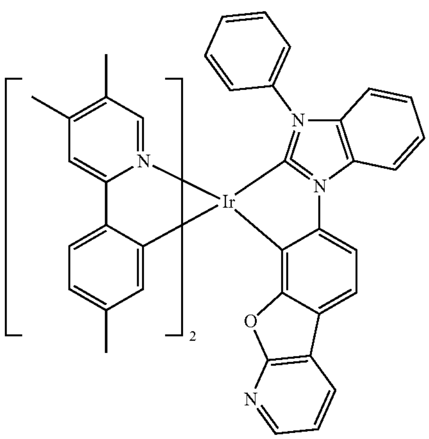
339
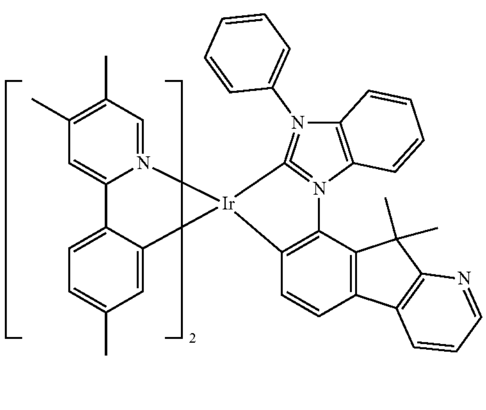
-continued
340
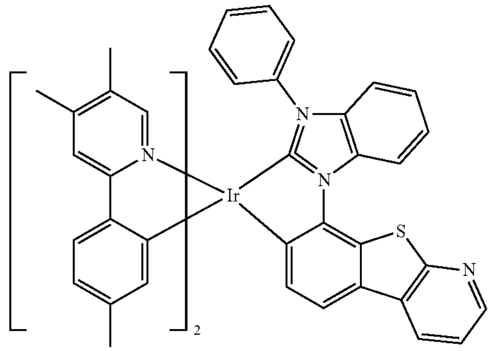
341
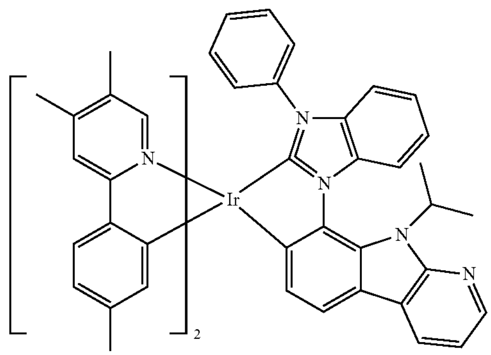
342
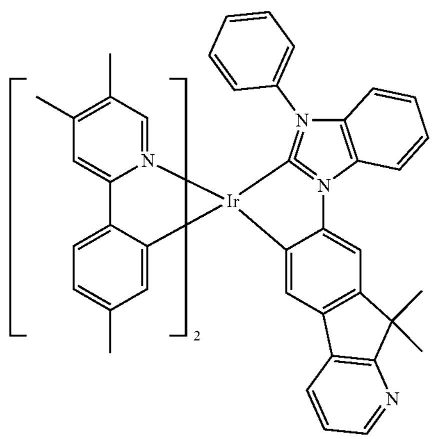
343
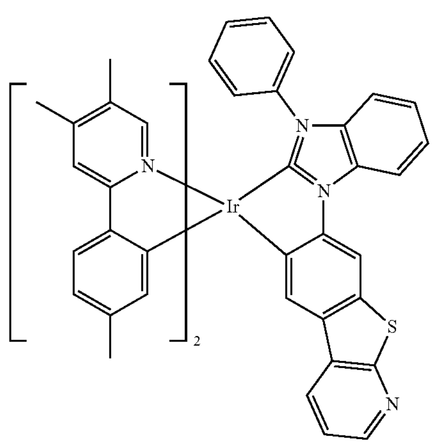

-continued
344
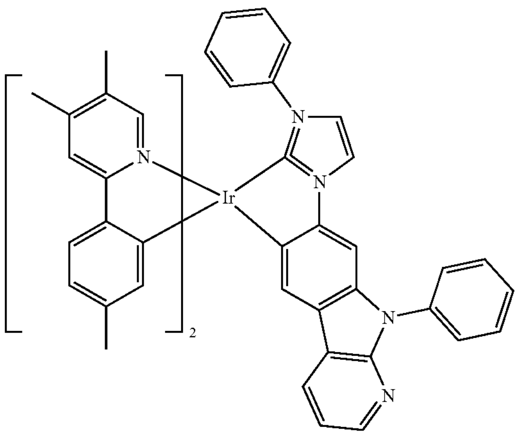
345
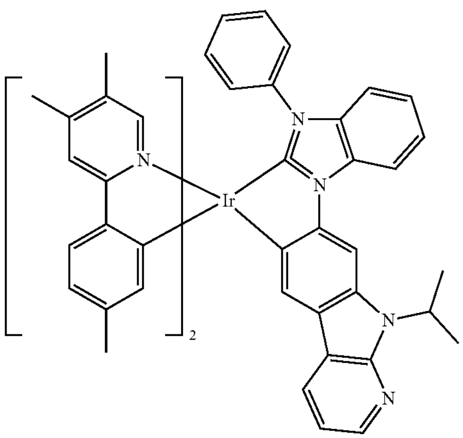
346
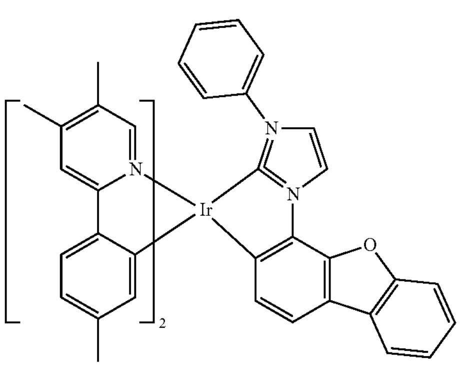
-continued
347
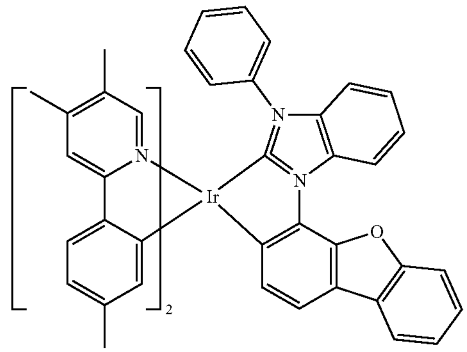
348
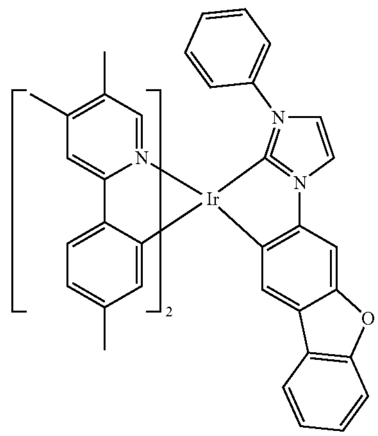
349
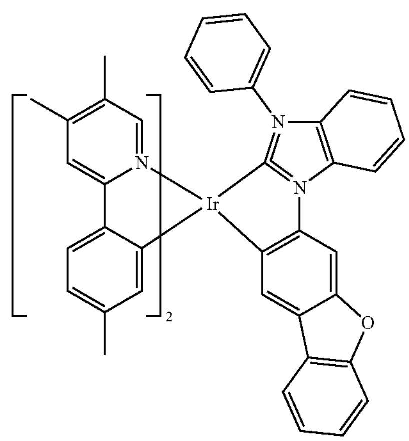
350
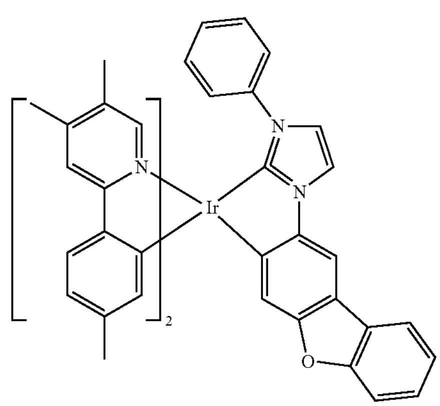

-continued
351
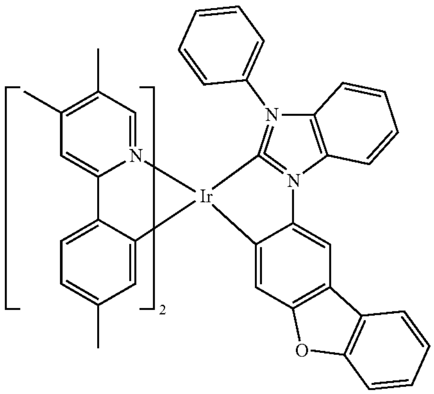
352
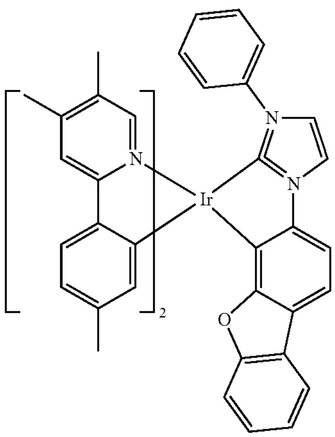
353
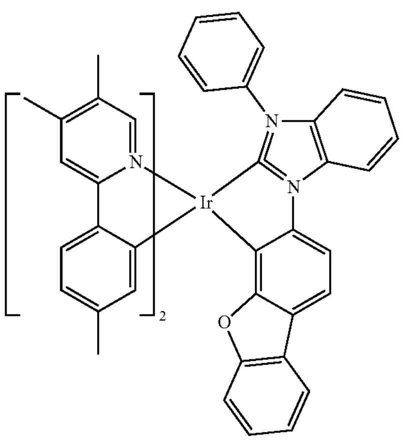
354
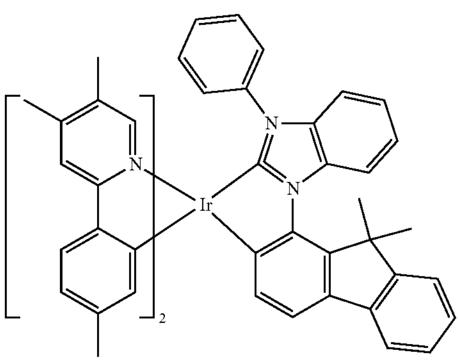
-continued
355
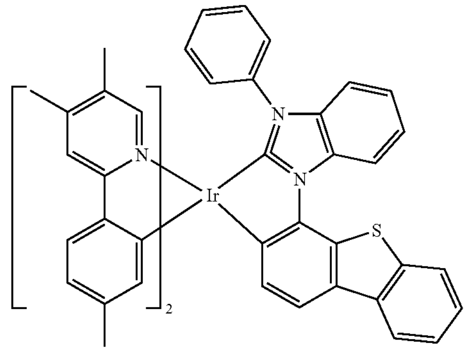
356
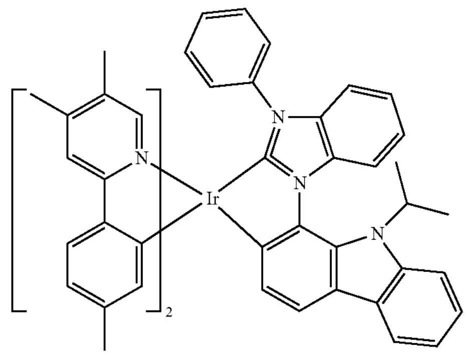
357
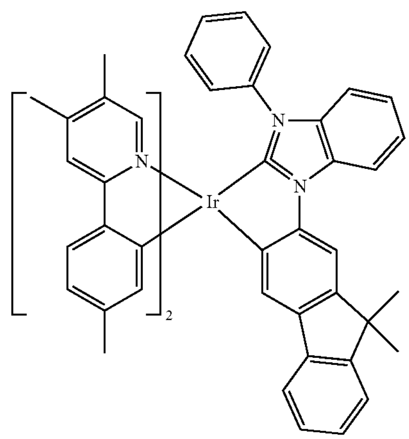
358
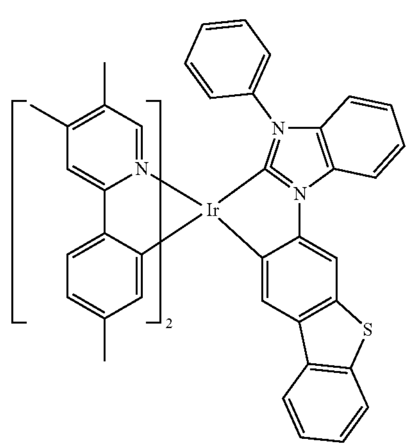

-continued
359
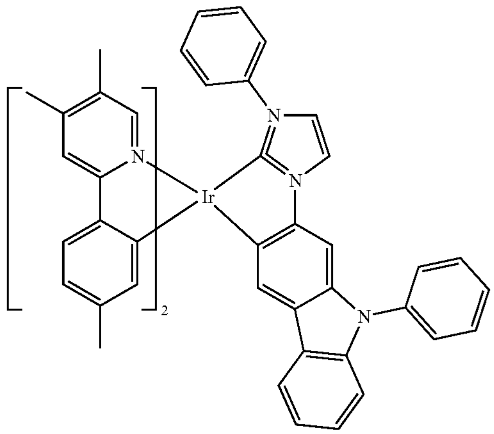
360
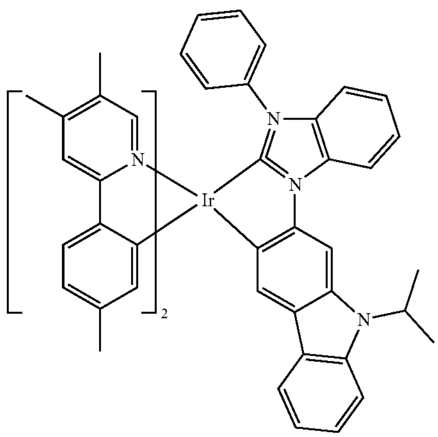
361
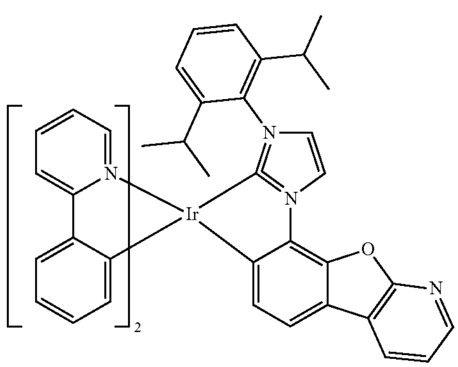
362
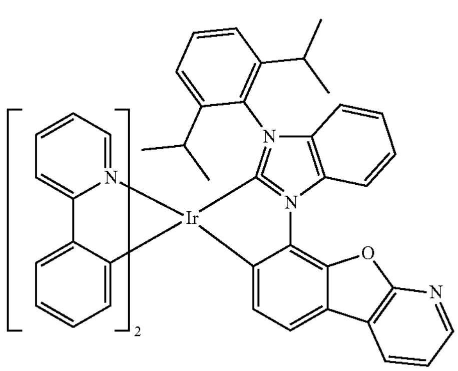
-continued
363
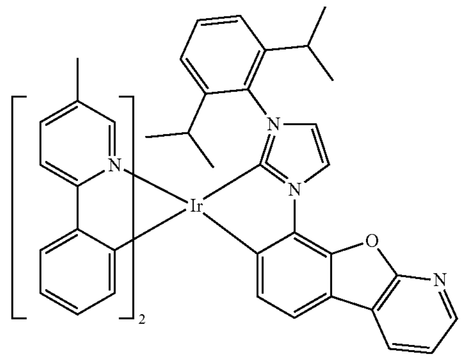
364
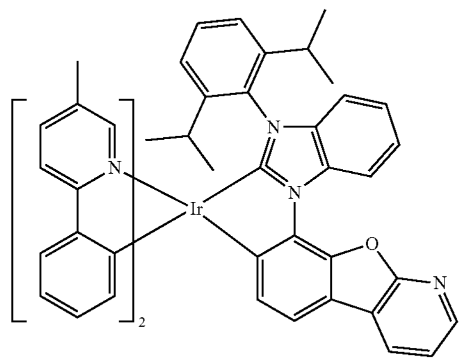
365
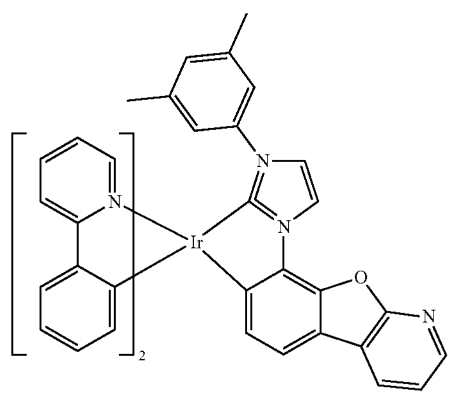
+
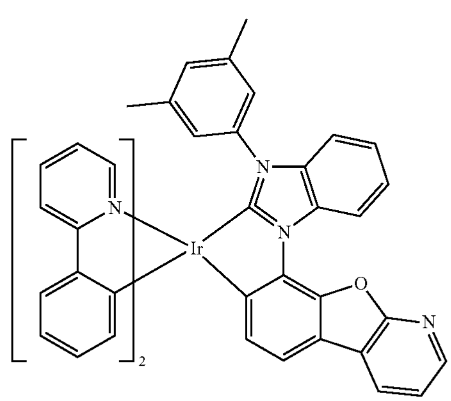

-continued
367
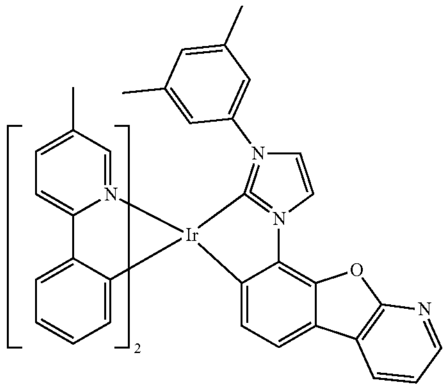
368
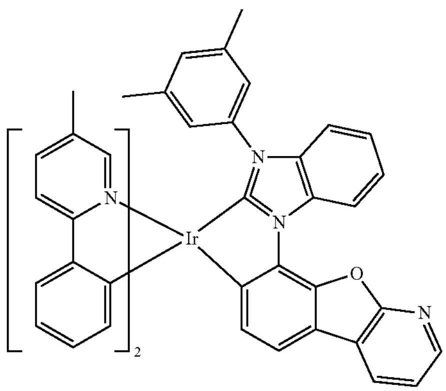
369
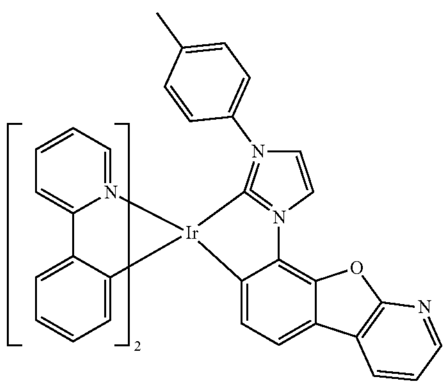
370
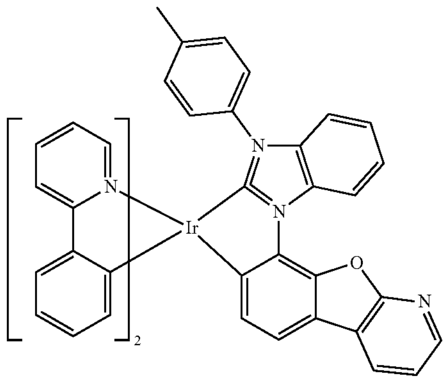
-continued
371
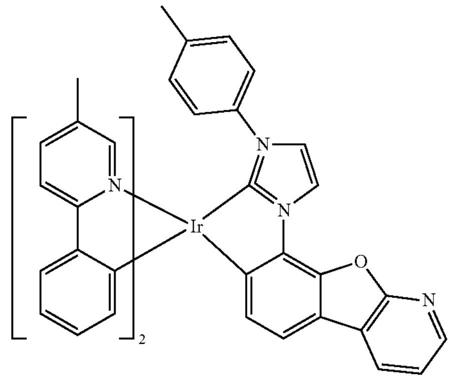
372
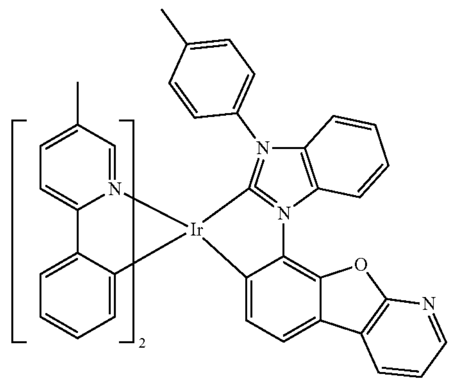
373
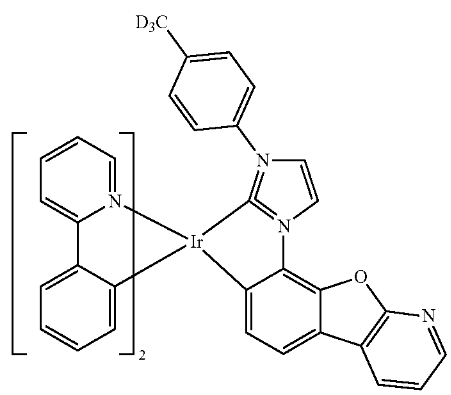
374
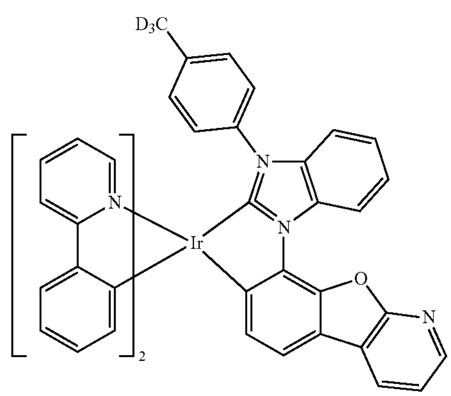

-continued
375
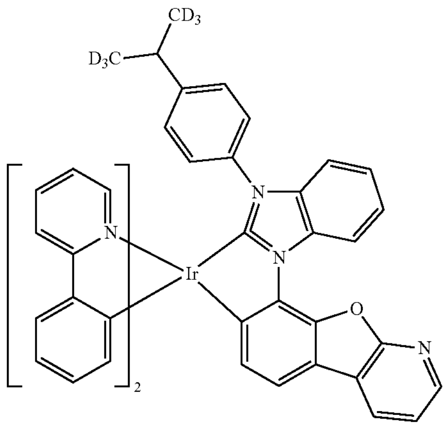
376
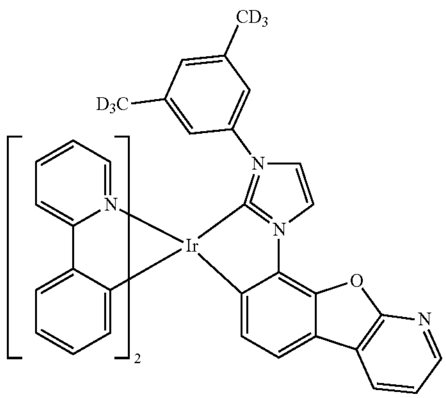
377
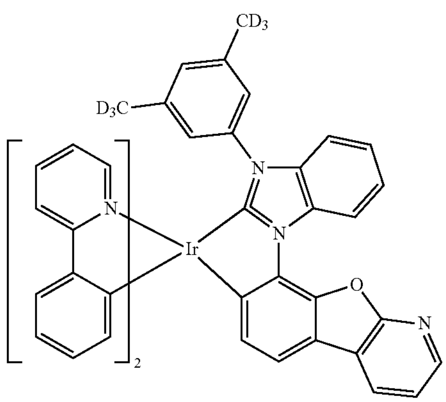
378
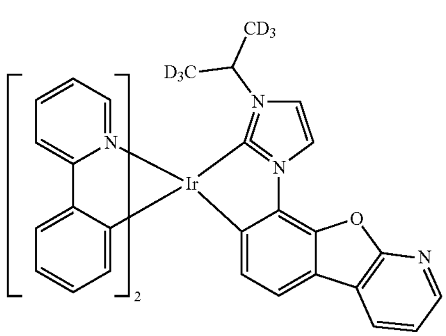
-continued
379
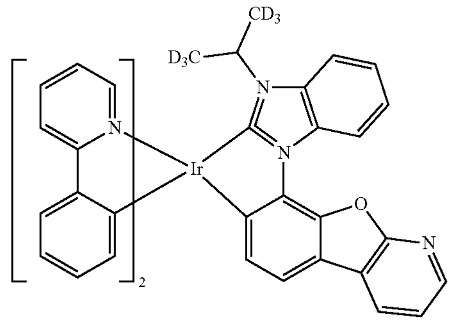
380
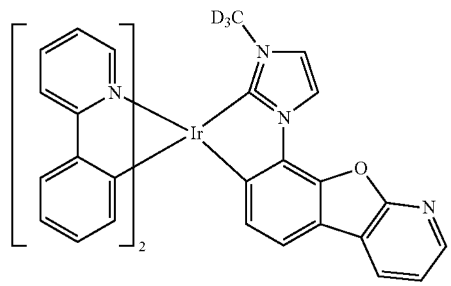
381
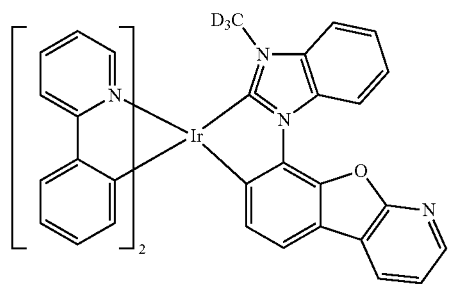
382
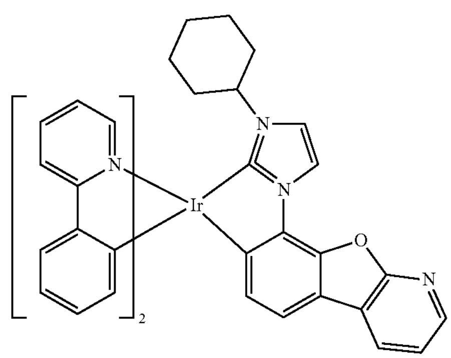
383
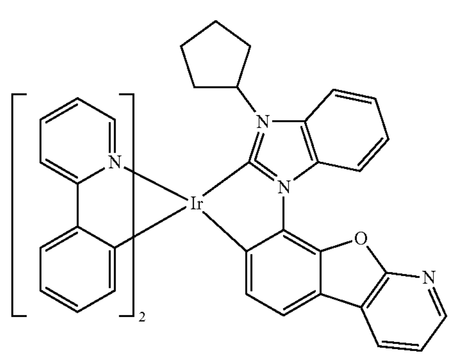

-continued
384
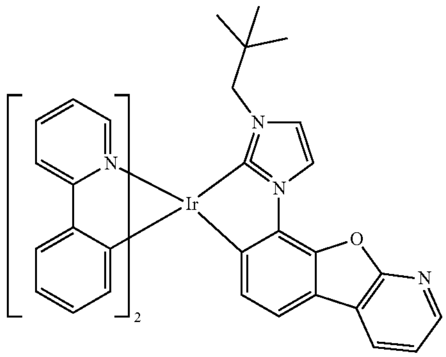
385
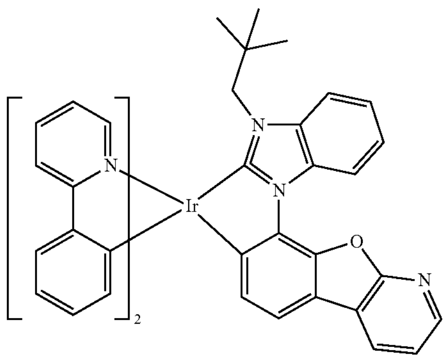
386
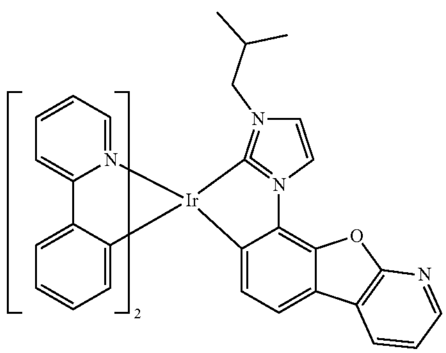
387
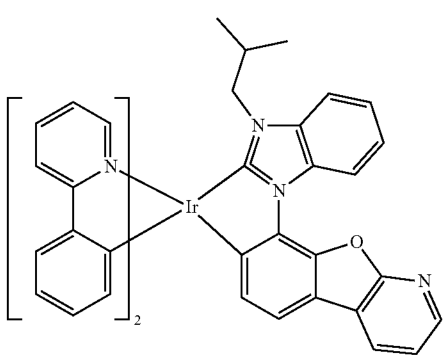
-continued
388
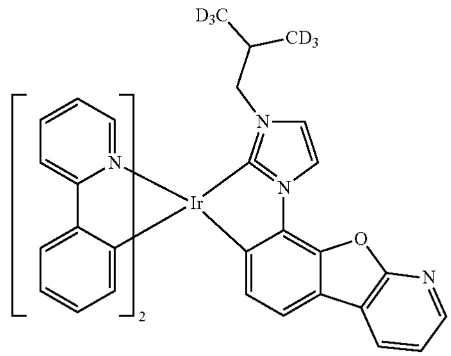
389
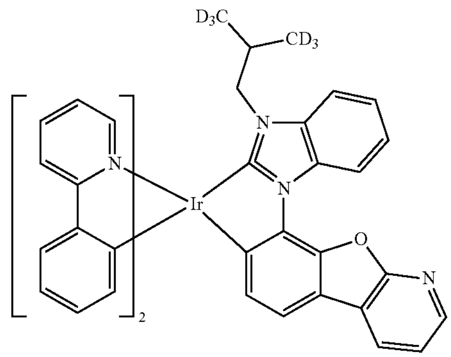
390
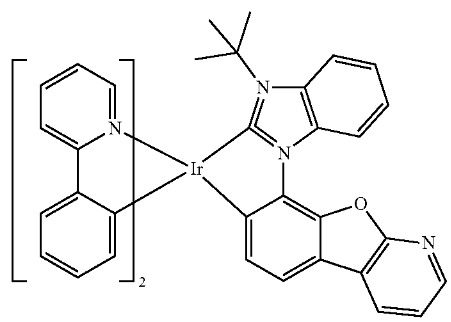
391
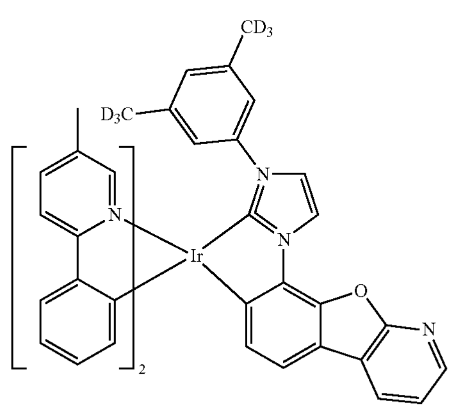

-continued
392
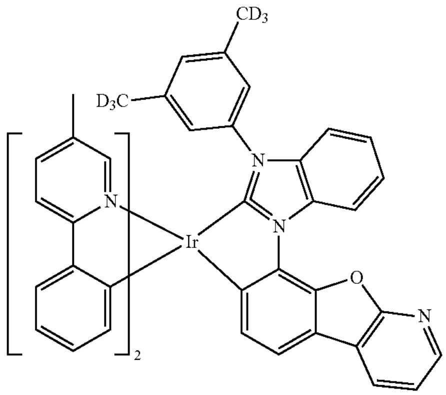
393
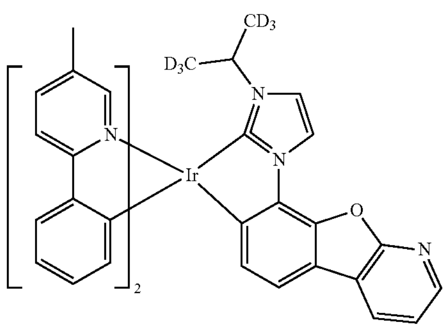
394
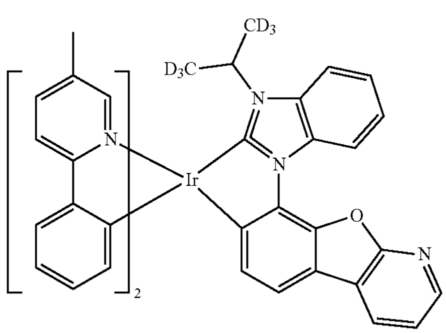
395
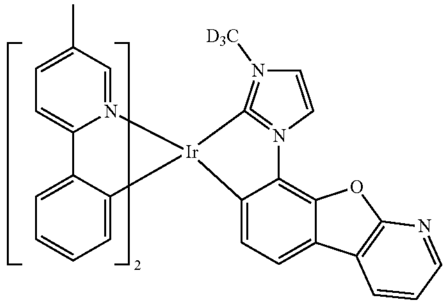
-continued
396
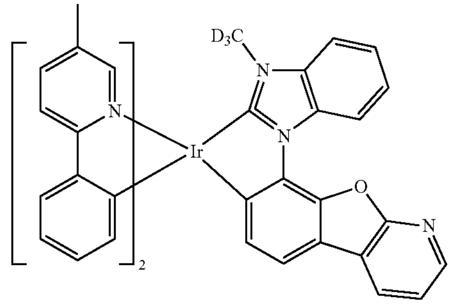
397
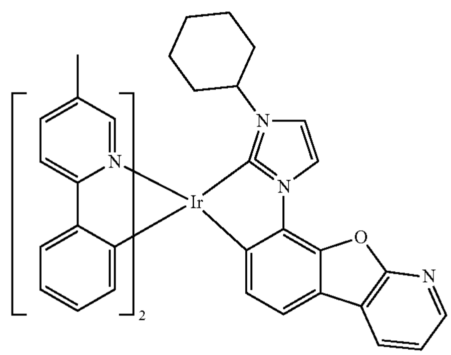
398
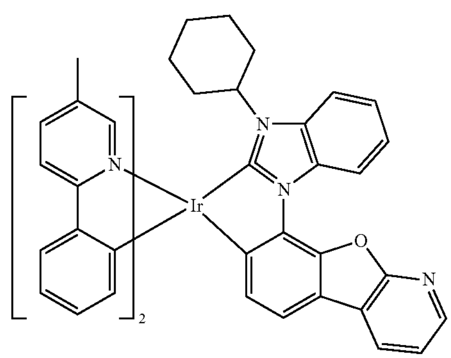
399
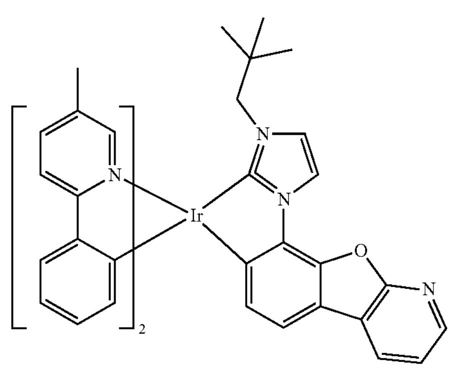

-continued
400
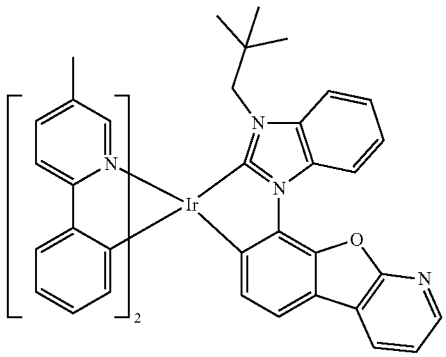
401
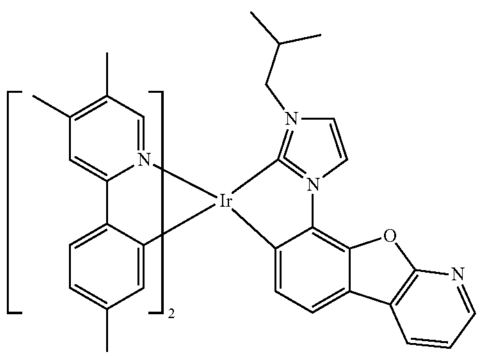
402
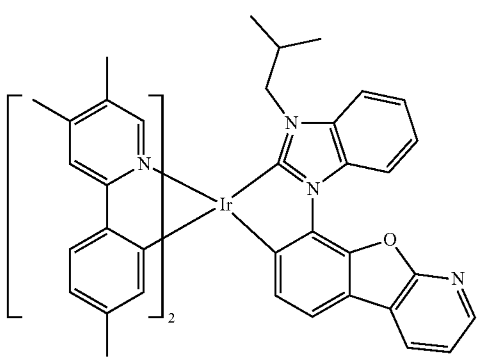
403
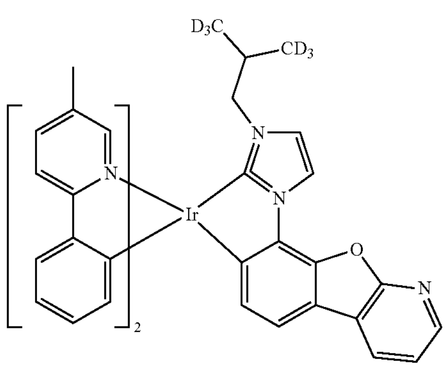
-continued
404
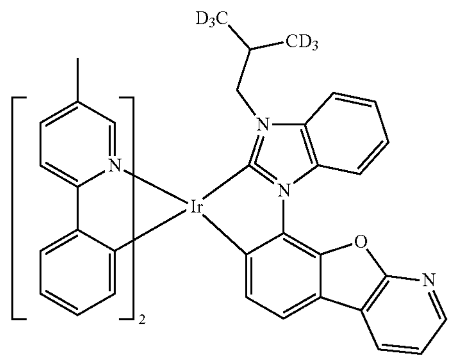
405
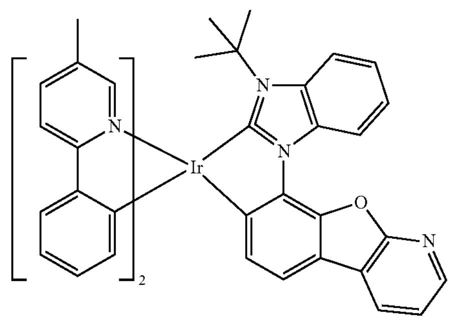
406
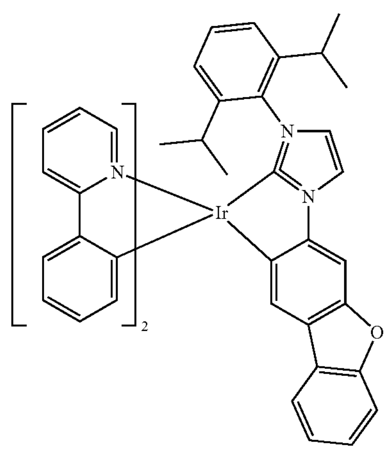
407
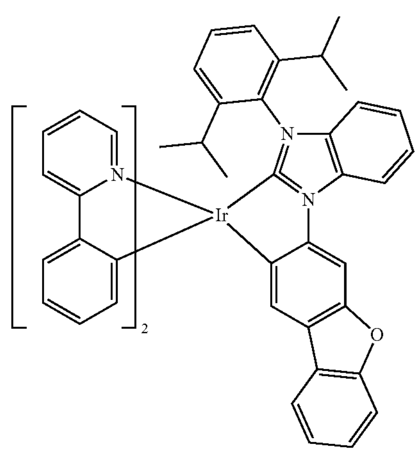

-continued
408
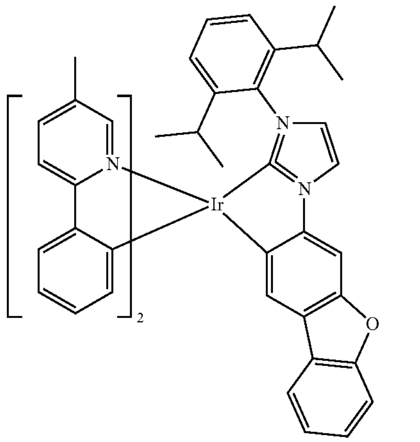
409
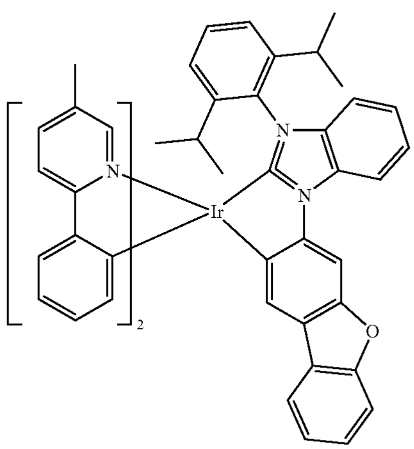
410
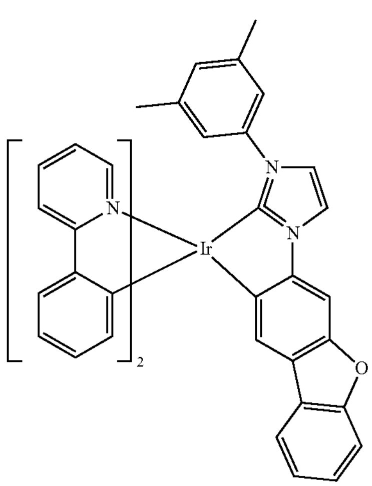
-continued
411
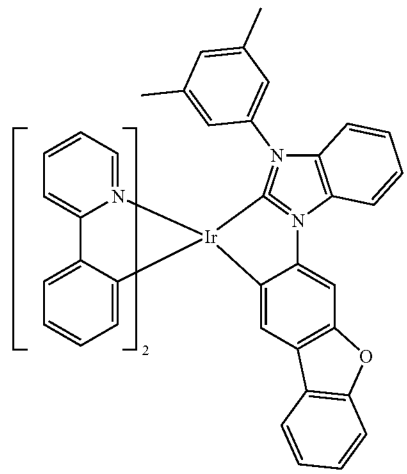
412
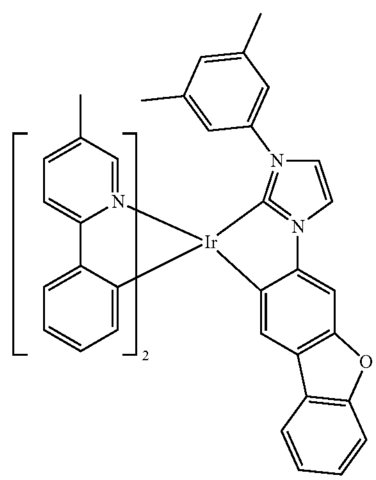
413
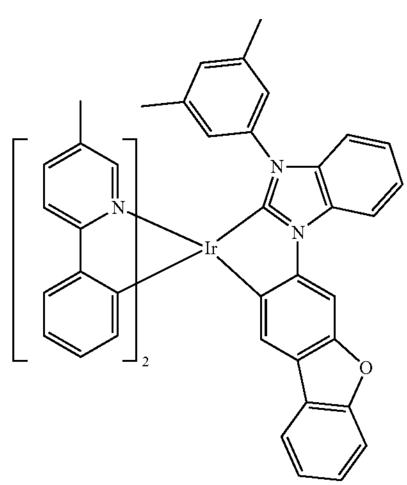

-continued
414
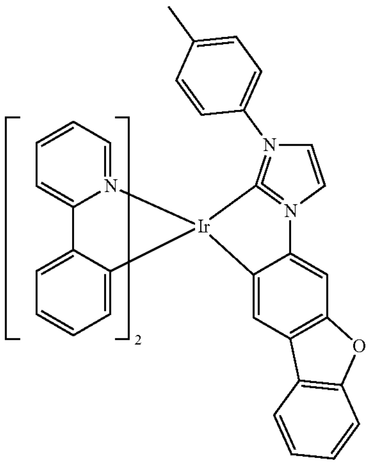
415
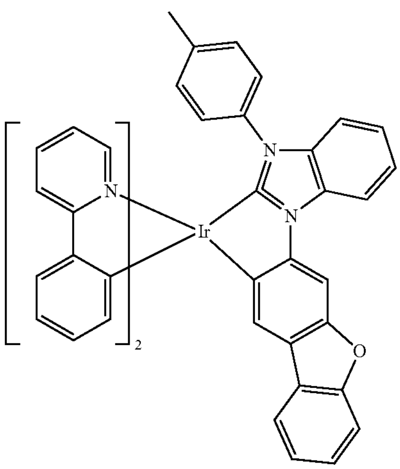
416
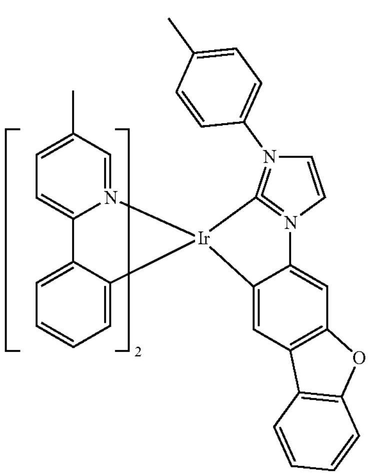
-continued
417
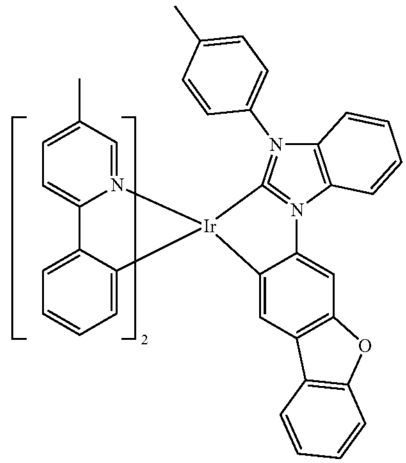
418
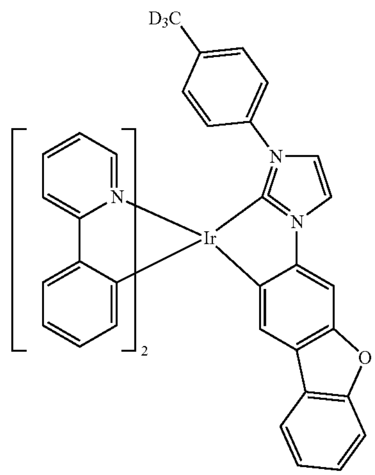
419
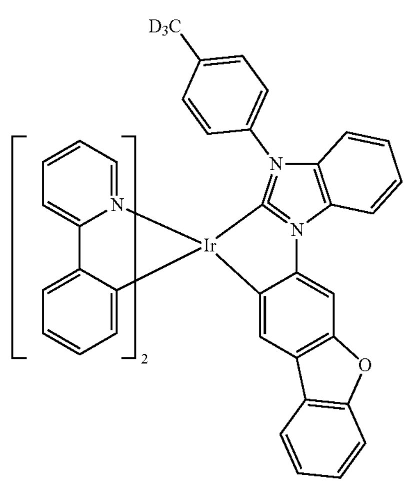

-continued
420
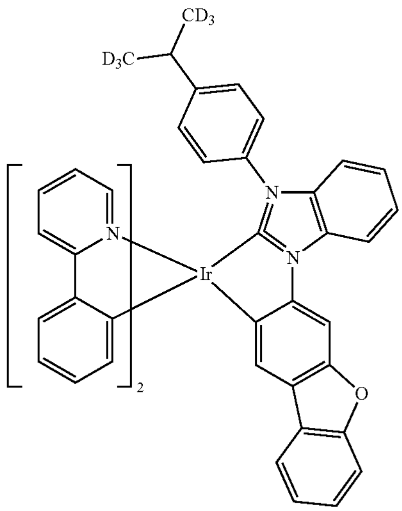
421
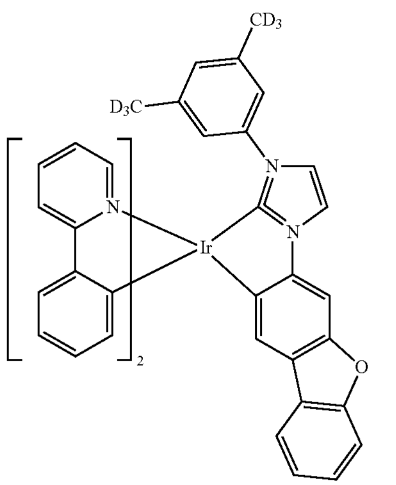
422
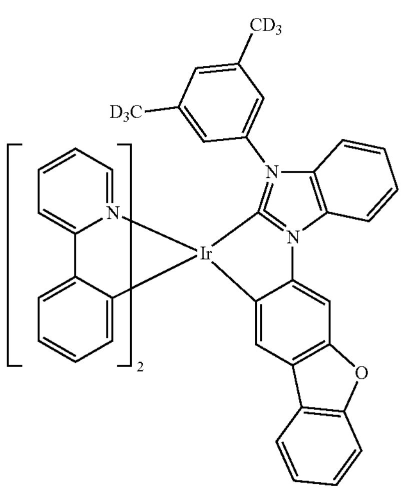
-continued
423
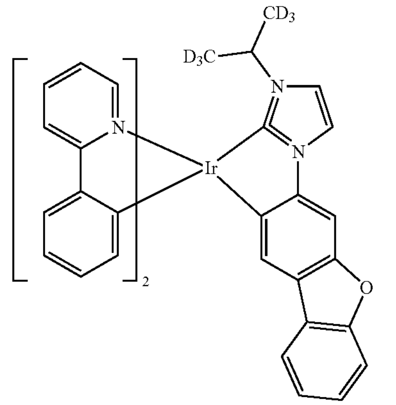
424
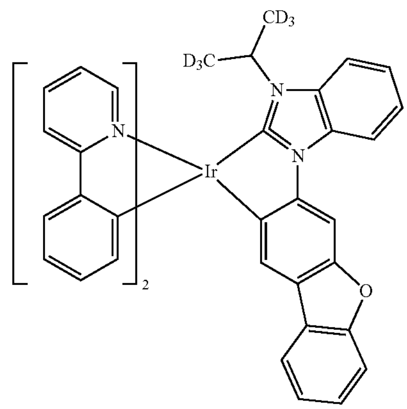
425
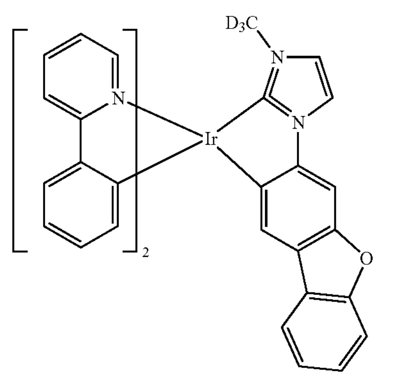
426
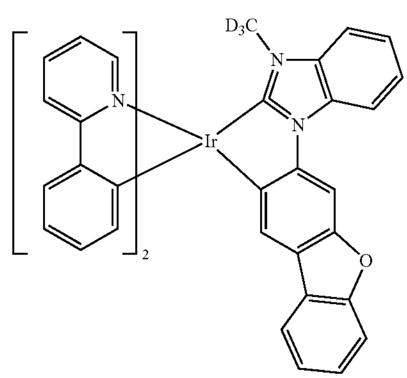

-continued
427
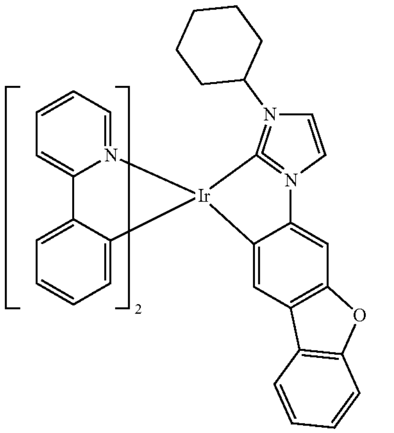
428
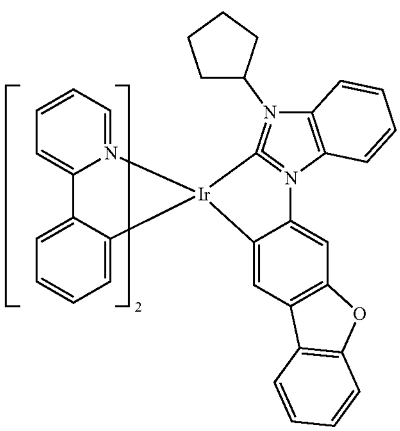
429
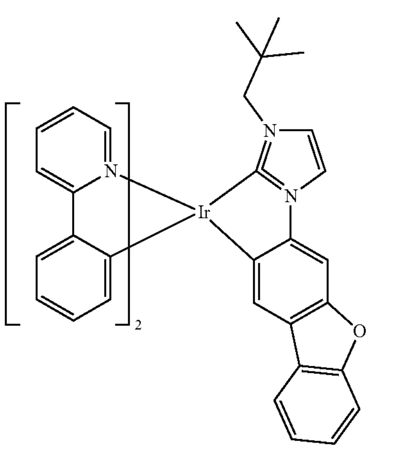
-continued
430
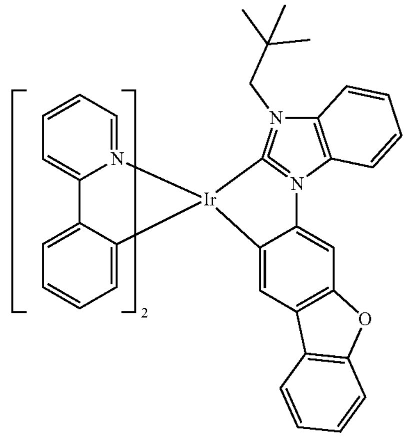
431
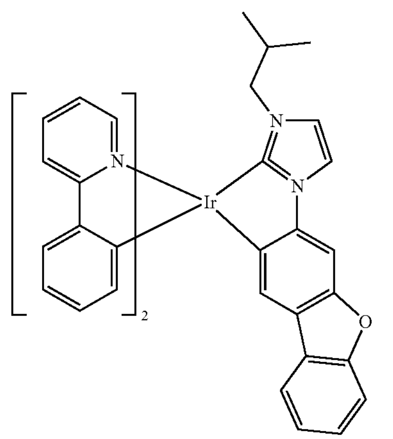
432
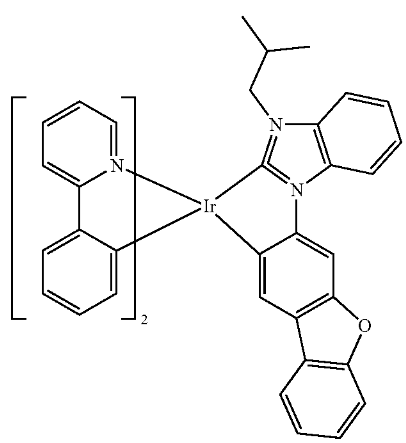

-continued
433
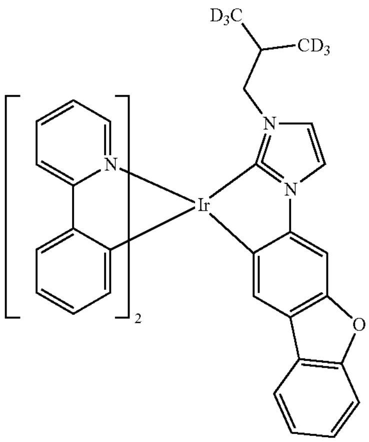
434
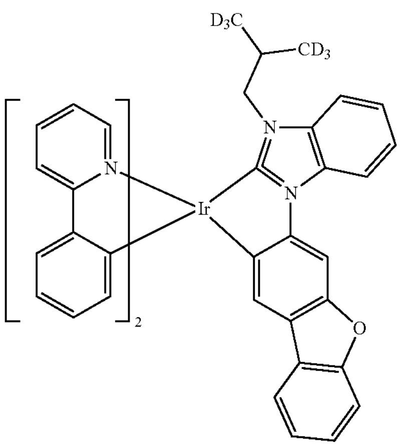
435
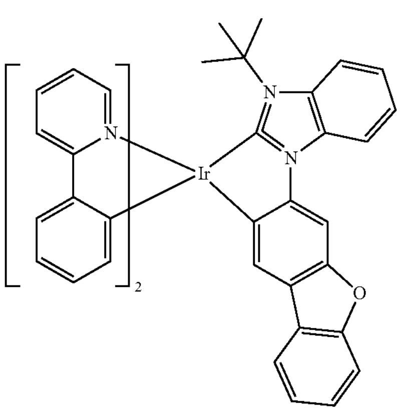
-continued
436
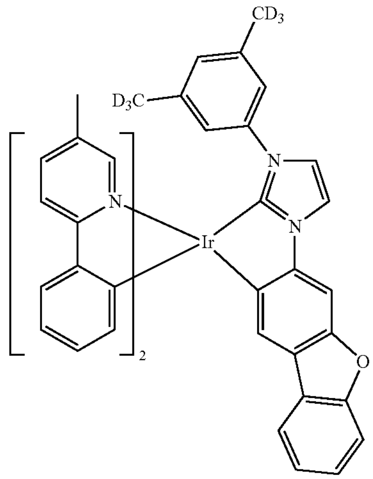
437
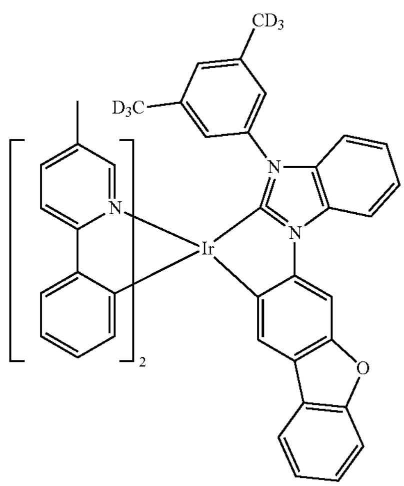
438
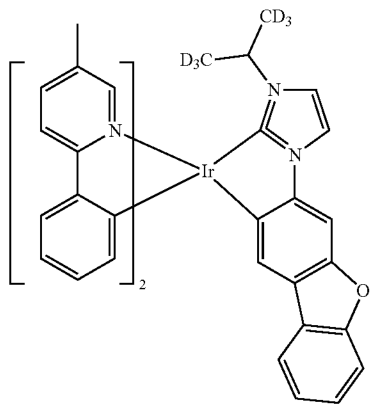

-continued
439
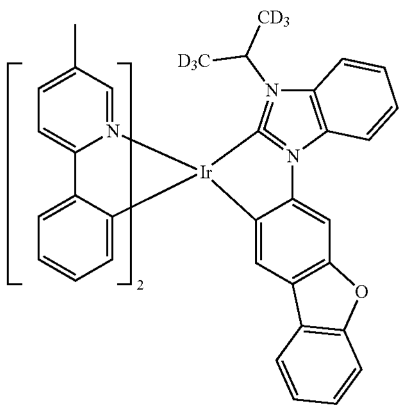
440
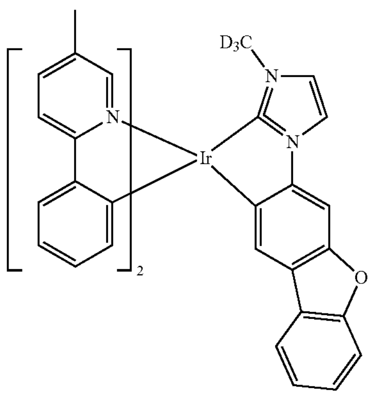
441
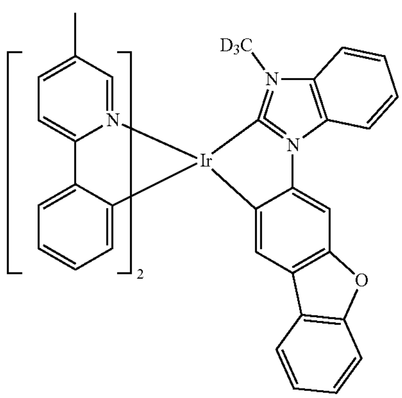
442
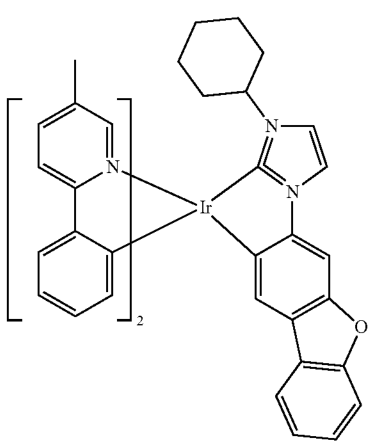
-continued
443
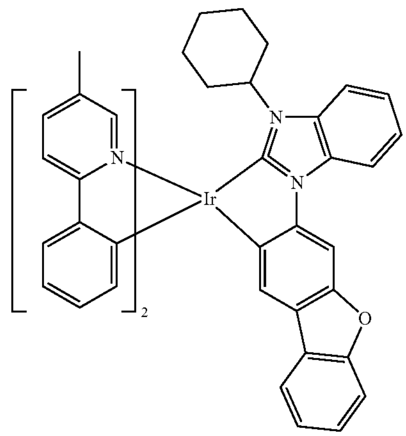
444
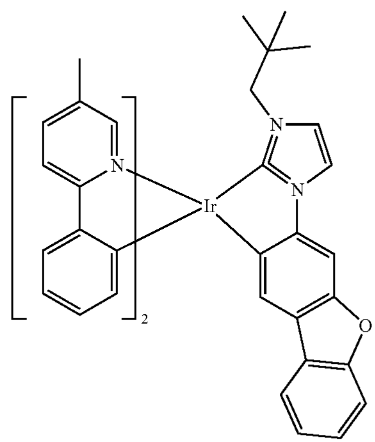
445
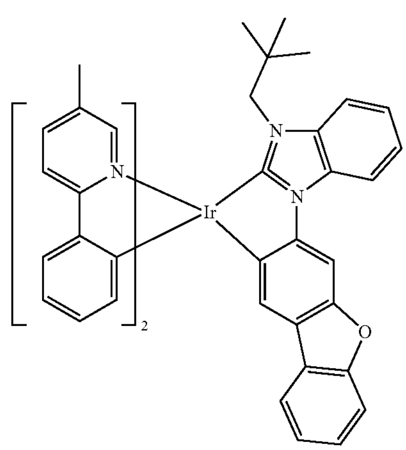

-continued
446
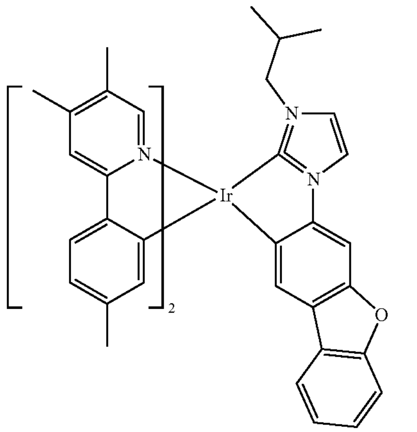
447
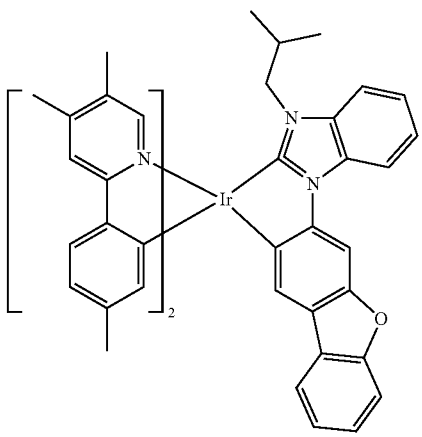
448
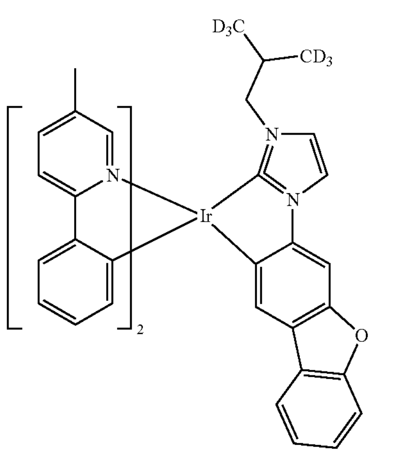
-continued
449
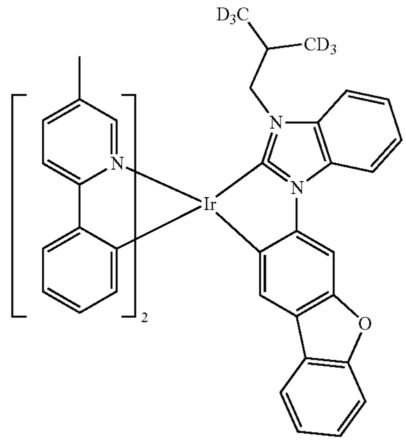
450
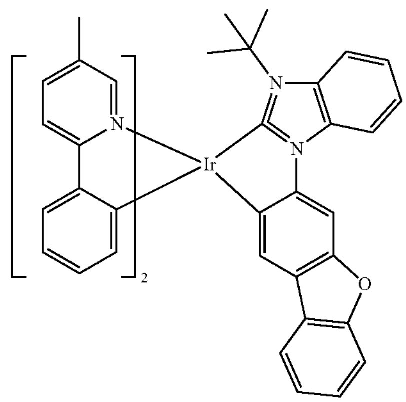
451
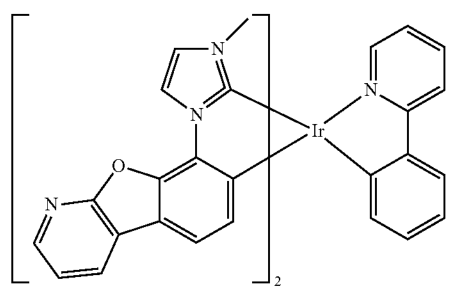
452
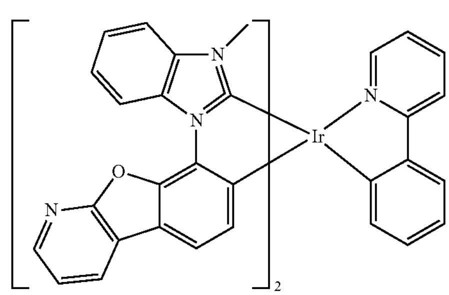

-continued
453
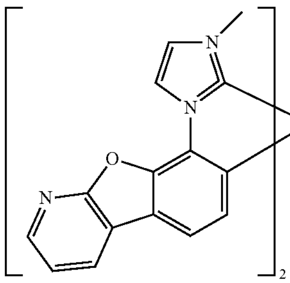
454
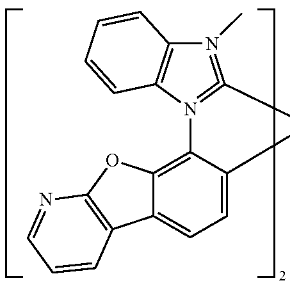
455
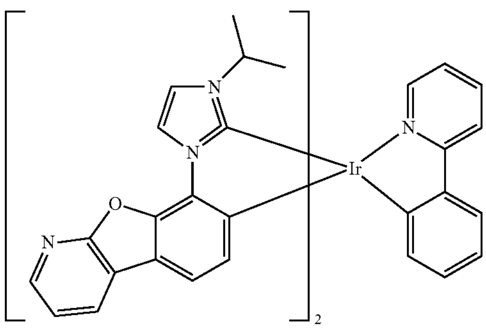
456
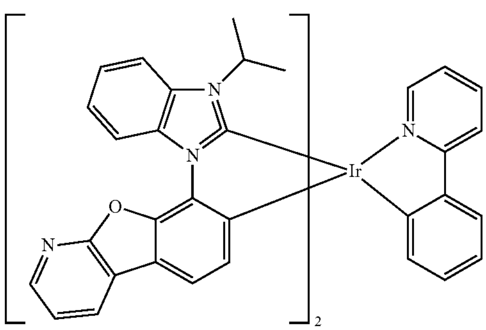
457
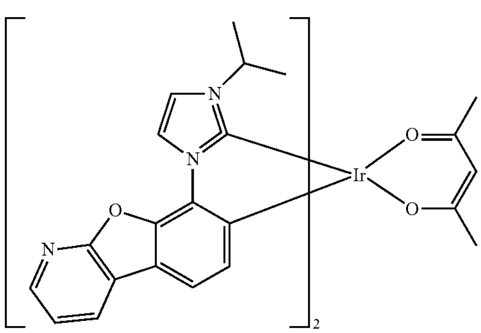
-continued
458
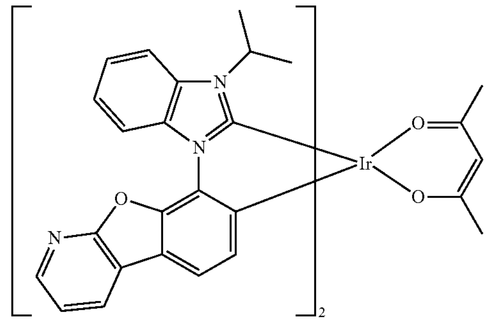
459
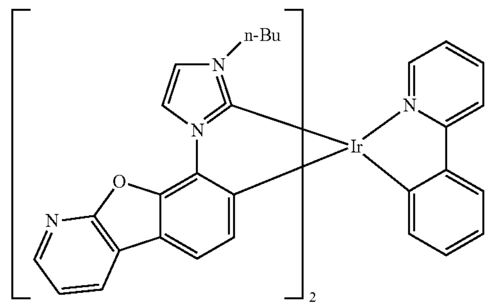
460
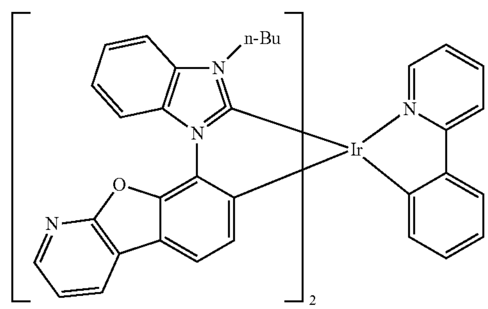
461
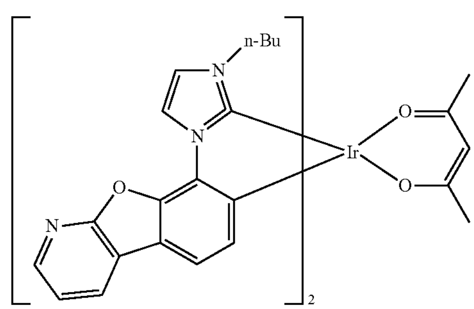
462
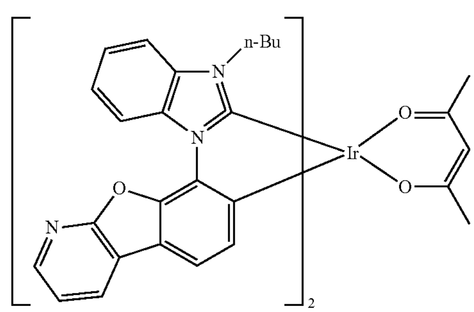

-continued
463
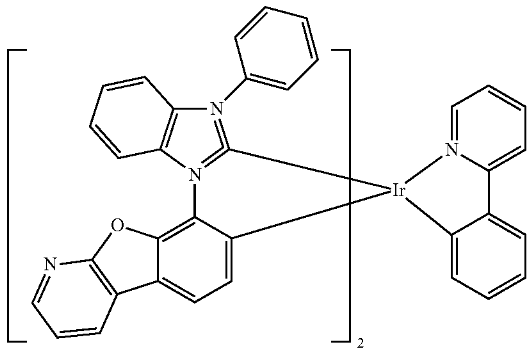
464
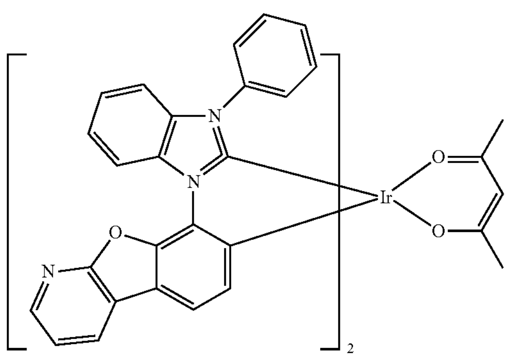
465
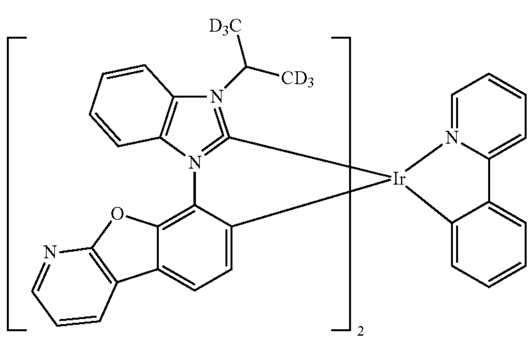
466
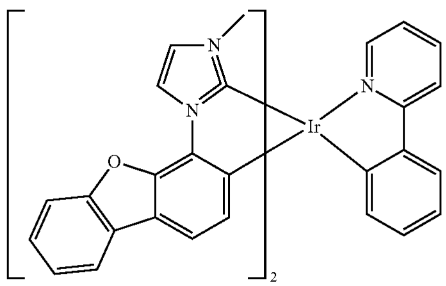
-continued
467
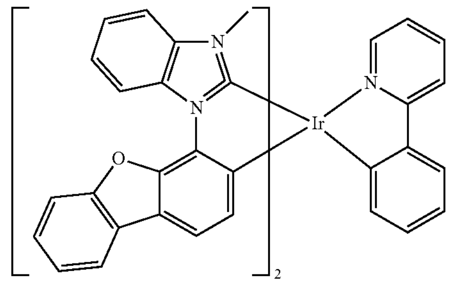
468
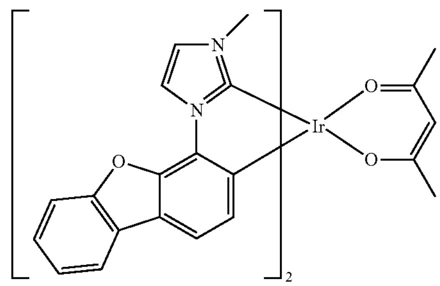
469
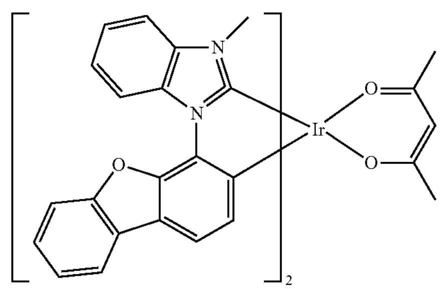
470
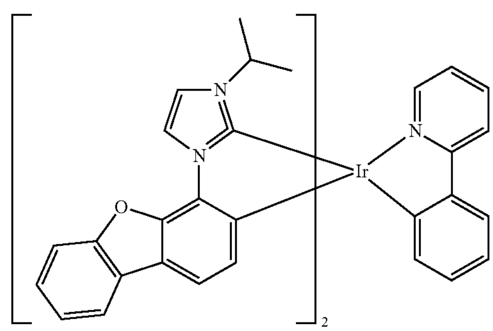
471
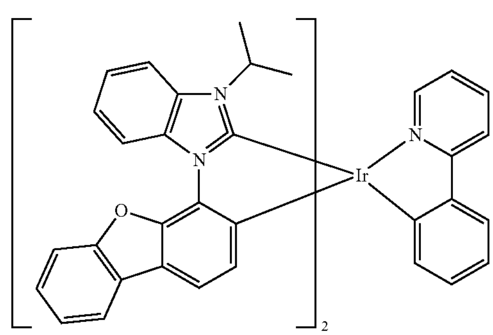

-continued
472
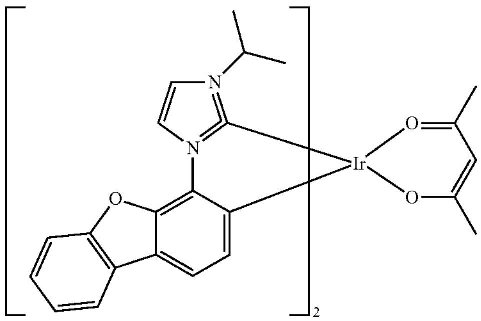
473
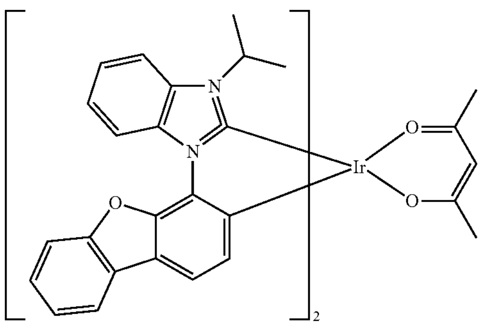
474
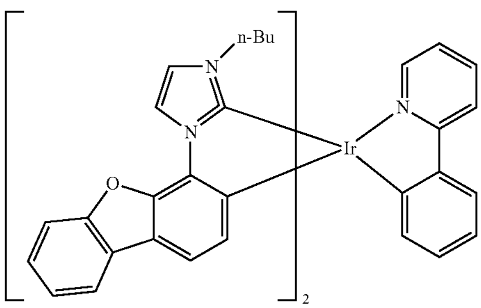
475
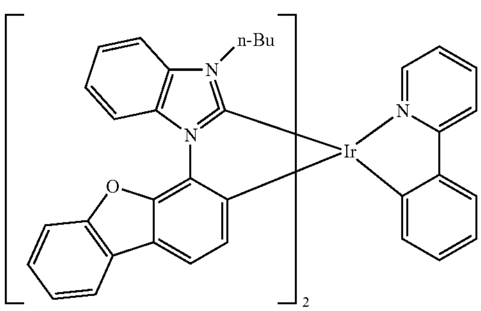
476
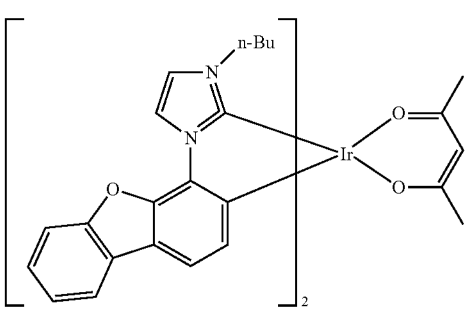
-continued
477
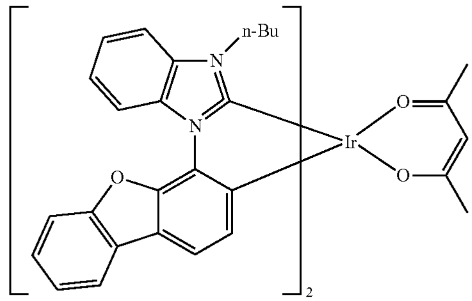
478
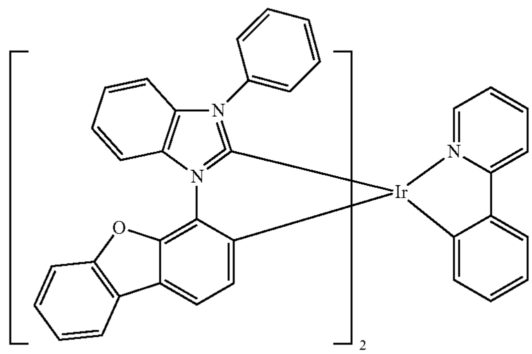
479
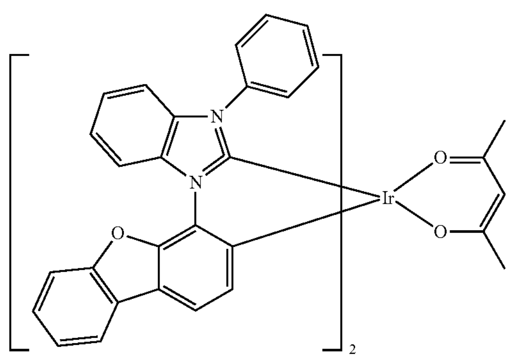
480
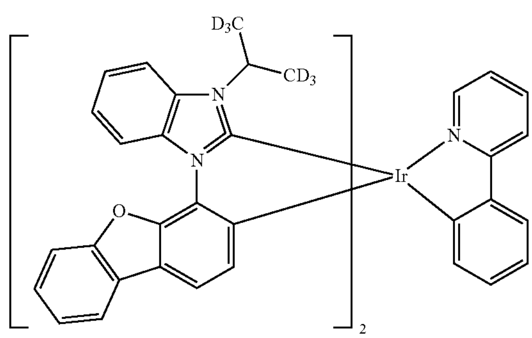

-continued
481
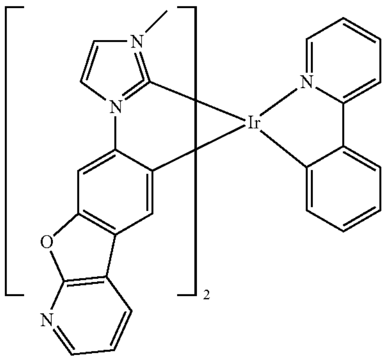
482
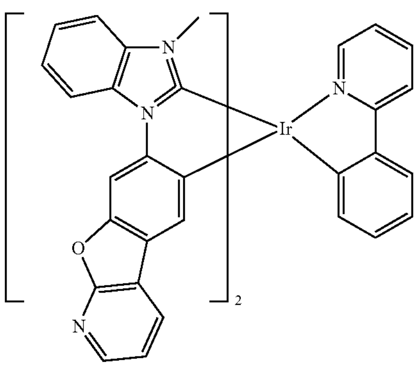
483
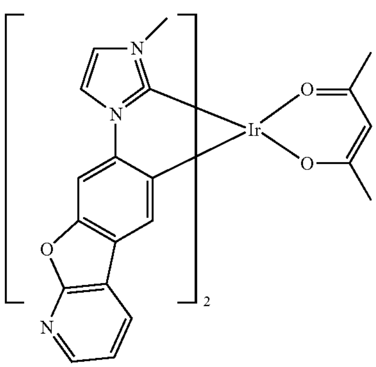
484
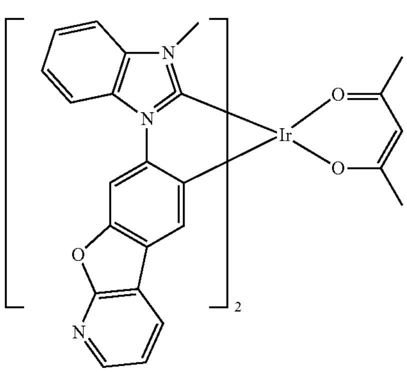
-continued
485
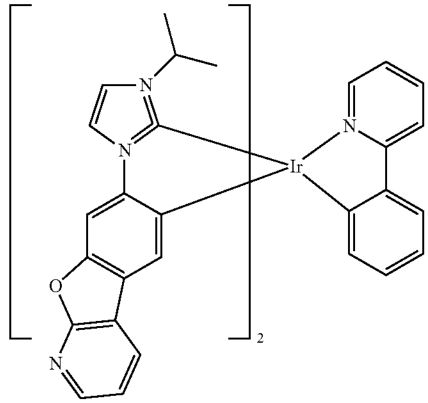
486
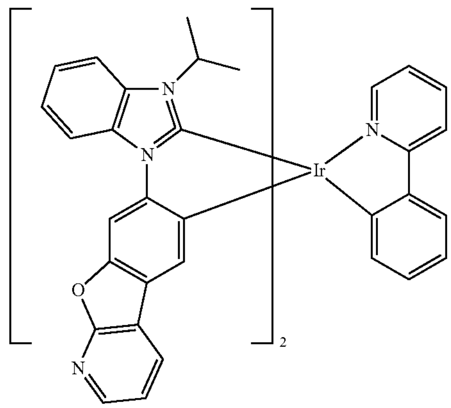
487
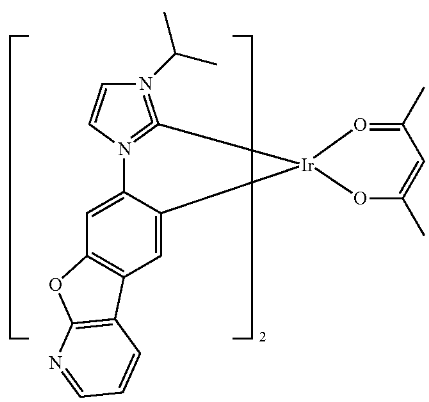
488
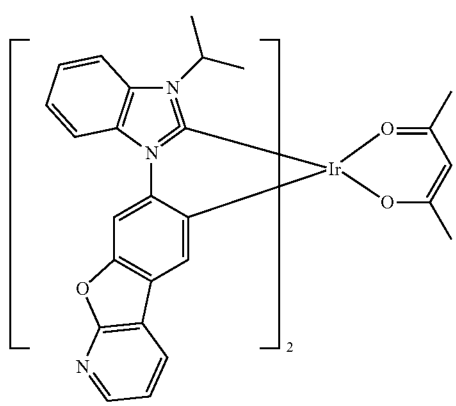

-continued
489
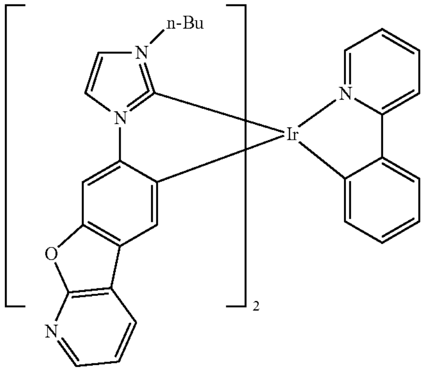
490
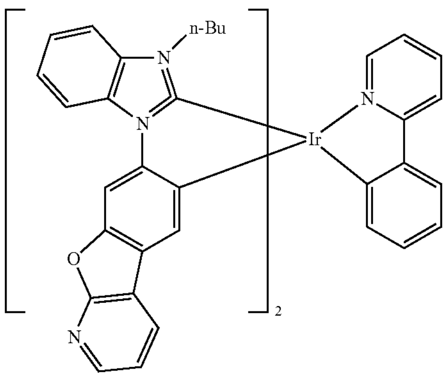
491
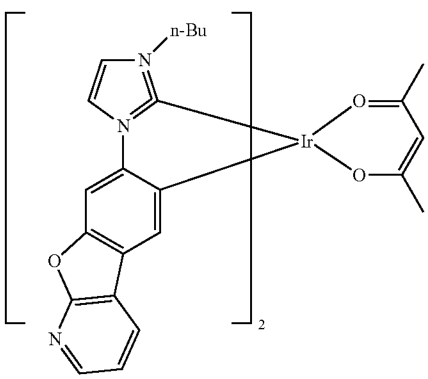
492
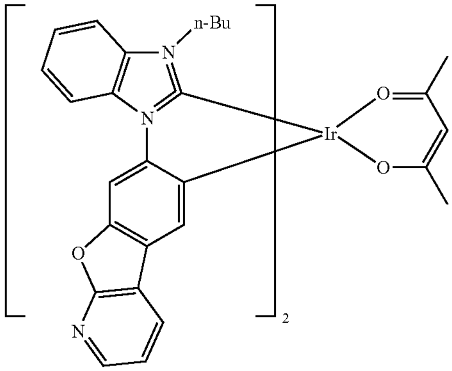
-continued
493
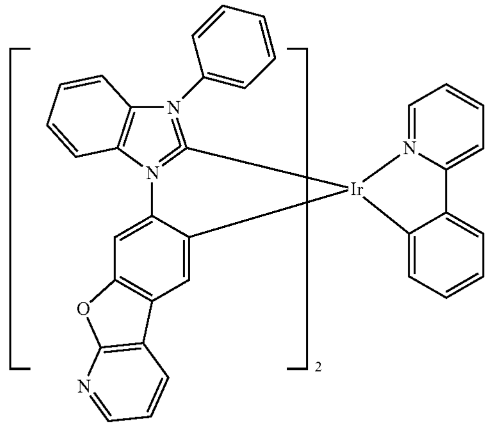
494
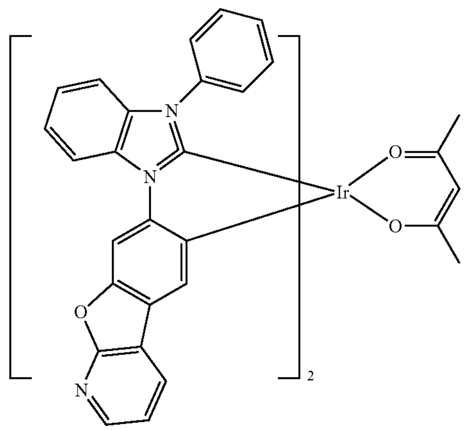
495
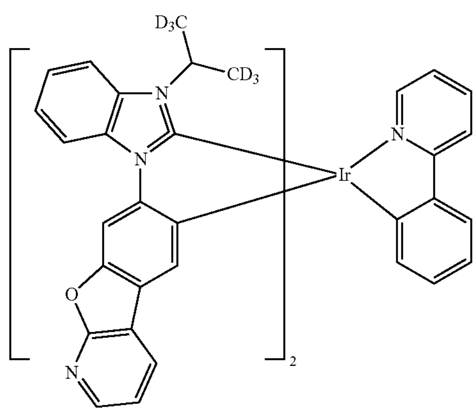
496
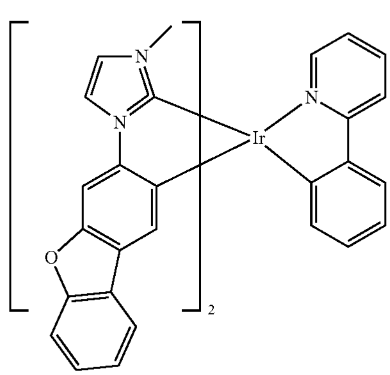

-continued
497
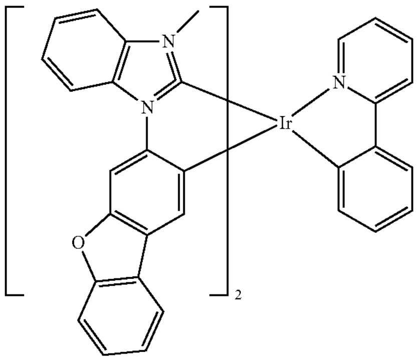
498
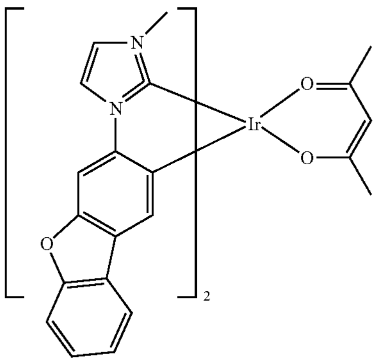
499
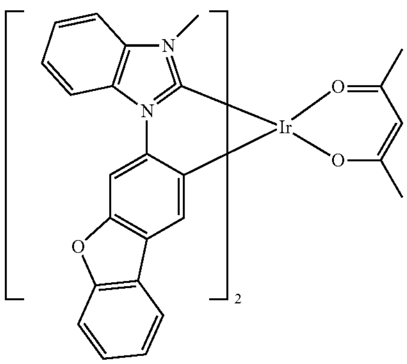
500
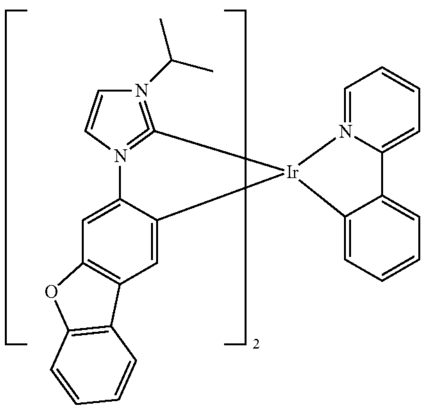
-continued
501
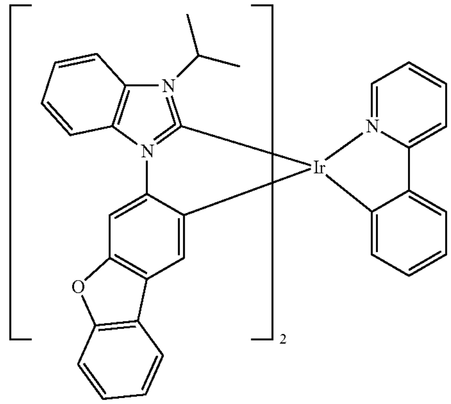
502
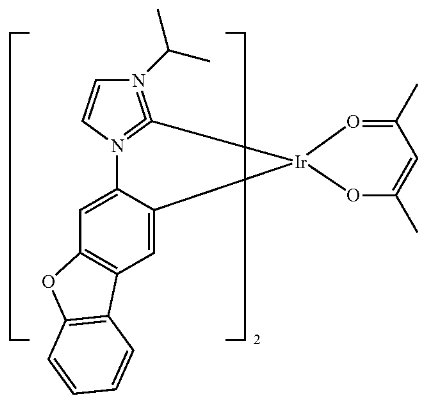
503
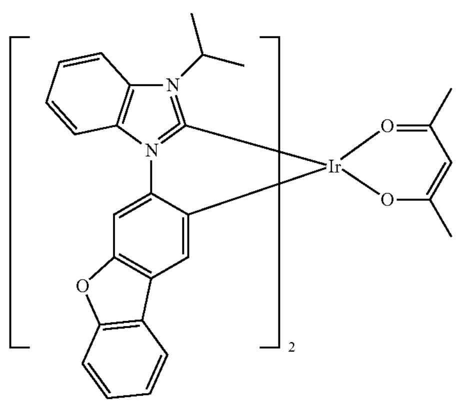
504
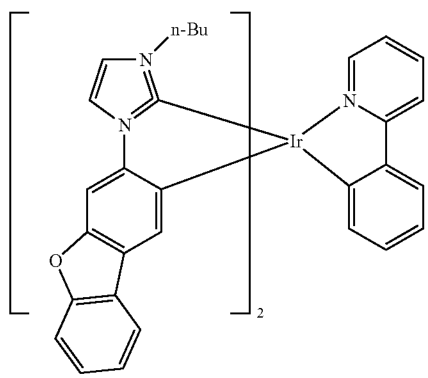

-continued

505

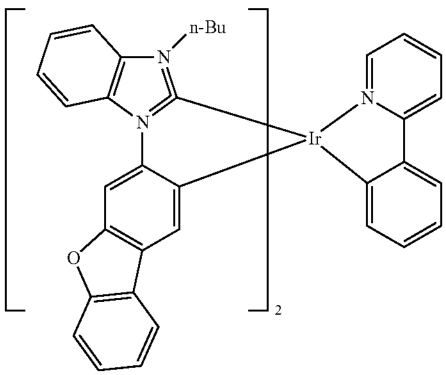

506

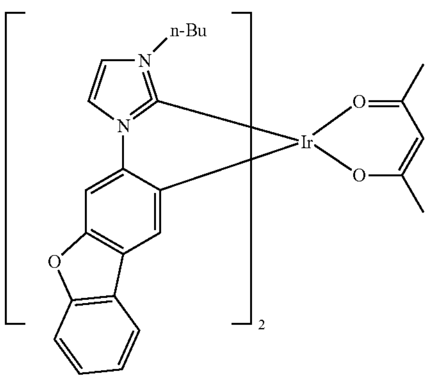

507

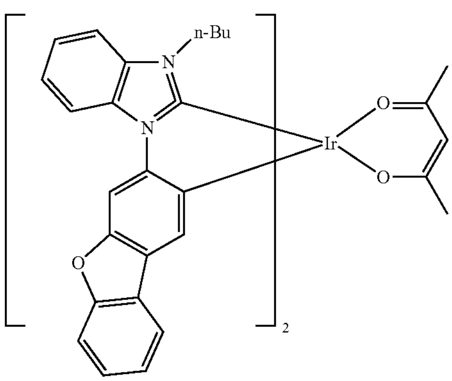

508

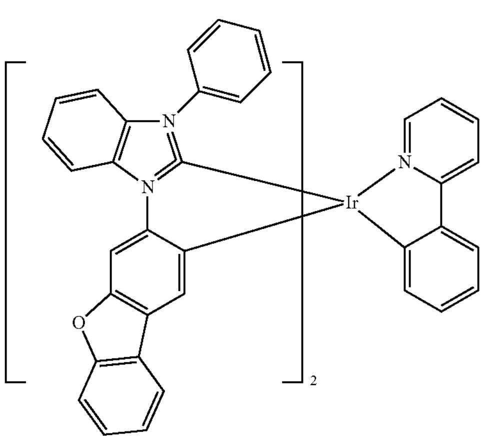

-continued

509

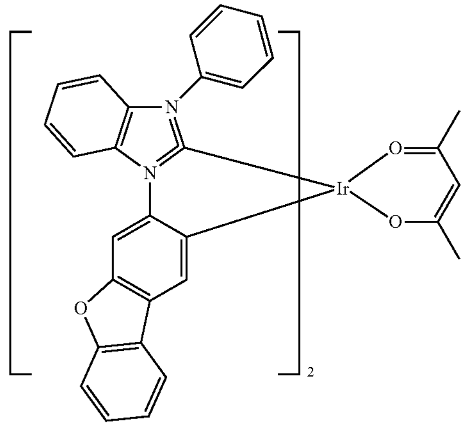

510

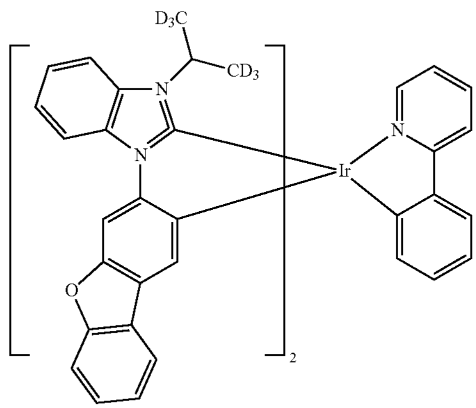

According to one implementation of the present disclosure, the organometallic compound represented by the Chemical Formula 1 of the present disclosure may be used as a red phosphorescent material or a green phosphorescent material, preferably, as the green phosphorescent material Referring to FIG. 1 according to one implementation of the present disclosure, an organic light-emitting diode 100 may be provided which includes a first electrode 110; a second electrode 120 facing the first electrode 110; and an organic layer 130 disposed between the first electrode 110 and the second electrode 120. The organic layer 130 may include a light-emitting layer 160, and the light-emitting layer 160 may include a host material 160' and dopants 160". The dopants 160" may be made of the organometallic compound represented by the Chemical Formula 1. In addition, in the organic light-emitting diode 100, the organic layer 130 disposed between the first electrode 110 and the second electrode 120 may be formed by sequentially stacking a hole injection layer 140 (HIL), a hole transport layer 150, (HTL), a light emission layer 160 (EML), an electron transport layer 170 (ETL) and an electron injection layer 180 (EIL) on the first electrode 110. The second electrode 120 may be formed on the electron injection layer 180, and a protective layer (not shown) may be formed thereon.

Further, although not shown in FIG. 1, a hole transport auxiliary layer may be further added between the hole transport layer 150 and the light-emitting layer 160. The hole transport auxiliary layer may contain a compound having good hole transport properties, and may reduce a difference between HOMO energy levels of the hole transport layer 150 and the light-emitting layer 160 so as to adjust the hole injection properties. Thus, accumulation of holes at an interface between the hole transport auxiliary layer and the light-emitting layer 160 may be reduced, thereby reducing a quenching phenomenon in which excitons disappear at the interface due to polarons. Accordingly, deterioration of the element may be reduced and the element may be stabilized, thereby improving efficiency and lifespan thereof.

The first electrode 110 may act as a positive electrode, and may be made of ITO, IZO, tin-oxide, or zinc-oxide as a conductive material having a relatively large work function value. However, the present disclosure is not limited thereto.

The second electrode 120 may act as a negative electrode, and may include Al, Mg, Ca, or Ag as a conductive material having a relatively small work function value, or an alloy or combination thereof. However, the present disclosure is not limited thereto.

The hole injection layer 140 may be positioned between the first electrode 110 and the hole transport layer 150. The hole injection layer 140 may have a function of improving interface characteristics between the first electrode 110 and the hole transport layer 150, and may be selected from a material having appropriate conductivity. The hole injection layer 140 may include one or more compounds selected from a group consisting of MTDATA, CuPc, TCTA, HATCN, TDAPB, PEDOT/PSS, and N1,N1'-([1,1'-biphenyl]-4,4'-diyl)bis(N1,N4,N4)-triphenylbenzene-1,4-diamine). Preferably, the hole injection layer 140 may include N1,N1'-([1,1'-biphenyl]-4,4'-diyl)bis(N1,N4,N4-triphenylbenzene-1,4-diamine). However, the present disclosure is not limited thereto.

The hole transport layer 150 may be positioned adjacent to the light-emitting layer and between the first electrode 110 and the light-emitting layer 160. A material of the hole transport layer 150 may include a compound selected from a group consisting of TPD, NPB, CBP, N-(biphenyl-4-yl)-9,9-dimethyl-N-(4-(9-phenyl-9H-carbazol-3-yl)phenyl)-9H-fluoren-2-amine, N-(biphenyl-4-yl)-N-(4-(9-phenyl-9H-carbazol-3-yl)phenyl)biphenyl)-4-amine, etc. Preferably, the material of the hole transport layer 150 may include NPB. However, the present disclosure is not limited thereto.

According to the present disclosure, the light-emitting layer 160 may include the host material 160' and the organometallic compound represented by the Chemical Formula 1 as dopants 160" doped into the host in order to improve luminous efficiency of the host and the organic light-emitting diode. The light-emitting layer 160 may be formed by adding about 1 to 30% by weight of the organometallic compound, that is, the dopants 160" of the Chemical Formula 1 of the present disclosure to the host material 160', and may emit light of a green or red color. More preferably, the organometallic compound of the Chemical Formula 1 of the present disclosure may act as a green phosphorescent material.

In the light-emitting layer 160 of the present disclosure, the organometallic compound represented by the Chemical Formula 1 may be used as the dopant 160", and a compound containing a carbazole group may be used as the host material 160'. For example, the host material containing the carbazole group may be one or more compounds selected from compounds of structures as shown in a following Table 1. However, the present disclosure is not limited thereto.

TABLE 1

| Structure of host material | Name of compound of host material |
|---|---|
| 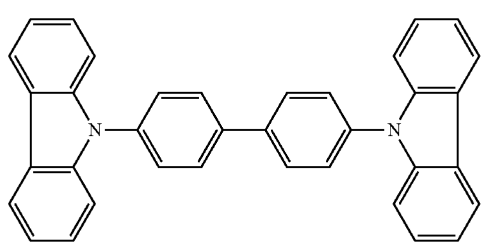 [SMILES: c1ccc2c(c1)c1ccccc1n2-c1ccc(-c2ccc(-n3c4ccccc4c4ccccc43)cc2)cc1] | CBP (4,4-Bis(9-carbazolyl)-1,1') |

TABLE 1-continued
| Structure of host material | Name of compound of host material |
|---|---|
| 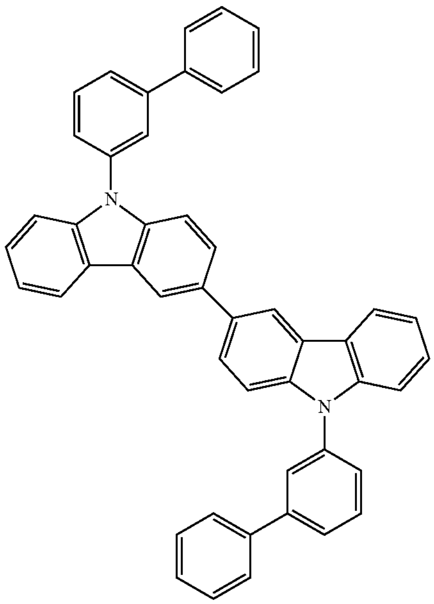 GH1 | 9,9'-di([1,1'-biphenyl]-3-yl)-9H,9'H-3,3'-bicarbazole |
| 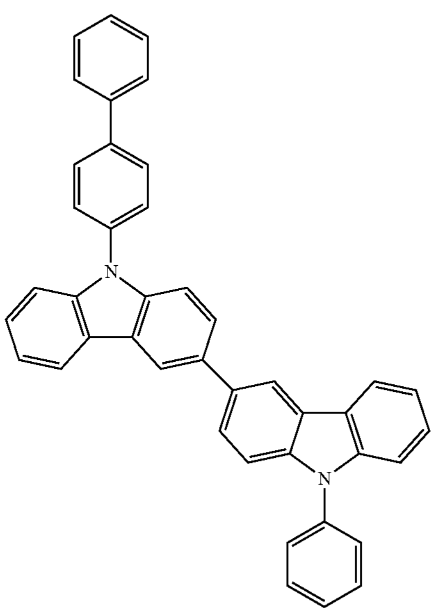 GH2 | 9-([1,1'-biphenyl]-4-yl)-9'-phenyl-9H,9'H-3,3'-bicarbazole |

TABLE 1-continued
| Structure of host material | Name of compound of host material |
|---|---|
| 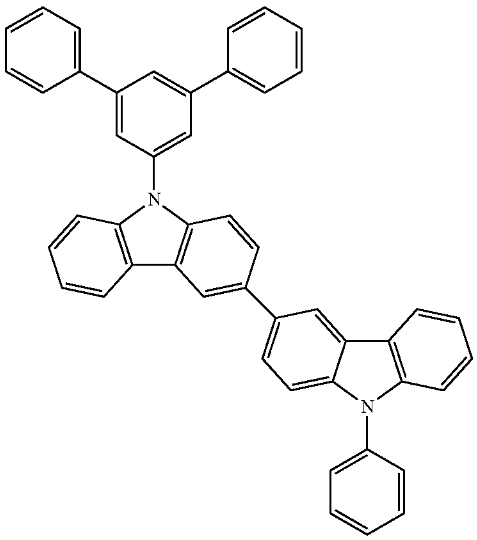 GH3 | 9-([1,1':3',1''-terphenyl]-5'-yl)-9'-phenyl-9H,9'H-3,3'-bicarbazole |
| 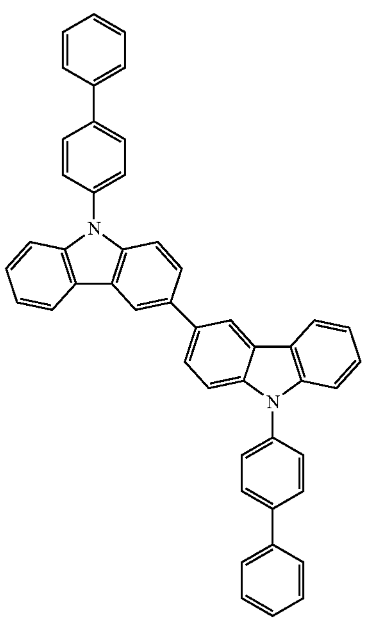 GH4 | 9,9'-di([1,1'-biphenyl]-4-yl)-9H,9'H-3,3'-bicarbazole |

TABLE 1-continued

| Structure of host material | Name of compound of host material |
|---|---|
| 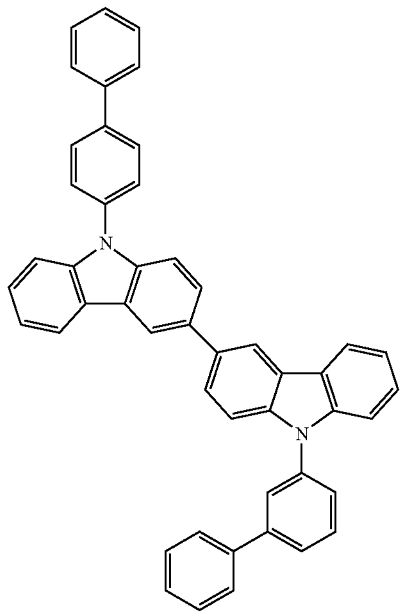 GH5 | 9-([1,1'-biphenyl]-3-yl)-9'-([1,1'-biphenyl]-4-yl)-9H,9'H-3,3'-bicarbazole |

Further, the electron transport layer 170 and the electron injection layer 180 may be sequentially stacked between the light-emitting layer 160 and the second electrode 120. A material of the electron transport layer 170 requires high electron mobility such that electrons may be stably supplied to the light-emitting layer under smooth electron transport.

For example, the material of the electron transport layer 170 may include a compound selected from a group consisting of Alq3 (tris(8-hydroxyquinolino)aluminum), Liq (8-hydroxyquinolinolatolithium), PBD (2-(4-biphenylyl)-5-(4-tert-butylphenyl)-1,3,4oxadiazole), TAZ (3-(4-biphenyl)$_4$ -phenyl-5-tert-butylphenyl-1,2,4-triazole), spiro-PBD, BAlq (bis(2-methyl-8-quinolinolate)-4-(phenylphenolato)aluminium), SAlq, TPBi (2,2',2-(1,3,5-benzinetriyl)-tris(1-phenyl-1-H-benzimidazole), oxadiazole, triazole, phenanthroline, benzoxazole, benzthiazole, and 2-(4-(9,10-di (naphthalen-2-yl)anthracen-2-yl)phenyl)-1-phenyl-1H-benzo[d]imidazole. Preferably, the material of the electron transport layer 170 may include 2-(4-(9,10-di(naphthalen-2-yl) anthracen-2-yl)phenyl)-1-phenyl-1H-benzo[d]imidazole. However, the present disclosure is not limited thereto.

The electron injection layer 180 serves to facilitate electron injection, and a material of the electron injection layer may include a compound selected from a group consisting of Alq3 (tris(8-hydroxyquinolino)aluminum), PBD, TAZ, Spiro-PBD, BAlq, SAlq, etc. However, the present disclosure is not limited thereto. Alternatively, the electron injection layer 180 may be made of a metal compound. The metal compound may include, for example, one or more selected from a group consisting of Liq, LiF, NaF, KF, RbF, CsF, FrF, $BeF_2$, $MgF_2$, $CaF_2$, $SrF_2$, $BaF_2$ and $RaF_2$. However, the present disclosure is not limited thereto.

The organic light-emitting diode according to the present disclosure may be embodied as a white light-emitting diode having a tandem structure. The tandem organic light-emitting diode according to an illustrative embodiment of the present disclosure may be formed in a structure in which adjacent ones of two or more light-emitting stacks are connected to each other via a charge generation layer (CGL). The organic light-emitting diode may include at least two light-emitting stacks disposed on a substrate, wherein each of the at least two light-emitting stacks includes first and second electrodes facing each other, and the light-emitting layer disposed between the first and second electrodes to emit light in a specific wavelength band. In this case, the light-emitting layer included in at least one of the plurality of light-emitting stacks may contain the organometallic compound represented by the Chemical Formula 1 according to the present disclosure as the dopants. Adjacent ones of the plurality of light-emitting stacks in the tandem structure may be connected to each other via the charge generation layer CGL including an N-type charge generation layer and a P-type charge generation layer.

Figure 2:
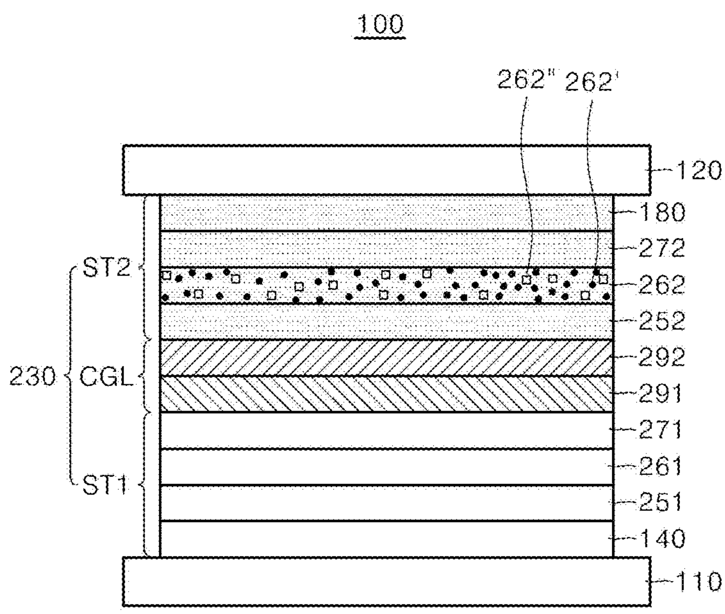
FIG. 2 is a cross-sectional view schematically illustrating an organic light-emitting diode having a tandem structure having two light-emitting stacks and containing an organometallic compound represented by the Chemical Formula 1 according to an illustrative embodiment of the present disclosure.
Figure 3:
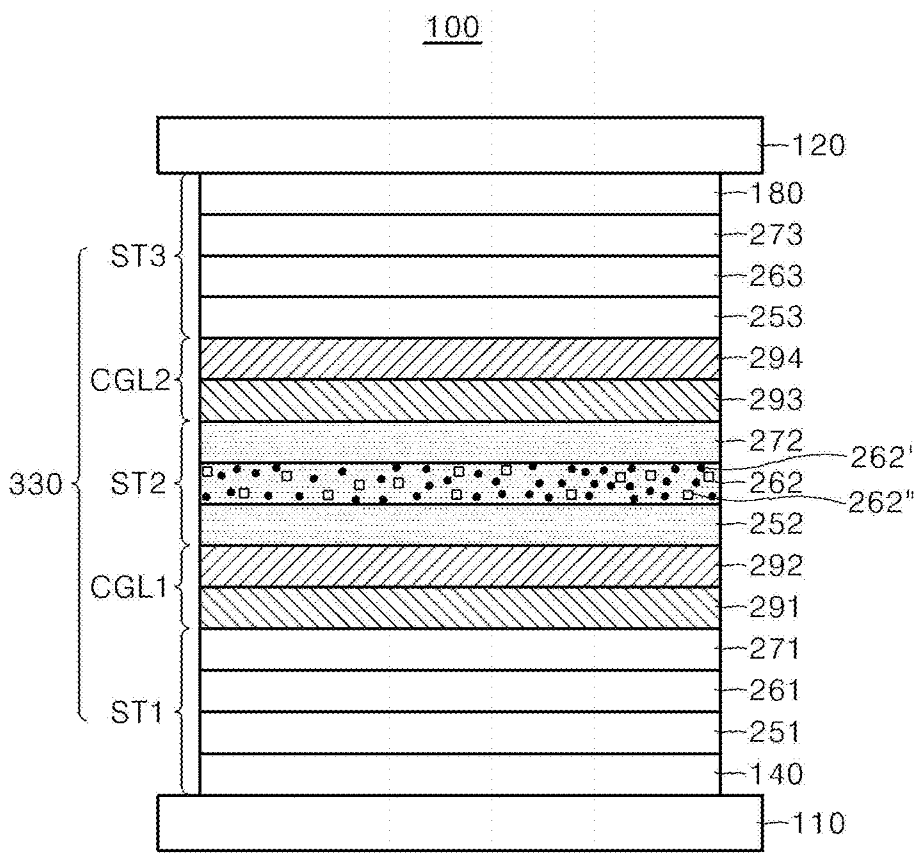
FIG. 3 is a cross-sectional view schematically illustrating an organic light-emitting diode having a tandem structure having three light-emitting stacks and containing an organometallic compound represented by the Chemical Formula 1 according to an illustrative embodiment of the present disclosure.

FIG. 2 and FIG. 3 are cross-sectional views schematically showing an organic light-emitting diode in a tandem structure having two light-emitting stacks and an organic light-emitting diode in a tandem structure having three light-emitting stacks, respectively, according to some implementations of the present disclosure.

As shown in FIG. 2, an organic light-emitting diode 100 according to the present disclosure include a first electrode 110 and a second electrode 120 facing each other, and an organic layer 230 positioned between the first electrode 110 and the second electrode 120. The organic layer 230 may be positioned between the first electrode 110 and the second electrode 120 and may include a first light-emitting stack ST1 including a first light-emitting layer 261, a second light-emitting stack ST2 positioned between the first light-emitting stack ST1 and the second electrode 120 and including a second light-emitting layer 262, and the charge generation layer CGL positioned between the first and second light-emitting stacks ST1 and ST2. The charge generation layer CGL may include an N-type charge generation layer 291 and a P-type charge generation layer 292. At least one of the first light-emitting layer 261 and the second light-emitting layer 262 may contain the organometallic compound represented by the Chemical Formula 1 according to the present disclosure as the dopants. For example, as shown in FIG. 2, the second light-emitting layer 262 of the second light-emitting stack ST2 may contain a host material 262', and dopants 262" made of the organometallic compound represented by the Chemical Formula 1 doped therein.

As shown in FIG. 3, the organic light-emitting diode 100 according to the present disclosure include the first electrode 110 and the second electrode 120 facing each other, and an organic layer 330 positioned between the first electrode 110 and the second electrode 120. The organic layer 330 may be positioned between the first electrode 110 and the second electrode 120 and may include the first light-emitting stack ST1 including the first light-emitting layer 261, the second light-emitting stack ST2 including the second light-emitting layer 262, a third light-emitting stack ST3 including a third light-emitting layer 263, a first charge generation layer CGL1 positioned between the first and second light-emitting stacks ST1 and ST2, and a second charge generation layer CGL2 positioned between the second and third light-emitting stacks ST2 and ST3. The first charge generation layer CGL1 may include a N-type charge generation layers 291 and a P-type charge generation layer 292. The second charge generation layer CGL2 may include a N-type charge generation layers 293 and a P-type charge generation layer 294. At least one of the first light-emitting layer 261, the second light-emitting layer 262, and the third light-emitting layer 263 may contain the organometallic compound represented by the Chemical Formula 1 according to the present disclosure as the dopants. For example, as shown in FIG. 3, the second light-emitting layer 262 of the second light-emitting stack ST2 may contain the host material 262', and the dopants 262" made of the organometallic compound represented by the Chemical Formula 1 doped therein.

Furthermore, an organic light-emitting diode according to an embodiment of the present disclosure may include a tandem structure in which four or more light-emitting stacks and three or more charge generating layers are disposed between the first electrode and the second electrode.

The organic light-emitting diode according to the present disclosure may be used as a light-emitting element of each of an organic light-emitting display device and a lighting device. In one implementation, FIG. 4 is a cross-sectional view schematically illustrating an organic light-emitting display device including the organic light-emitting diode according to some embodiments of the present disclosure as a light-emitting element thereof.

Figure 4:
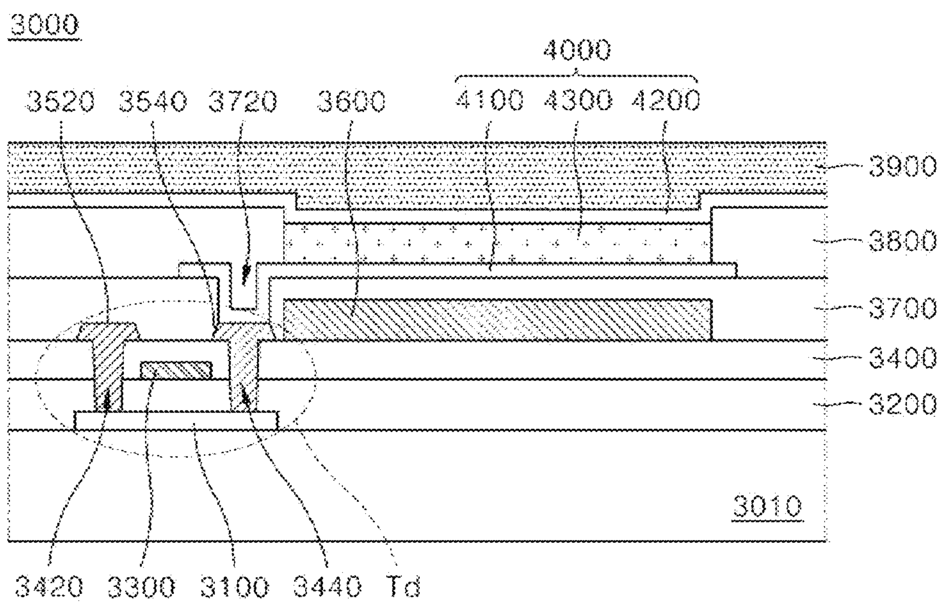
FIG. 4 is a cross-sectional view schematically illustrating an organic light-emitting display device including an organic light-emitting diode according to an illustrative embodiment of the present disclosure.

As shown in FIG. 4, an organic light-emitting display device 3000 includes a substrate 3010, an organic light-emitting diode 4000, and an encapsulation film 3900 covering the organic light-emitting diode 4000. A driving thin-film transistor Td as a driving element, and the organic light-emitting diode 4000 connected to the driving thin-film transistor Td are positioned on the substrate 3010.

Although not shown explicitly in FIG. 4, a gate line and a data line that intersect each other to define a pixel area, a power line extending parallel to and spaced from one of the gate line and the data line, a switching thin film transistor connected to the gate line and the data line, and a storage capacitor connected to one electrode of the thin film transistor and the power line are further formed on the substrate 3010.

The driving thin-film transistor Td is connected to the switching thin film transistor, and includes a semiconductor layer 3100, a gate electrode 3300, a source electrode 3520, and a drain electrode 3540.

The semiconductor layer 3100 may be formed on the substrate 3010 and may be made of an oxide semiconductor material or polycrystalline silicon. When the semiconductor layer 3100 is made of an oxide semiconductor material, a light-shielding pattern (not shown) may be formed under the semiconductor layer 3100. The light-shielding pattern prevents light from being incident into the semiconductor layer 3100 to prevent the semiconductor layer 3010 from being deteriorated due to the light. Alternatively, the semiconductor layer 3100 may be made of polycrystalline silicon. In this case, both edges of the semiconductor layer 3100 may be doped with impurities.

The gate insulating layer 3200 made of an insulating material is formed over an entirety of a surface of the substrate 3010 and on the semiconductor layer 3100. The gate insulating layer 3200 may be made of an inorganic insulating material such as silicon oxide or silicon nitride.

The gate electrode 3300 made of a conductive material such as a metal is formed on the gate insulating layer 3200 and corresponds to a center of the semiconductor layer 3100. The gate electrode 3300 is connected to the switching thin film transistor.

The interlayer insulating layer 3400 made of an insulating material is formed over the entirety of the surface of the substrate 3010 and on the gate electrode 3300. The interlayer insulating layer 3400 may be made of an inorganic insulating material such as silicon oxide or silicon nitride, or an organic insulating material such as benzocyclobutene or photo-acryl.

The interlayer insulating layer 3400 has first and second semiconductor layer contact holes 3420 and 3440 defined therein respectively exposing both opposing sides of the semiconductor layer 3100. The first and second semiconductor layer contact holes 3420 and 3440 are respectively positioned on both opposing sides of the gate electrode 3300 and are spaced apart from the gate electrode 3300.

The source electrode 3520 and the drain electrode 3540 made of a conductive material such as metal are formed on the interlayer insulating layer 3400. The source electrode 3520 and the drain electrode 3540 are positioned around the gate electrode 3300, and are spaced apart from each other, and respectively contact both opposing sides of the semiconductor layer 3100 via the first and second semiconductor layer contact holes 3420 and 3440, respectively. The source electrode 3520 is connected to a power line (not shown).

The semiconductor layer 3100, the gate electrode 3300, the source electrode 3520, and the drain electrode 3540 constitute the driving thin-film transistor Td. The driving thin-film transistor Td has a coplanar structure in which the gate electrode 3300, the source electrode 3520, and the drain electrode 3540 are positioned on top of the semiconductor layer 3100.

Alternatively, the driving thin-film transistor Td may have an inverted staggered structure in which the gate electrode is disposed under the semiconductor layer while the source electrode and the drain electrode are disposed above the semiconductor layer. In this case, the semiconductor layer may be made of amorphous silicon. In one example, the switching thin-film transistor (not shown) may have substantially the same structure as that of the driving thin-film transistor (Td).

In one example, the organic light-emitting display device 3000 may include a color filter 3600 absorbing the light generated from the electroluminescent element (light-emitting diode) 4000. For example, the color filter 3600 may absorb red (R), green (G), blue (B), and white (W) light. In this case, red, green, and blue color filter patterns that absorb light may be formed separately in different pixel areas. Each of these color filter patterns may be disposed to overlap each organic layer 4300 of the organic light-emitting diode 4000 to emit light of a wavelength band corresponding to each color filter. Adopting the color filter 3600 may allow the organic light-emitting display device 3000 to realize full-color.

For example, when the organic light-emitting display device 3000 is of a bottom emission type, the color filter 3600 absorbing light may be positioned on a portion of the interlayer insulating layer 3400 corresponding to the organic light-emitting diode 4000. In an optional embodiment, when the organic light-emitting display device 3000 is of a top emission type, the color filter may be positioned on top of the organic light-emitting diode 4000, that is, on top of a second electrode 4200. For example, the color filter 3600 may be formed to have a thickness of 2 to 5 μm.

In one example, a protective layer 3700 having a drain contact hole 3720 defined therein exposing the drain electrode 3540 of the driving thin-film transistor Td is formed to cover the driving thin-film transistor Td.

On the protective layer 3700, each first electrode 4100 connected to the drain electrode 3540 of the driving thin-film transistor Td via the drain contact hole 3720 is formed individually in each pixel area.

The first electrode 4100 may act as a positive electrode (anode), and may be made of a conductive material having a relatively large work function value. For example, the first electrode 4100 may be made of a transparent conductive material such as ITO, IZO or ZnO.

In one example, when the organic light-emitting display device 3000 is of a top-emission type, a reflective electrode or a reflective layer may be further formed under the first electrode 4100. For example, the reflective electrode or the reflective layer may be made of one of aluminum (Al), silver (Ag), nickel (Ni), and an aluminum-palladium-copper (APC) alloy.

A bank layer 3800 covering an edge of the first electrode 4100 is formed on the protective layer 3700. The bank layer 3800 exposes a center of the first electrode 4100 corresponding to the pixel area.

An organic layer 4300 is formed on the first electrode 4100. If necessary, the organic light-emitting diode 4000 may have a tandem structure. Regarding the tandem structure, reference may be made to FIG. 2 to FIG. 4 which show some embodiments of the present disclosure, and the above descriptions thereof.

The second electrode 4200 is formed on the substrate 3010 on which the organic layer 4300 has been formed. The second electrode 4200 is disposed over the entirety of the surface of the display area and is made of a conductive material having a relatively small work function value and may be used as a negative electrode (a cathode). For example, the second electrode 4200 may be made of one of aluminum (Al), magnesium (Mg), and an aluminum-magnesium alloy (Al—Mg).

The first electrode 4100, the organic layer 4300, and the second electrode 4200 constitute the organic light-emitting diode 4000.

An encapsulation film 3900 is formed on the second electrode 4200 to prevent external moisture from penetrating into the organic light-emitting diode 4000. Although not shown explicitly in FIG. 4, the encapsulation film 3900 may have a triple-layer structure in which a first inorganic layer, an organic layer, and an inorganic layer are sequentially stacked. However, the present disclosure is not limited thereto.

Hereinafter, Synthesis Example and Present Example of the present disclosure will be described. However, following Present Example is only one example of the present disclosure. The present disclosure is not limited thereto.

Synthesis Example—Preparation of Ligand Intermediate Product

<Preparation of Ligand A-2>

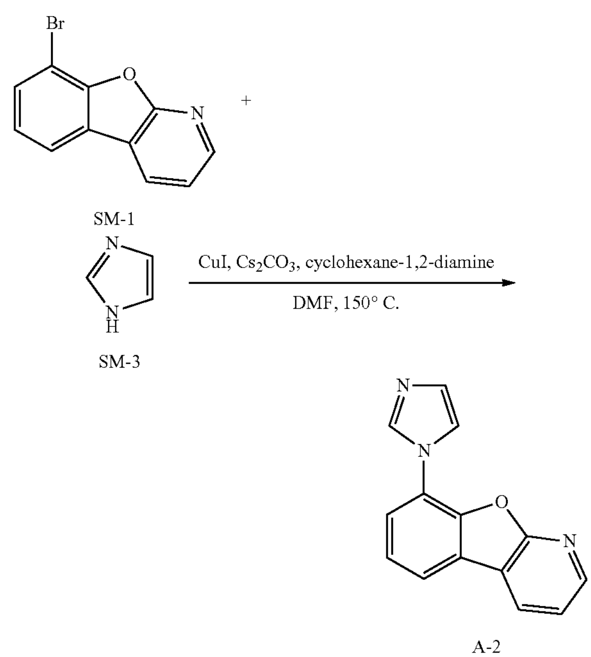

In a 1 L round bottom flask and under a nitrogen atmosphere, SM-1 (24.70 g, 0.10 mol), SM-3 (13.61 g, 0.20 mol), (1R,2R)-cyclohexane-1,2-diamine (22.83 g, 0.20 mol), copper(I) iodide (1.90 g, 0.01 mol), and cesium carbonate (97.75 g, 0.30 mol) were dissolved in 500 mL of DMF, followed by heating and stirring of a mixture overnight. When reaction of the mixture was completed, a reaction vessel was cooled to room temperature, and the mixture was filtered through a celite pad filter, and an organic layer was extracted and separated therefrom using ethyl acetate and distilled water. Moisture was removed from the organic layer using anhydrous magnesium sulfate, and the organic layer was filtered through a filter, and then concentrated under reduced pressure. A resulting crude product was recrystallized using ethyl acetate and hexane to obtain A-2 (17.87 g, 76%).

<Preparation of Ligand B-2>

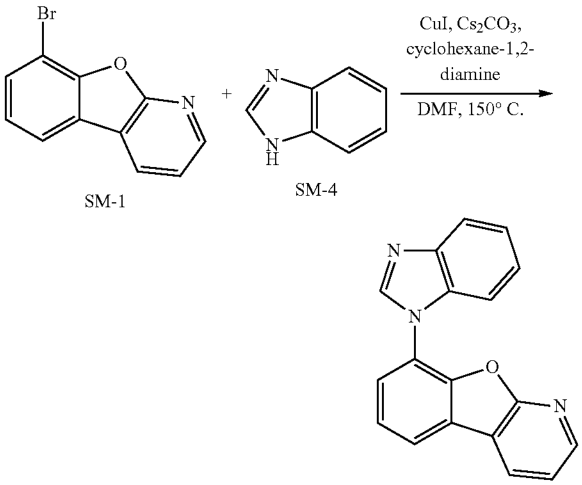

SM-1 SM-4

B-2

In a 1 L round bottom flask and under a nitrogen atmosphere, SM-1 (24.70 g, 0.10 mol), SM-4 (47.22 g, 0.20 mol), (1R,2R)-cyclohexane-1,2-diamine (22.83 g, 0.20 mol), copper(I) iodide (1.90 g, 0.01 mol), and cesium carbonate (97.75 g, 0.30 mol) were dissolved in 500 mL of DMF, followed by heating and stirring of a mixture overnight. When reaction of the mixture was completed, a reaction vessel was cooled to room temperature, and the mixture was filtered through a celite pad filter, and an organic layer was extracted and separated therefrom using ethyl acetate and distilled water. Moisture was removed from the organic layer using anhydrous magnesium sulfate, and the organic layer was filtered through a filter, and then concentrated under reduced pressure. A resulting crude product was recrystallized using ethyl acetate and hexane to obtain B-2 (17.40 g, 61%).

<Preparation of Ligand G-2>

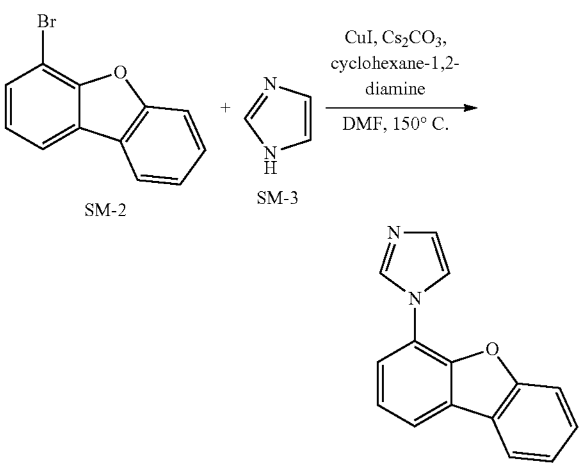

SM-2 SM-3

G-2

In a 1 L round bottom flask and under a nitrogen atmosphere, SM-2 (24.60 g, 0.10 mol), SM-3 (13.61 g, 0.20 mol), (1R,2R)-cyclohexane-1,2-diamine (22.83 g, 0.20 mol), copper(I) iodide (1.90 g, 0.01 mol), and cesium carbonate (97.75 g, 0.30 mol) were dissolved in 500 mL of DMF, followed by heating and stirring of a mixture overnight. When reaction of the mixture was completed, a reaction vessel was cooled to room temperature, and the mixture was filtered through a celite pad filter, and an organic layer was extracted and separated therefrom using ethyl acetate and distilled water. Moisture was removed from the organic layer using anhydrous magnesium sulfate, and the organic layer was filtered through a filter, and then concentrated under reduced pressure. A resulting crude product was recrystallized using ethyl acetate and hexane to obtain G-2 (19.19 g, 82%).

<Preparation of Ligand H-2>

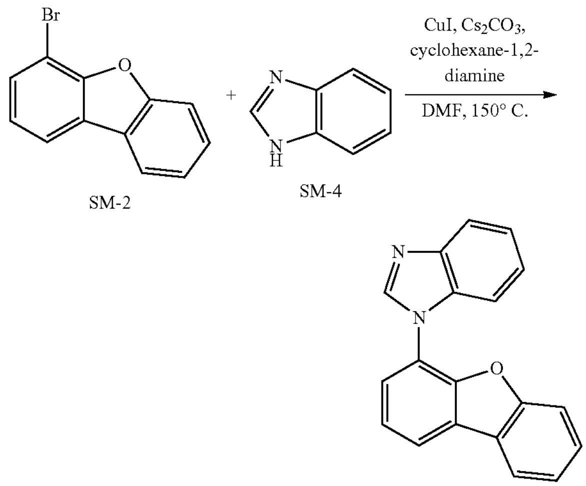

SM-2 SM-4

H-2

In a 1 L round bottom flask and under a nitrogen atmosphere, SM-2 (24.60 g, 0.10 mol), SM-4 (47.22 g, 0.20 mol), (1R,2R)-cyclohexane-1,2-diamine (22.83 g, 0.20 mol), copper(I) iodide (1.90 g, 0.01 mol), and cesium carbonate (97.75 g, 0.30 mol) were dissolved in 500 mL of DMF, followed by heating and stirring of a mixture overnight. When reaction of the mixture was completed, a reaction vessel was cooled to room temperature, and the mixture was filtered through a celite pad filter, and an organic layer was extracted and separated therefrom using ethyl acetate and distilled water. Moisture was removed from the organic layer using anhydrous magnesium sulfate, and the organic layer was filtered through a filter, and then concentrated under reduced pressure. A resulting crude product was recrystallized using ethyl acetate and hexane to obtain H-2 (20.74 g, 73%).

<Preparation of Ligand A-1>

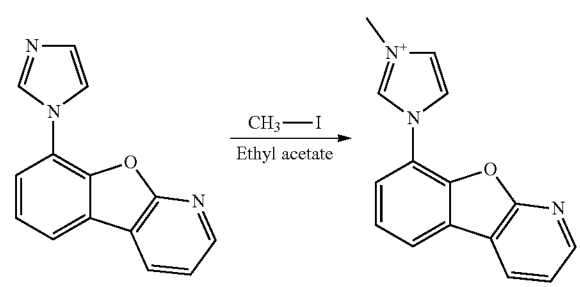

A-2 A-1

In a 500 mL round-bottom flask and under a nitrogen atmosphere, A-2 (11.75 g, 0.05 mol) was dissolved in 250 mL of ethyl acetate and then iodomethane (42.58 g, 0.30 mol) was sequentially added to a reaction solution and the reaction solution was stirred at room temperature for 24 hours. When the reaction thereof was completed, the reaction solution was filtered and concentrated under reduced pressure to obtain the compound A-1 (17.90 g, 85%).

<Preparation of Ligand B-1>

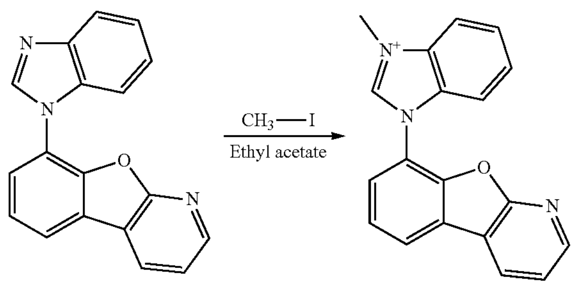

B-2

B-1

In a 500 mL round bottom flask and under a nitrogen atmosphere, B-2 (14.25 g, 0.05 mol) was dissolved in 250 mL of ethyl acetate and then iodomethane (42.58 g, 0.30 mol) was sequentially added to a reaction solution and the reaction solution was stirred at room temperature for 24 hours. When the reaction thereof was completed, the reaction solution was filtered and concentrated under reduced pressure to obtain the compound B-1 (19.55 g, 83%).

<Preparation of Ligand C-1>

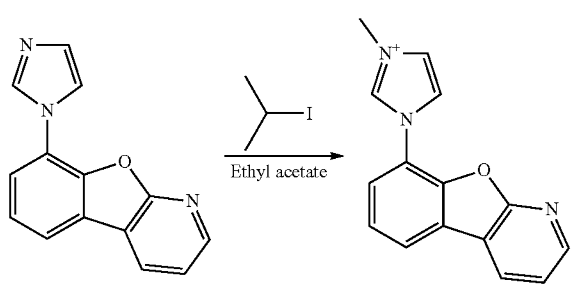

A-2

C-1

In a 500 mL round-bottom flask and under a nitrogen atmosphere, A-2 (11.75 g, 0.05 mol) was dissolved in 250 mL of ethyl acetate, and then 2-iodompropane (42.58 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound C-1 (17.51 g, 78%).

<Preparation of Ligand D-1>

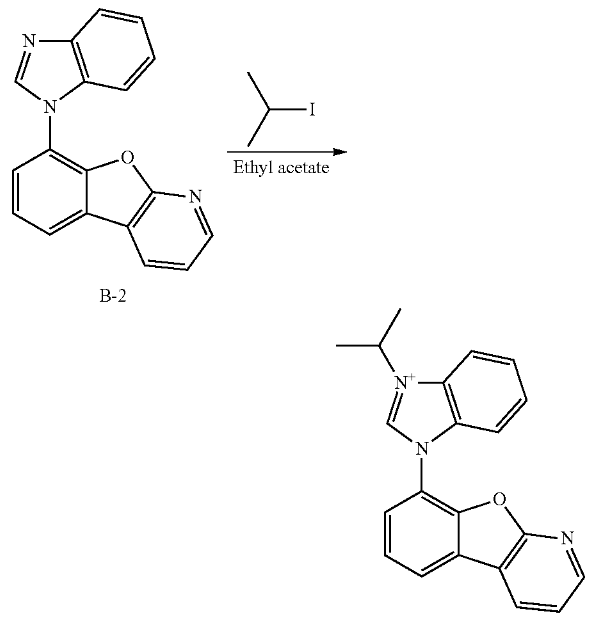

B-2

D-1

In a 500 mL round bottom flask and under a nitrogen atmosphere, B-2 (14.25 g, 0.05 mol) was dissolved in 250 mL of ethyl acetate and then 2-iodopropane (51.00 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound D-1 (20.46 g, 82%).

<Preparation of Ligand E-1>

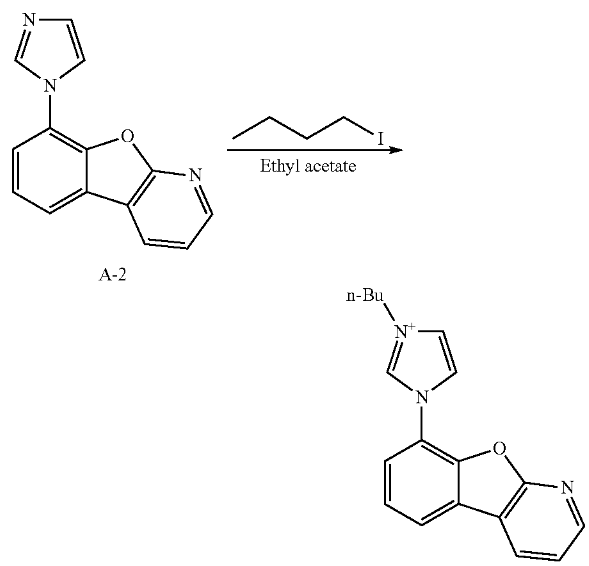

A-2

E-1

In a 500 mL round bottom flask and under a nitrogen atmosphere, A-2 (11.75 g, 0.05 mol) was dissolved in 250 mL of ethyl acetate and then 2-iodopropane (51.00 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound E-1 (18.52 g, 80%).

<Preparation of Ligand F-1>

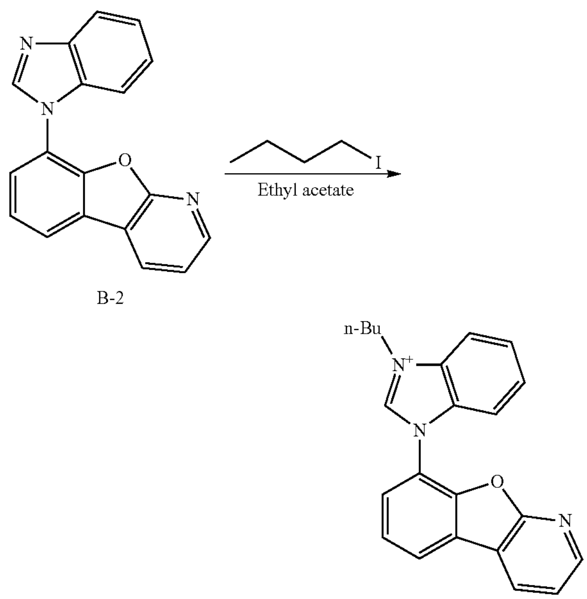

B-2

F-1

In a 500 mL round bottom flask and under a nitrogen atmosphere, B-2 (14.25 g, 0.05 mol) was dissolved in 250 mL of ethyl acetate and then 1-iodobutane (51.00 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound F-1 (21.55 g, 84%).

<Preparation of Ligand G-1>

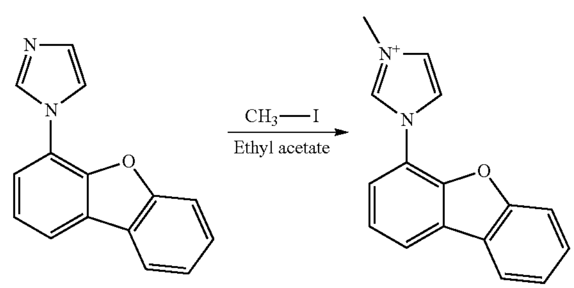

G-2

G-1

In a 500 mL round bottom flask and under a nitrogen atmosphere, G-2 (11.70 g, 0.05 mol) was dissolved in 250 mL of ethyl acetate and then, iodomethane (55.21 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound G-1 (18.70 g, 89%).

<Preparation of Ligand H-1>

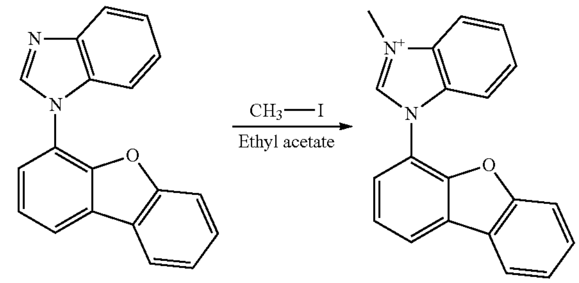

H-2

H-1

In a 500 mL round bottom flask and under a nitrogen atmosphere, H-2 (14.20 g, 0.05 mol) was dissolved in 250 mL of ethyl acetate and then iodomethane (55.21 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound H-1 (19.04 g, 81%).

<Preparation of Ligand I-1>

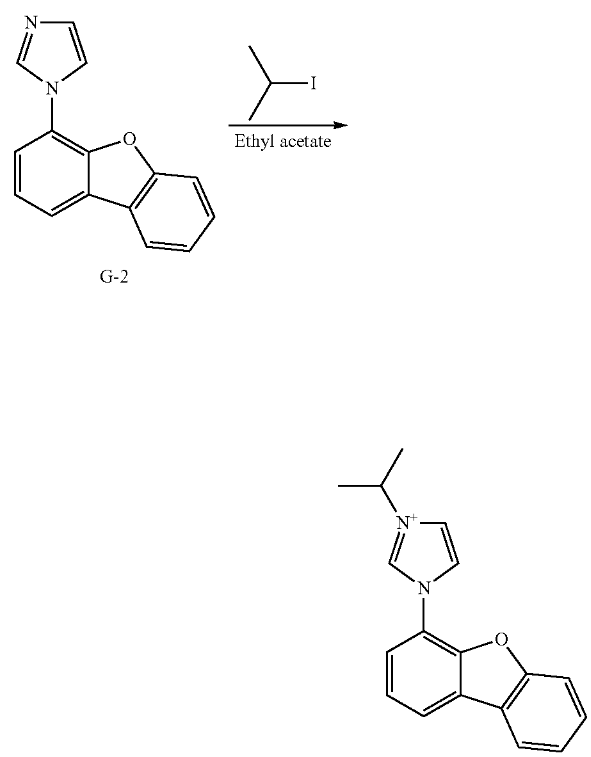

G-2

I-1

In a 500 mL round bottom flask and under a nitrogen atmosphere, G-2 (11.70 g, 0.05 mol) was dissolved in 250 mL of ethyl acetate and then, 2-iodopropane (55.21 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound I-1 (19.72 g, 88%).

<Preparation of Ligand J-1>

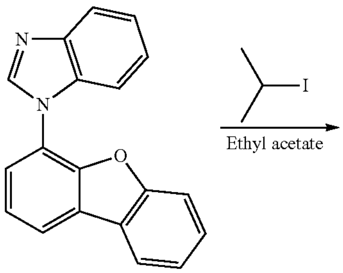

H-2

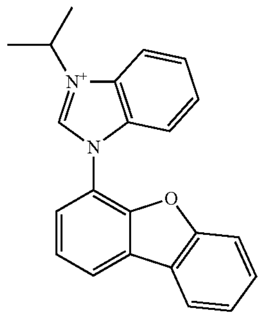

J-1

In a 500 mL round bottom flask and under a nitrogen atmosphere, H-2 (14.20 g, 0.05 mol) was dissolved in 250 mL of ethyl acetate and then 2-iodompropane (42.58 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound J-1 (22.42 g, 90%).

<Preparation of Ligand K-1>

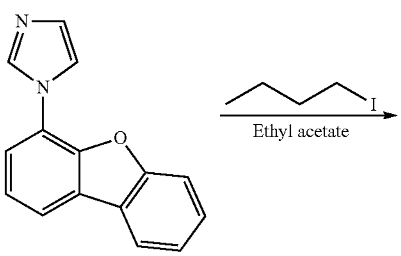

G-2

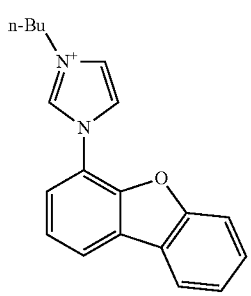

K-1

In a 500 mL round bottom flask and under a nitrogen atmosphere, G-2 (11.70 g, 0.05 mol) was dissolved in 250 mL of ethyl acetate and then 1-iodobutane (42.58 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound K-1 (19.64 g, 85%).

<Preparation of Ligand L-1>

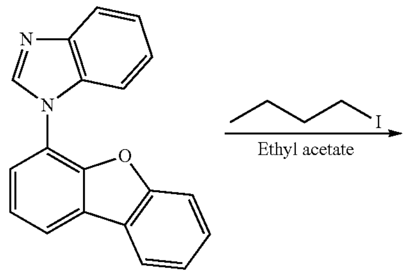

H-2

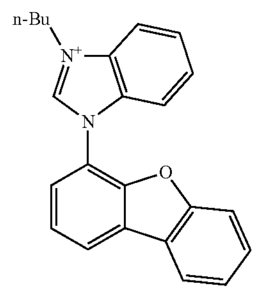

L-1

In a 500 mL round bottom flask and under a nitrogen atmosphere, H-2 (14.20 g, 0.05 mol) was dissolved in 250 mL of ethyl acetate and then 1-iodobutane (42.58 g, 0.30 mol) was sequentially added to a reaction solution and then, the reaction solution was stirred at room temperature for 24 hours. When the reaction thereof was completed, the reaction solution was filtered and concentrated under reduced pressure to obtain the compound L-1 (22.79 g, 89%).

Synthesis Example—Preparation of Ligand

<Preparation of Ligand A>

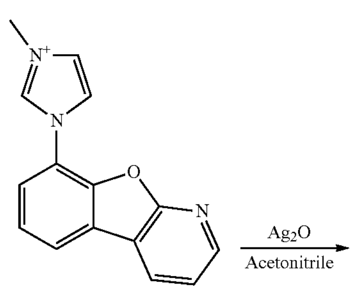

A-1

-continued

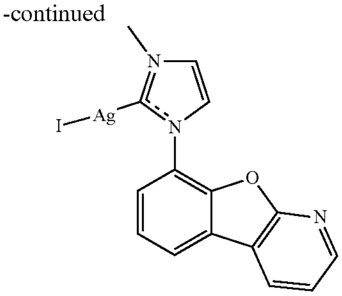

A

In a 500 mL round bottom flask and under a nitrogen atmosphere, the reactant A-1 (21.05 g, 0.05 mol) and silver oxide (5.80 g, 0.025 mol) were dissolved in 250 mL of acetonitrile and then a reaction solution was stirred at room temperature for 24 hours. When the reaction thereof was completed, the reaction solution was concentrated under reduced pressure to obtain the compound A (22.94 g, 95%), and further purification for a next reaction was not performed.

<Preparation of Ligand B>

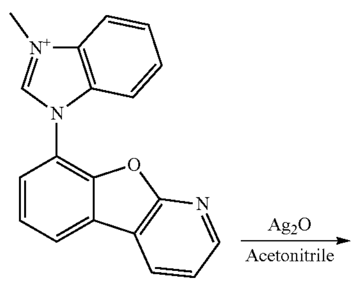

B-1

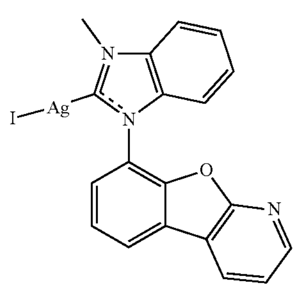

B

In a 500 mL round bottom flask and under a nitrogen atmosphere, the reactant B-1 (23.55 g, 0.05 mol) and silver oxide (5.80 g, 0.025 mol) were dissolved in 250 mL of acetonitrile and then a reaction solution was stirred at room temperature for 24 hours. Upon completion of the reaction thereof, the reaction solution was concentrated under reduced pressure to obtain the compound B (24.51 g, 92%), and further purification for a next reaction was not performed.

<Preparation of Ligand C>

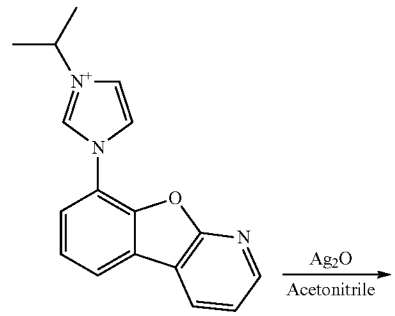

C-1

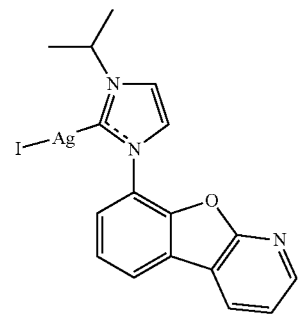

C

In a 500 mL round bottom flask and under a nitrogen atmosphere, the reactant C-1 (22.46 g, 0.05 mol) and silver oxide (5.80 g, 0.025 mol) were dissolved in 250 mL of acetonitrile and then a reaction solution was stirred at room temperature for 24 hours. When the reaction thereof was completed, the reaction solution was concentrated under reduced pressure to obtain the compound C (22.74 g, 89%), and further purification for a next reaction was not performed.

<Preparation of Ligand D>

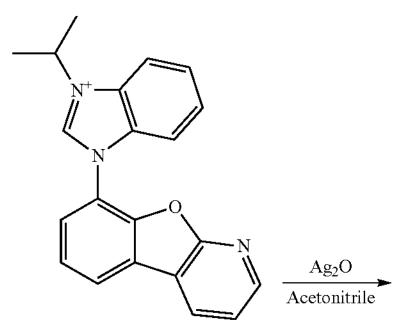

D-1

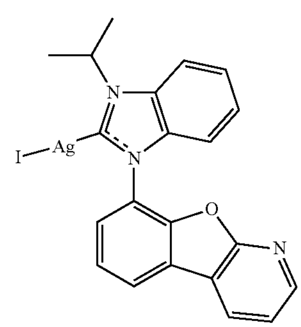

D

In a 500 mL round bottom flask and under a nitrogen atmosphere, the reactant D-1 (24.96 g, 0.05 mol) and silver oxide (5.80 g, 0.025 mol) were dissolved in 250 mL of acetonitrile and then a reaction solution was stirred at room temperature for 24 hours. When the reaction thereof was completed, the reaction solution was concentrated under reduced pressure to obtain the compound D (23.56 g, 84%), and further purification for a next reaction was not performed.

<Preparation of Ligand E>

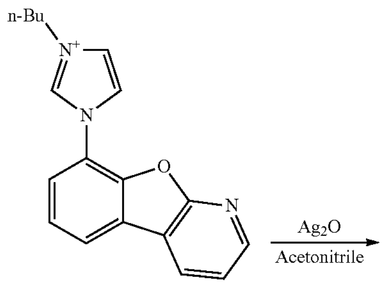

E-1

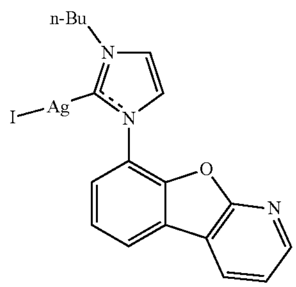

E

In a 500 mL round bottom flask and under a nitrogen atmosphere, the reactant E-1 (23.16 g, 0.05 mol) and silver oxide (5.80 g, 0.025 mol) were dissolved in 250 mL of acetonitrile and then a reaction solution was stirred at room temperature for 24 hours. When the reaction thereof was completed, the reaction solution was concentrated under reduced pressure to obtain the compound E (23.86 g, 91%), and further purification for a next reaction was not performed.

<Preparation of Ligand F>

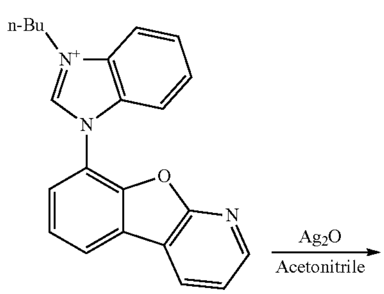

F-1

-continued

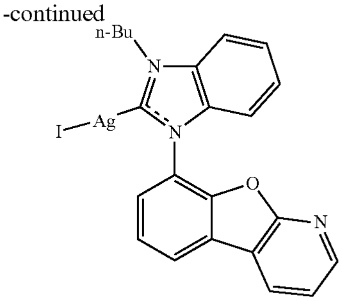

F

In a 500 mL round bottom flask and under a nitrogen atmosphere, the reactant F-1 (25.66 g, 0.05 mol) and silver oxide (5.80 g, 0.025 mol) were dissolved in 250 mL of acetonitrile and then a reaction solution was stirred at room temperature for 24 hours. Upon completion of the reaction thereof, the reaction solution was concentrated under reduced pressure to obtain the compound F (26.45 g, 92%), and further purification for a next reaction was not performed.

<Preparation of Ligand G>

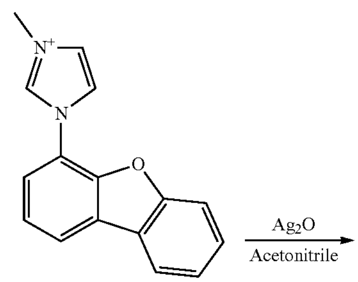

G-1

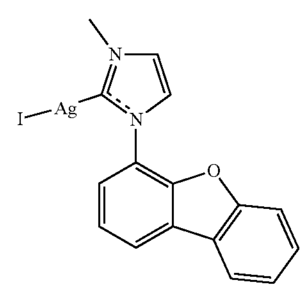

G

In a 500 mL round bottom flask and under a nitrogen atmosphere, the reactant G-1 (21.00 g, 0.05 mol) and silver oxide (5.80 g, 0.025 mol) were dissolved in 250 mL of acetonitrile and then a reaction solution was stirred at room temperature for 24 hours. When the reaction thereof was completed, the reaction solution was concentrated under reduced pressure to obtain the compound G (20.24 g, 84%), and further purification for a next reaction was not performed.

<Preparation of Ligand H>

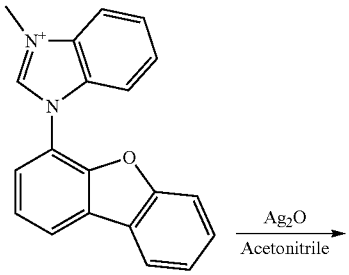

H-1

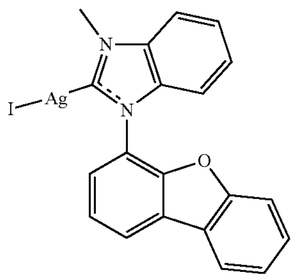

H

In a 500 mL round bottom flask and under a nitrogen atmosphere, the reactant H-1 (23.50 g, 0.05 mol) and silver oxide (5.80 g, 0.025 mol) were dissolved in 250 mL of acetonitrile and then a reaction solution was stirred at room temperature for 24 hours. When the reaction thereof was completed, the reaction solution was concentrated under reduced pressure to obtain the compound H (23.14 g, 89%), and further purification for a next reaction was not performed.

<Preparation of Ligand I>

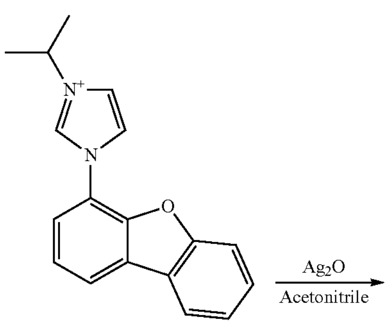

I-1

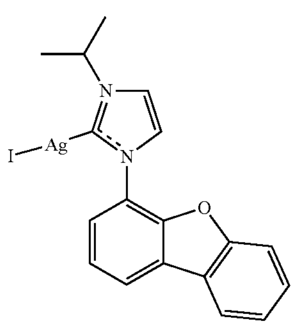

I

In a 500 mL round bottom flask and under a nitrogen atmosphere, the reactant I-1 (22.41 g, 0.05 mol) and silver oxide (5.80 g, 0.025 mol) were dissolved in 250 mL of acetonitrile and then a reaction solution was stirred at room temperature for 24 hours. Upon completion of the reaction thereof, the reaction solution was concentrated under reduced pressure to obtain the compound I (22.95 g, 90%), and further purification for a next reaction was not performed.

<Preparation of Ligand J>

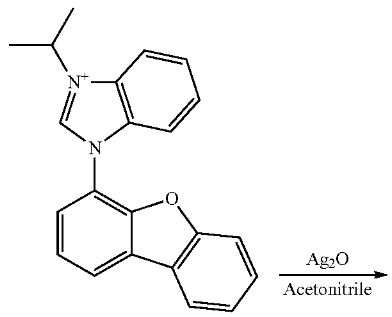

J-1

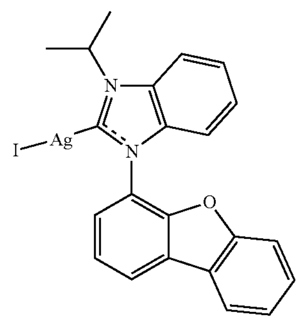

J

In a 500 mL round bottom flask and under a nitrogen atmosphere, the reactant J-1 (24.91 g, 0.05 mol) and silver oxide (5.80 g, 0.025 mol) were dissolved in 250 mL of acetonitrile and then a reaction solution was stirred at room temperature for 24 hours. When the reaction thereof was completed, the reaction solution was concentrated under reduced pressure to obtain the compound J (25.48 g, 91%), and further purification for a next reaction was not performed.

<Preparation of Ligand K>

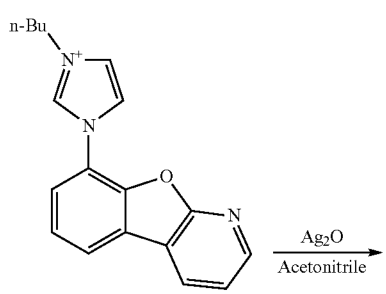

K-1

-continued

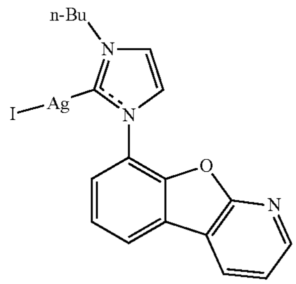

K

In a 500 mL round bottom flask and under a nitrogen atmosphere, the reactant K-1 (23.11 g, 0.05 mol) and silver oxide (5.80 g, 0.025 mol) were dissolved in 250 mL of acetonitrile and then a reaction solution was stirred at room temperature for 24 hours. Upon completion of the reaction thereof, the reaction solution was concentrated under reduced pressure to obtain the compound K (24.89 g, 95%), and further purification for a next reaction was not performed.

<Preparation of Ligand L>

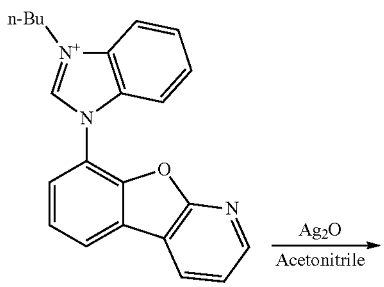

L-1

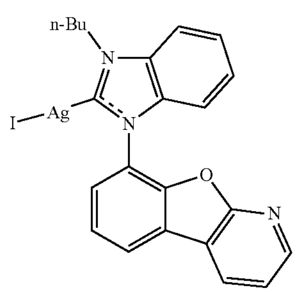

L

In a 500 mL round bottom flask and under a nitrogen atmosphere, the reactant L-1 (25.61 g, 0.05 mol) and silver oxide (5.80 g, 0.025 mol) were dissolved in 250 mL of acetonitrile and then a reaction solution was stirred at room temperature for 24 hours. When the reaction thereof was completed, the reaction solution was concentrated under reduced pressure to obtain the compound L (26.98 g, 94%), and further purification for a next reaction was not performed.

Synthesis Example—Preparation of Iridium Compound

<Preparation of Iridium Compound 1>

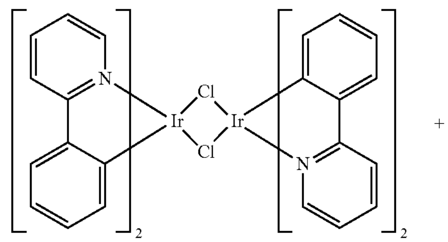

M1

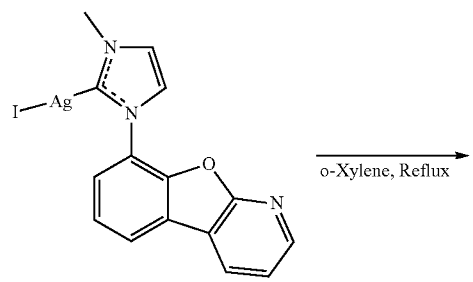

A

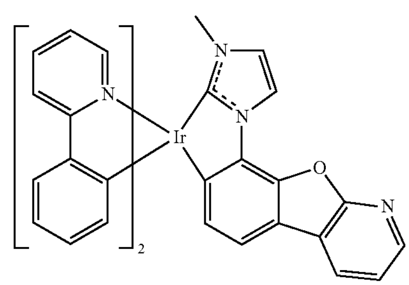

1

In a 150 mL round bottom flask and under a nitrogen atmosphere, iridium precursor M1 (1.61 g, 1.5 mmol) and the ligand A (1.45 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 1 (1.68 g, 75%).

<Preparation of Iridium Compound 2>

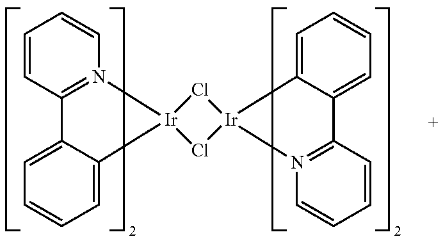

M1

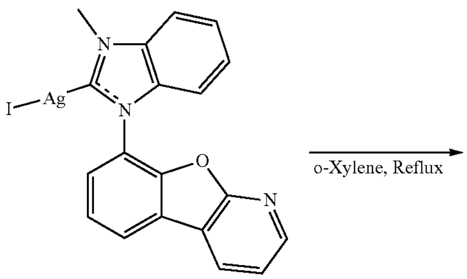

B

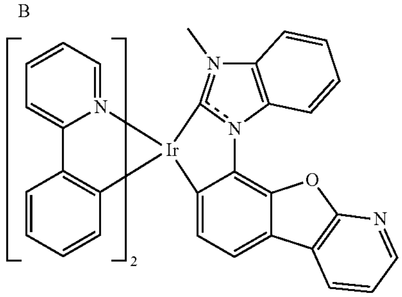

2

In a 150 mL round bottom flask and under a nitrogen atmosphere, iridium precursor M1 (1.61 g, 1.5 mmol) and the ligand B (1.60 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 2 (1.63 g, 68%).

<Preparation of Iridium Compound 16>

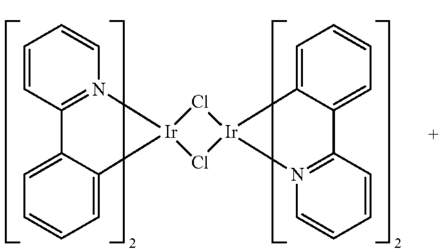

M1

-continued

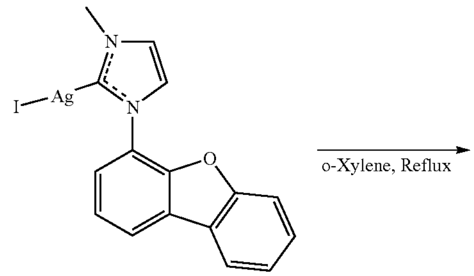

C

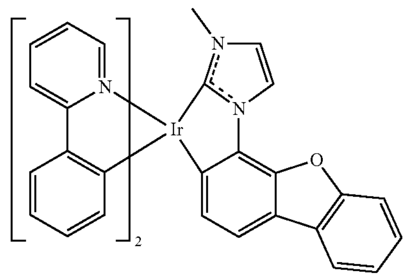

16

In a 150 mL round bottom flask and under a nitrogen atmosphere, iridium precursor M1 (1.61 g, 1.5 mmol) and the ligand G (1.46 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 16 (1.57 g, 70%).

<Preparation of Iridium Compound 17>

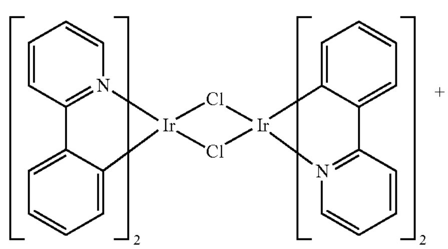

M1

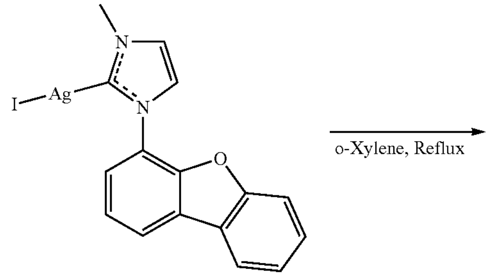

H

-continued

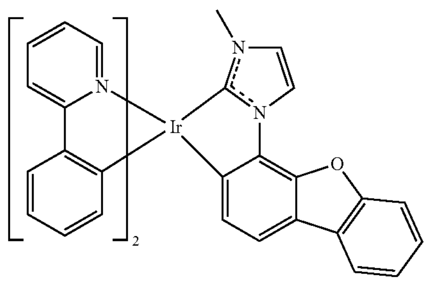

17

In a 150 mL round bottom flask and under a nitrogen atmosphere, iridium precursor M1 (1.61 g, 1.5 mmol) and the ligand H (1.60 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 17 (1.94 g, 81%).

<Preparation of Iridium Compound 91>

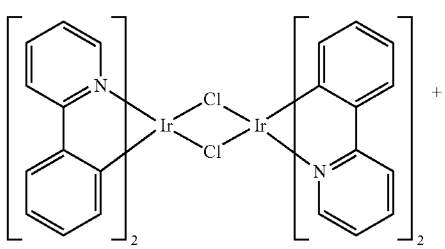

M1

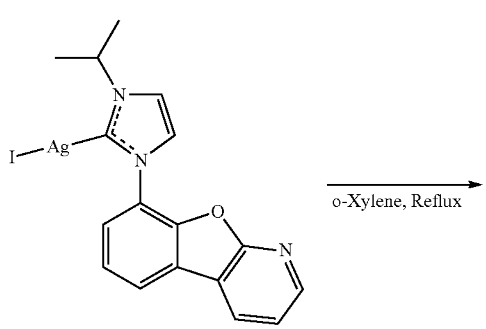

C

-continued

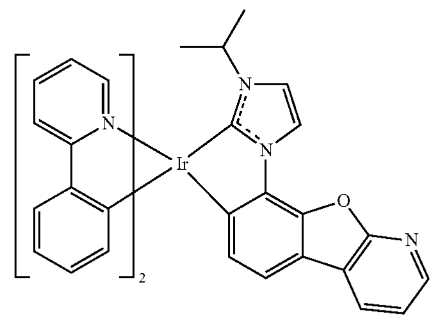

91

In a 150 mL round bottom flask and under a nitrogen atmosphere, iridium precursor M1 (1.61 g, 1.5 mmol) and the ligand C (1.53 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 91 (1.89 g, 81%).

<Preparation of Iridium Compound 92>

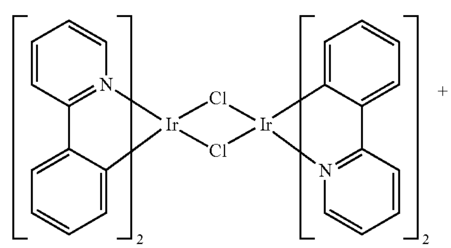

M1

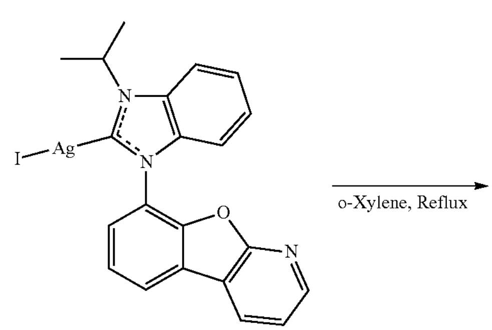

D

-continued

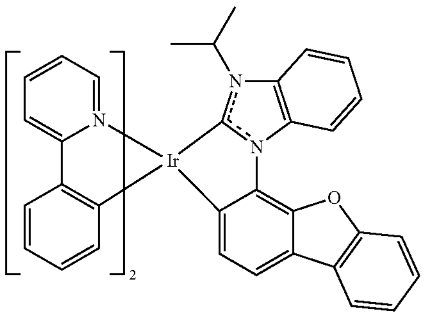

92

In a 150 mL round bottom flask and under a nitrogen atmosphere, iridium precursor M1 (1.61 g, 1.5 mmol) and the ligand D (1.68 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 92 (1.87 g, 76%).

<Preparation of Iridium Compound 106>

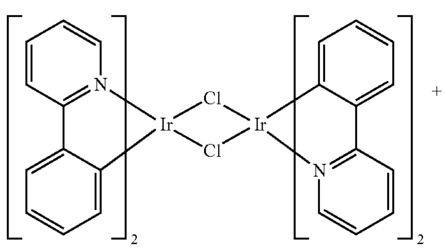

M1

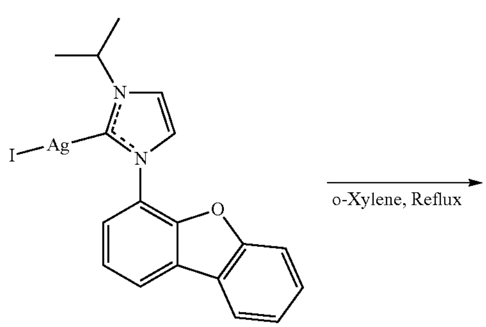

I

-continued

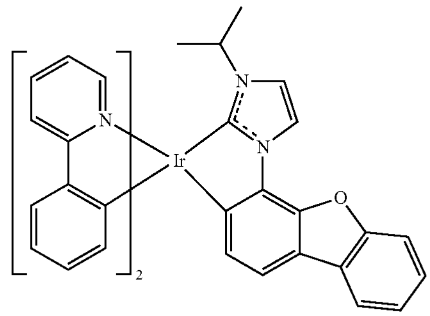

106

In a 150 mL round bottom flask and under a nitrogen atmosphere, iridium precursor M1 (1.61 g, 1.5 mmol) and the ligand I (1.53 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 106 (1.75 g, 75%).

<Preparation of Iridium Compound 107>

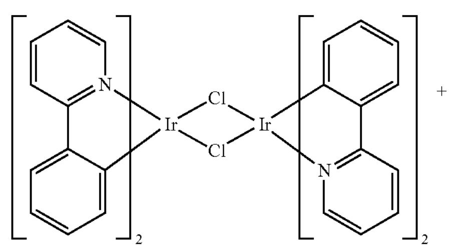

M1

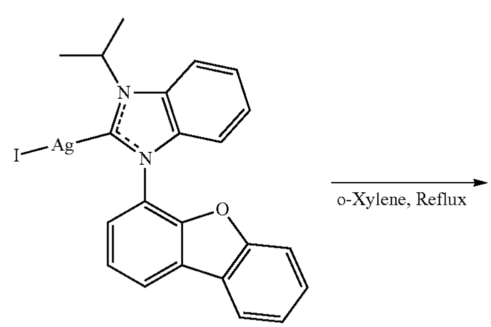

J

-continued

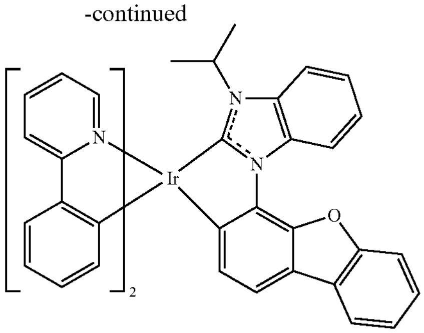

107

In a 150 mL round bottom flask and under a nitrogen atmosphere, iridium precursor M1 (1.61 g, 1.5 mmol) and the ligand J (1.68 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 107 (1.69 g, 68%).

<Preparation of Iridium Compound 181>

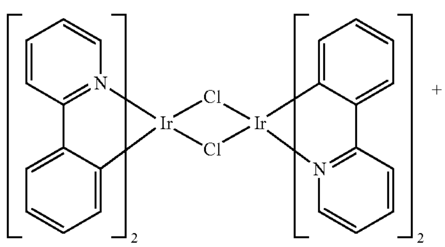

M1

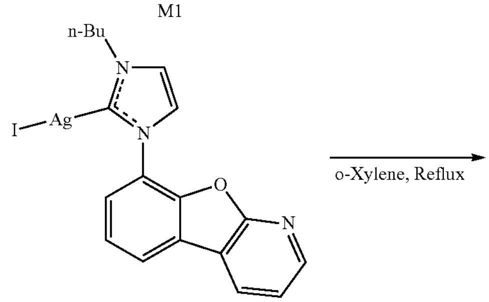

E

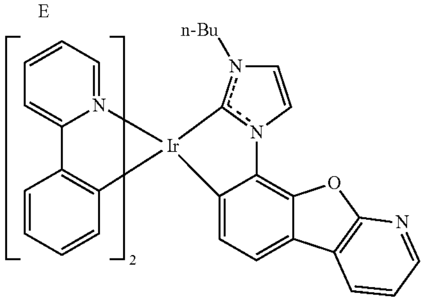

181

In a 150 mL round bottom flask and under a nitrogen atmosphere, iridium precursor M1 (1.61 g, 1.5 mmol) and the ligand E (1.57 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 181 (1.90 g, 80%).

<Preparation of Iridium Compound 182>

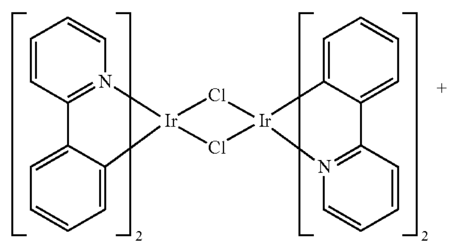

M1

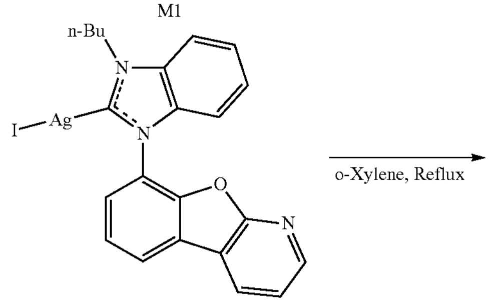

F

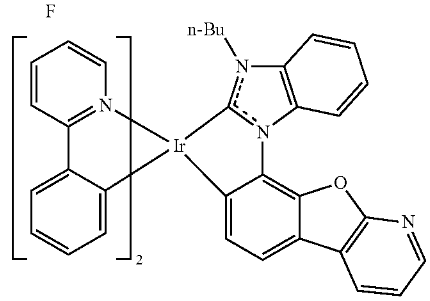

182

In a 150 mL round bottom flask and under a nitrogen atmosphere, iridium precursor M1 (1.61 g, 1.5 mmol) and the ligand F (1.72 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 182 (1.64 g, 65%).

<Preparation of Iridium Compound 196>

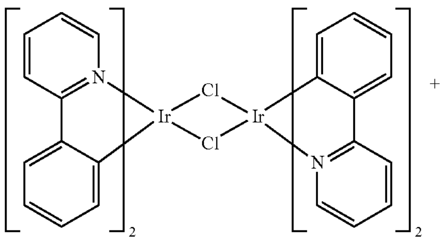

M1

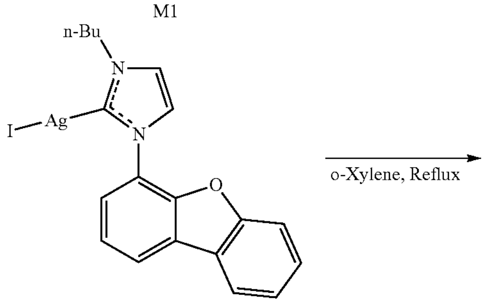

K

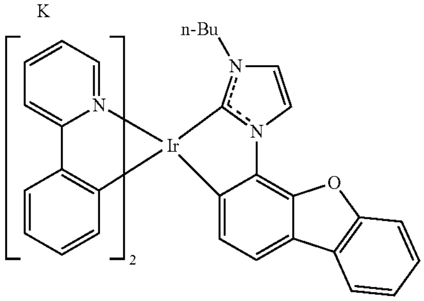

196

In a 150 mL round bottom flask and under a nitrogen atmosphere, iridium precursor M1 (1.61 g, 1.5 mmol) and the ligand K (1.57 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 196 (1.87 g, 79%).

<Preparation of Iridium Compound 197>

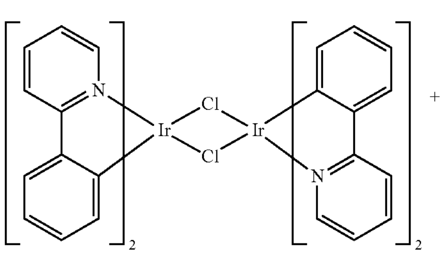

M1

-continued

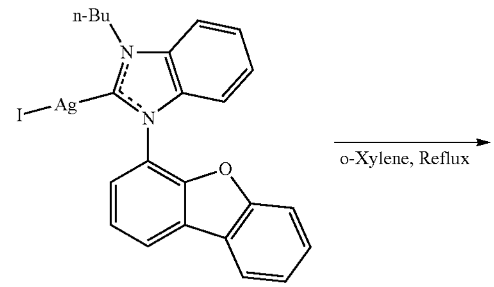

L

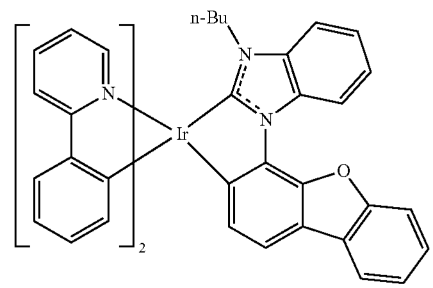

197

In a 150 mL round bottom flask and under a nitrogen atmosphere, iridium precursor M1 (1.61 g, 1.5 mmol) and the ligand L (1.72 g, 3 mmol) were dissolved in o-xylene (150 mL) and a reaction solution was stirred under reflux for 18 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of ethylacetate:hexane=25:75 to obtain the above iridium compound 197 (1.87 g, 74%).

<Preparation of Iridium Compound 466>

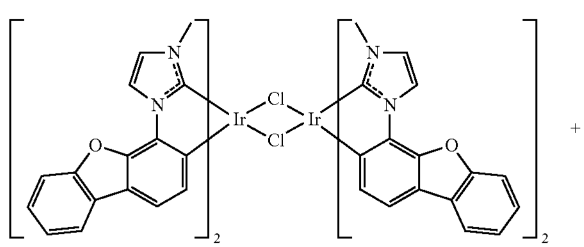

M2

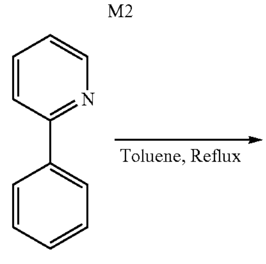

L1

-continued

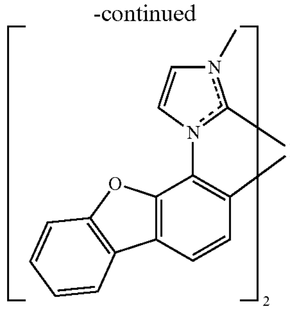

466

In a 250 mL round bottom flask and under a nitrogen atmosphere, iridium precursor M2 (2.17 g, 1.5 mmol) and the ligand L1 (0.47 g, 3 mmol) were dissolved in toluene (100 mL) and a reaction solution was stirred under reflux for 24 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of toluene:hexane=1:1 to obtain the above iridium compound 466 (1.82 g, 72%).

<Preparation of Iridium Compound 468>

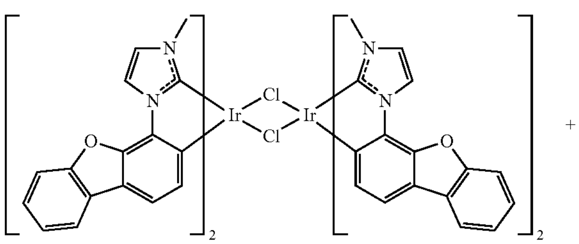

M2

-continued

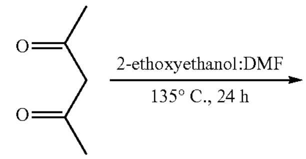

L2

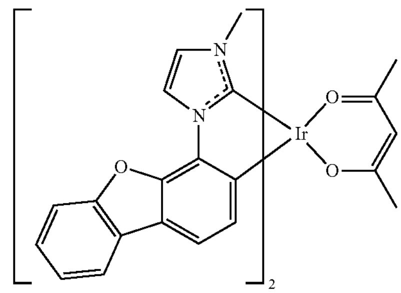

468

In a 150 mL round bottom flask and under a nitrogen atmosphere, iridium precursor M2 (2.17 g, 1.5 mmol) and the ligand L2 (0.30 g, 3 mmol) were dissolved in a mixed solvent (2-ethoxyethanol:DMF=40 mL:40 mL) and a reaction solution was stirred under reflux for 24 hours at 135° C. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of toluene:hexane=1:3 to obtain the above iridium compound 468 (1.39 g, 59%).

<Preparation of Iridium Compound 470>

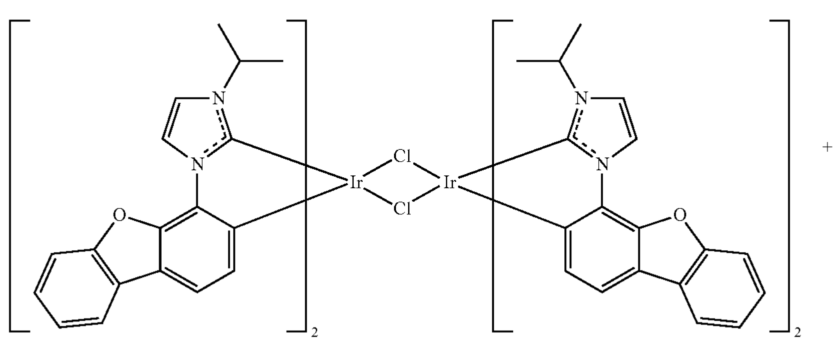

M3

-continued

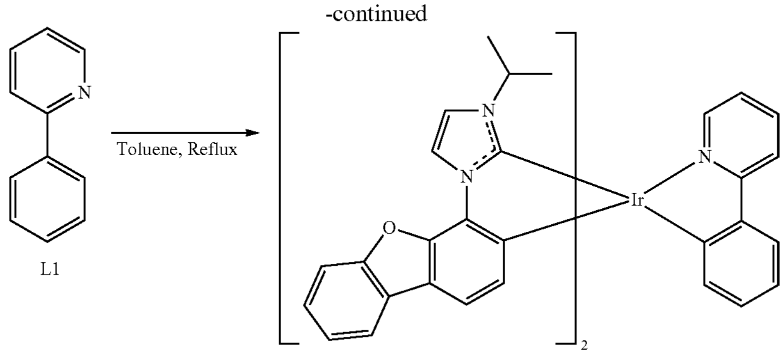

L1

476

In a 250 mL round bottom flask and under a nitrogen atmosphere, iridium precursor M3 (2.33 g, 1.5 mmol) and the ligand L1 (0.47 g, 3 mmol) were dissolved in toluene (100 mL) and a reaction solution was stirred under reflux for 24 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of toluene:hexane=1:1 to obtain the above iridium compound 470 (1.42 g, 53%).

<Preparation of Iridium Compound 472>

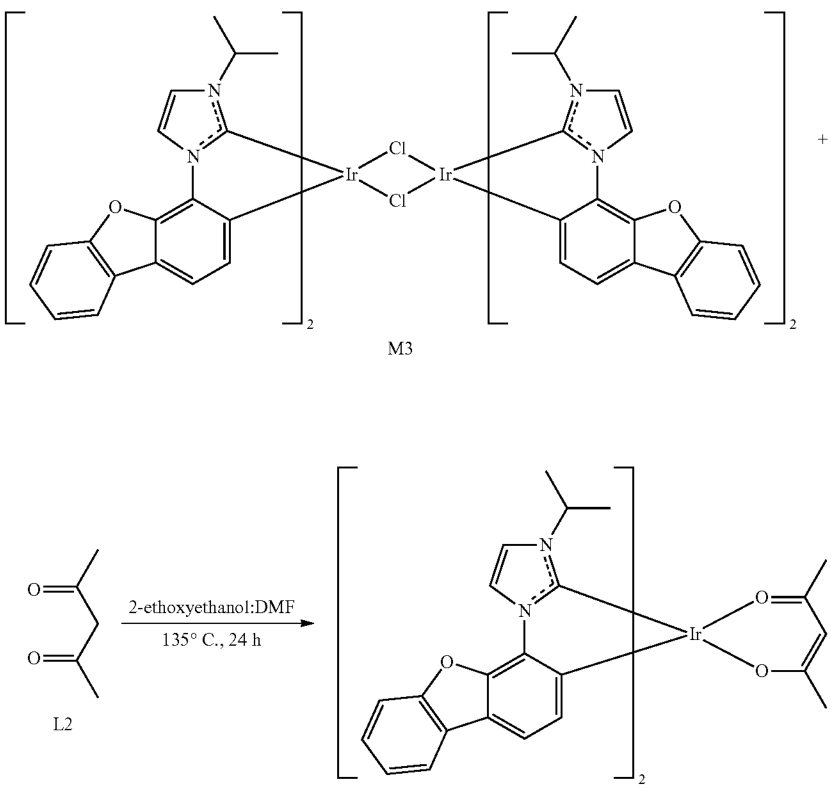

M3

L2

472

In a 150 mL round bottom flask and under a nitrogen atmosphere, iridium precursor M3 (2.33 g, 1.5 mmol) and the ligand L2 (0.30 g, 3 mmol) were dissolved in a mixed solvent (2-ethoxyethanol:DMF=40 mL:40 mL) and a reaction solution was stirred under reflux for 24 hours at 135° C. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of toluene:hexane=1:3 to obtain the above iridium compound 472 (1.82 g, 72%).

<Preparation of Iridium Compound 474>

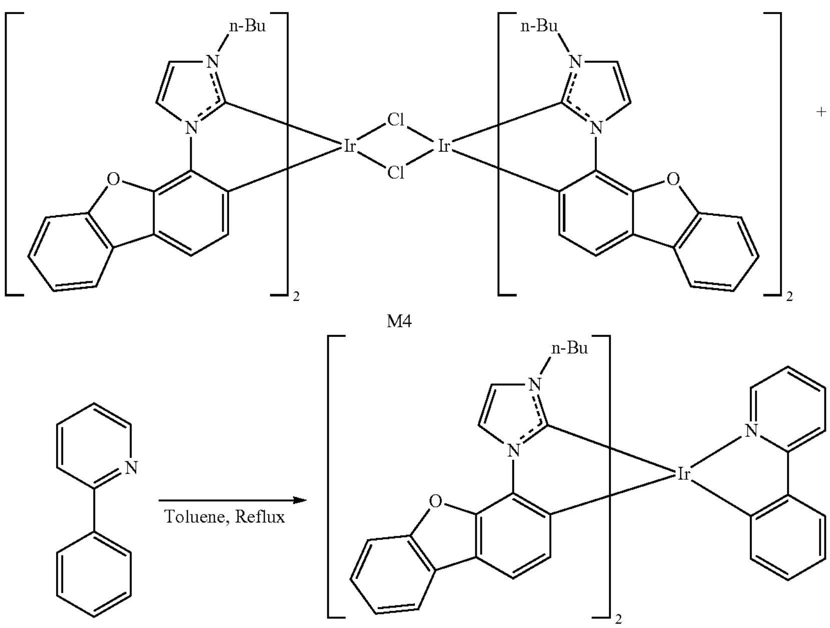

M4

L1

474

In a 250 mL round bottom flask and under a nitrogen atmosphere, iridium precursor M4 (2.42 g, 1.5 mmol) and the ligand L1 (0.47 g, 3 mmol) were dissolved in toluene (100 mL) and a reaction solution was stirred under reflux for 24 hours. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of toluene:hexane=1:1 to obtain the above iridium compound 474 (1.75 g, 63%).

<Preparation of Iridium Compound 476>

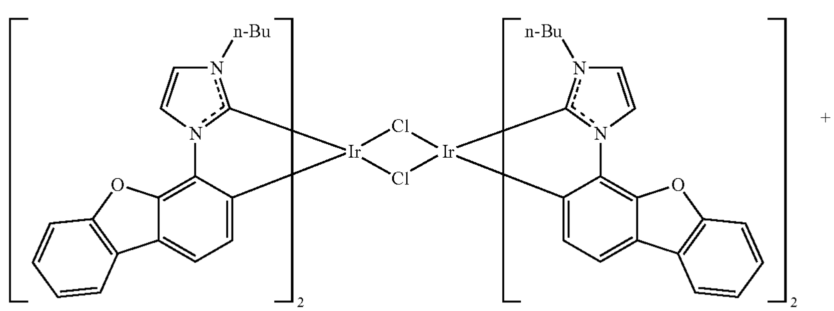

M4

-continued

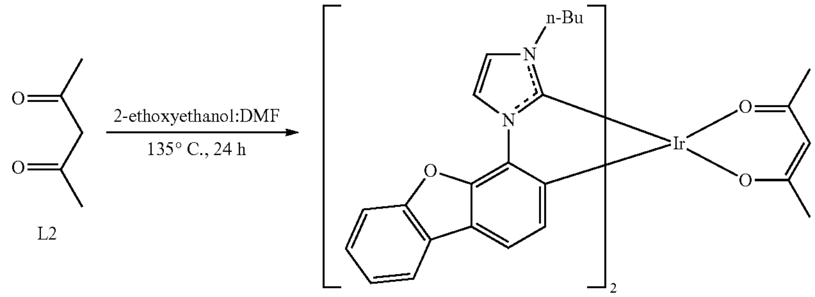

L2

476

In a 150 mL round bottom flask and under a nitrogen atmosphere, iridium precursor M4 (2.42 g, 1.5 mmol) and the ligand L2 (0.30 g, 3 mmol) were dissolved in a mixed solvent (2-ethoxyethanol:DMF=40 mL:40 mL) and a reaction solution was stirred under reflux for 24 hours at 135° C. When the reaction thereof was completed, a temperature was lowered to room temperature. Then, an organic layer was extracted therefrom using dichloromethane and distilled water, and moisture was removed therefrom by adding anhydrous magnesium sulfate thereto. A filtrate was obtained through filtration thereof and was depressurized to obtain a resulting crude product. The resulting crude product was purified using column chromatography under a condition of toluene:hexane=1:3 to obtain the above iridium compound 476 (1.77 g, 68%).

PRESENT EXAMPLES

Present Example 1

A glass substrate having a thin film made of ITO (indium tin oxide) of a thickness of 1,000 Å coated thereon was washed and was subjected to ultrasonic cleaning using acetone and was dried. HI-1 (N1,N1'-([1,1'-biphenyl]-4,4'-diyl)bis(N1,N4,N4-triphenylbenzene-1,4-diamine)) of a following structure as a hole injection material of a thickness of 60 nm was formed on the prepared ITO transparent electrode via thermal vacuum deposition. NPB as a hole transport material was thermally vacuum deposited to have a thickness of 80 nm on the hole injection layer. A light-emitting layer was thermally vacuum deposited on the hole transport material. In this regard, the light-emitting layer contains CBP of a following structure as a host material and the compound 1 as the dopant. A doping concentration was 5% and a thickness of the light emission layer was 30 nm. ET-1:Liq (1:1) (30 nm) as materials for the electron transport layer and the electron injection layer was thermally vacuum deposited on the light-emitting layer. Then, 100 nm thick aluminum was deposited thereon to form a negative electrode. Thus, an organic light-emitting diode was fabricated. The materials used in above Present Example 1 are as follows.

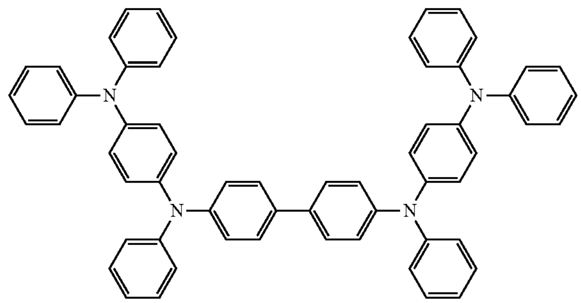

HI-1

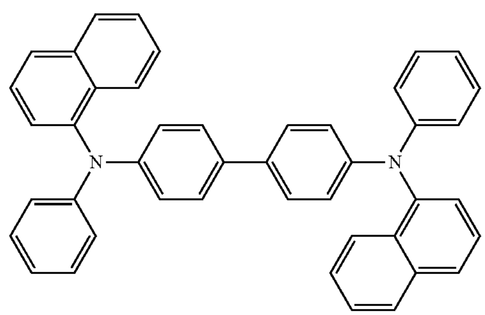

NPB

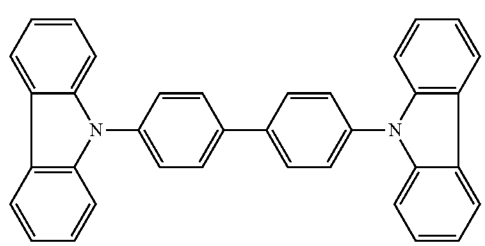

CBP

-continued

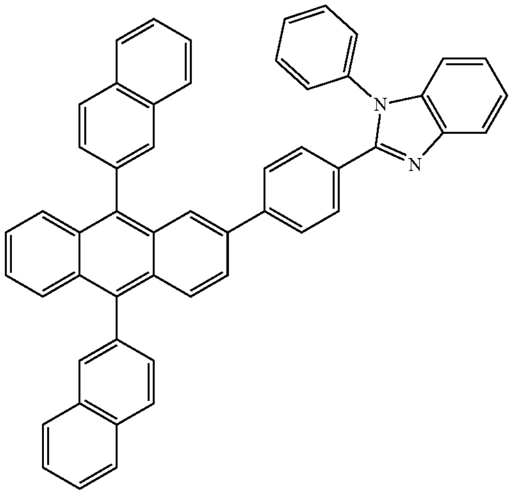

ET-1

-continued

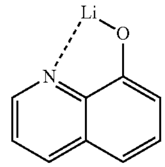

Liq

HI-1 means N1,N1'-([1,1'-biphenyl]-4,4'-diyl)bis(N1,N4,N4-triphenylbenzene-1,4-diamine).

ET-1 Means 2-(4-(9,10-di(naphthalen-2-yl) anthracen-2-yl)phenyl)-1H-benzo[d]imidazole.

Present Examples 2 to 12 and Comparative Examples 1 to 5

An organic light-emitting diode of each of Present Examples 2 to 12 and Comparative Examples 1 to 5 was manufactured in the same manner as in Present Example 1, except that each of compounds shown in a following Table 2 was used instead of the compound 1 as the dopant in Present Example 1.

TABLE 2

| Examples | Dopant | Operation voltage (V) | Maximum Luminous Quantum Efficiency (%, relative value) | EQE (%, relative value) | LT95 (%, relative value) |
|---|---|---|---|---|---|
| Comparative Example 1 | Ref-1 | 4.25 | 100 | 100 | 100 |
| Comparative Example 2 | Ref-2 | 4.31 | 106 | 108 | 104 |
| Comparative Example 3 | Ref-3 | 4.43 | 102 | 106 | 101 |
| Comparative Example 4 | Ref-4 | 4.28 | 108 | 108 | 105 |
| Comparative Example 5 | Ref-5 | 4.27 | 110 | 109 | 107 |
| Present Example 1 | Compound 1 | 4.24 | 128 | 126 | 124 |
| Present Example 2 | Compound 2 | 4.25 | 130 | 129 | 128 |
| Present Example 3 | Compound 16 | 4.23 | 132 | 130 | 128 |
| Present Example 4 | Compound 17 | 4.22 | 130 | 128 | 126 |
| Present Example 5 | Compound 91 | 4.21 | 132 | 131 | 128 |
| Present Example 6 | Compound 92 | 4.21 | 134 | 132 | 130 |
| Present Example 7 | Compound 106 | 4.23 | 136 | 134 | 132 |
| Present Example 8 | Compound 107 | 4.22 | 134 | 133 | 131 |
| Present Example 9 | Compound 181 | 4.20 | 133 | 131 | 128 |
| Present Example 10 | Compound 182 | 4.23 | 135 | 133 | 130 |
| Present Example 11 | Compound 196 | 4.20 | 140 | 136 | 132 |
| Present Example 12 | Compound 197 | 4.21 | 139 | 135 | 130 |

Structures of Ref-1 to Ref-5 as dopant materials of Comparative Examples 1 to 5 in Table 2 are as follows.

Ref-1

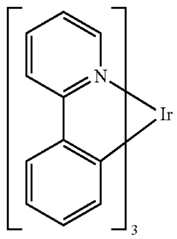

Ref-2

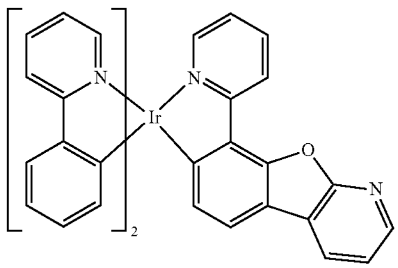

Ref-3

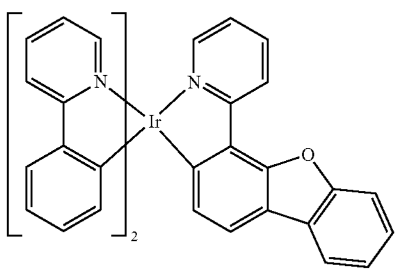

-continued

Ref-4

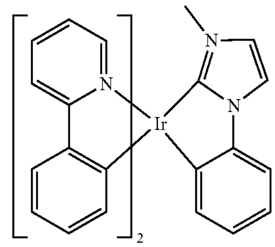

Ref-5

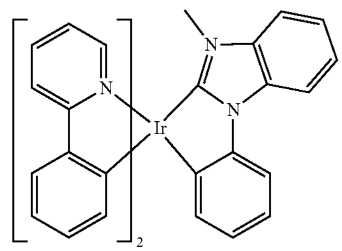

Present Examples 13 to 18 and Comparative Examples 6 to 10

An organic light-emitting diode of each of Present Examples 13 to 18 and Comparative Examples 6 to 10 was manufactured in the same manner as in Present Example 1, except that each of compounds shown in a following Table 3 was used instead of the compound 1 as the dopant in Present Example 1.

TABLE 3

| Examples | Dopant | Operation voltage (V) | Maximum Luminous Quantum Efficiency (%, relative value) | EQE (%, relative value) | LT95 (%, relative value) |
|---|---|---|---|---|---|
| Comparative Example 6 | Ref-6 | 4.25 | 100 | 100 | 100 |
| Comparative Example 7 | Ref-7 | 4.24 | 105 | 103 | 106 |
| Comparative Example 8 | Ref-8 | 4.34 | 108 | 107 | 95 |
| Comparative Example 9 | Ref-9 | 4.27 | 109 | 107 | 108 |
| Comparative Example 10 | Ref-10 | 4.26 | 111 | 108 | 109 |
| Present Example 13 | Compound 466 | 4.26 | 126 | 124 | 126 |
| Present Example 14 | Compound 468 | 4.28 | 124 | 123 | 121 |
| Present Example 15 | Compound 470 | 4.25 | 123 | 122 | 118 |
| Present Example 16 | Compound 472 | 4.23 | 122 | 120 | 124 |
| Present Example 17 | Compound 474 | 4.25 | 125 | 122 | 126 |
| Present Example 18 | Compound 476 | 4.21 | 127 | 124 | 127 |

Structures of Ref-6 to Ref-10 as dopant materials of Comparative Examples 6 to 10 in Table 3 are as follows.

Ref-6

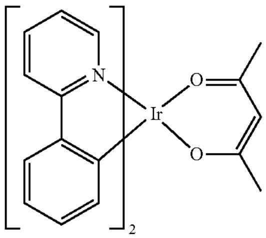

Ref-7

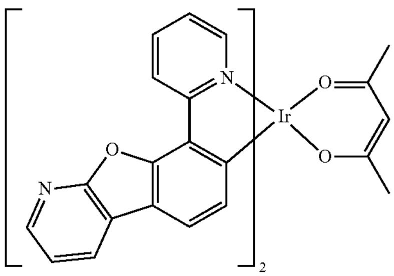

Ref-8

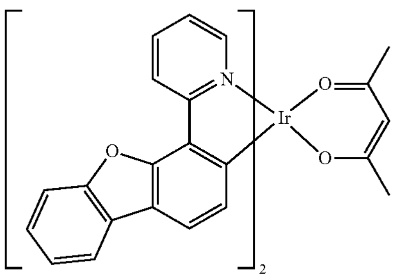

-continued

Ref-9

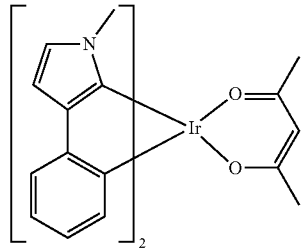

Ref-10

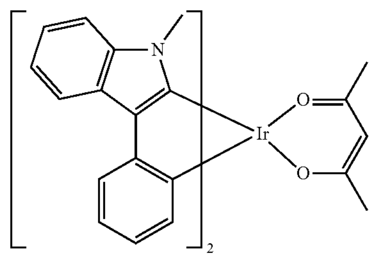

Present Examples 19 to 23

An organic light-emitting diode of each of Present Examples 19 to 23 was manufactured in the same manner as in Present Example 1 except that each of compounds shown in a following Table 4 was used instead of CBP as the host in Present Example 1.

TABLE 4

| Examples | Dopant | Host | Operation voltage (V) | Maximum Luminous Quantum Efficiency (%, relative value) | EQE (%, relative value) | LT95 (%, relative value) |
|---|---|---|---|---|---|---|
| Present Example 19 | Compound 1 | GH1 | 4.21 | 131 | 129 | 125 |
| Present Example 20 | Compound 1 | GH2 | 4.20 | 132 | 130 | 127 |
| Present Example 21 | Compound 1 | GH3 | 4.22 | 130 | 128 | 125 |
| Present Example 22 | Compound 1 | GH4 | 4.23 | 131 | 128 | 126 |
| Present Example 23 | Compound 1 | GH5 | 4.22 | 129 | 127 | 124 |

Structures of GH1 to GH5 as host materials of Present Examples 19 to 23 of the Table 4 are as follows, and compound names thereof are described in the above Table 1.
GH1
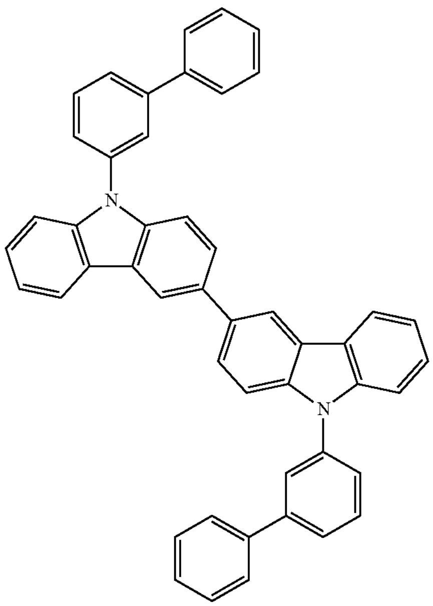
GH2
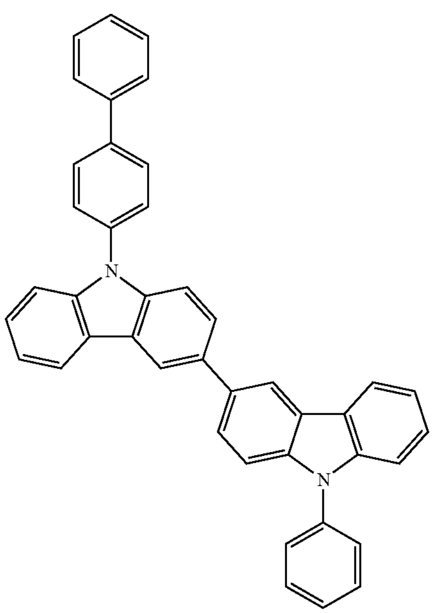
-continued
GH3
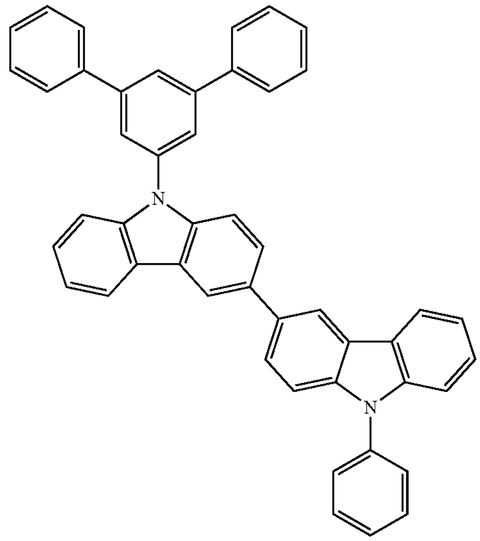
GH4
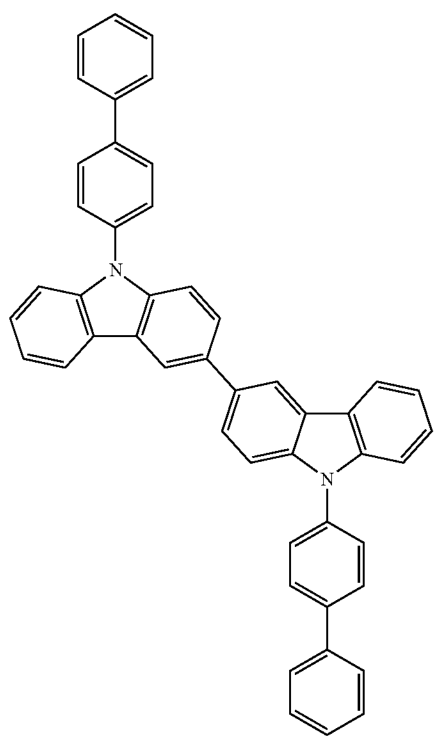

-continued

GH5

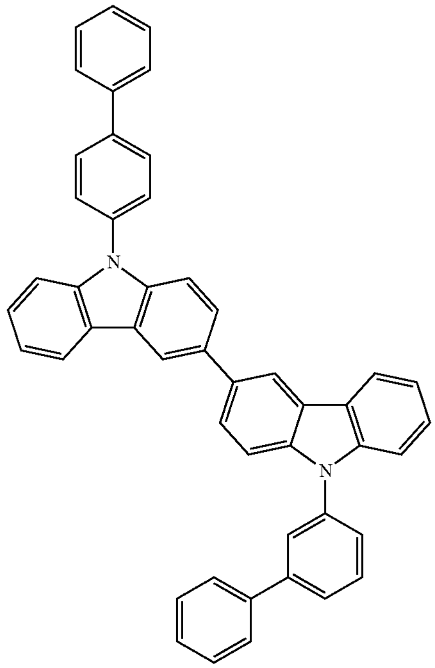 [SMILES: c1ccc(-c2ccc(-n3c4ccccc4c4cc(-c5ccc6c(c5)c5ccccc5n6-c5cccc(-c6ccccc6)c5)ccc43)cc2)cc1]

Present Examples 24 to 28

An organic light-emitting diode of each of Present Examples 24 to 28 was manufactured in the same manner as in Present Example 2 except that each of compounds shown in a following Table 5 was used instead of CBP as the host in Present Example 2. The structures of the host materials GH1 to GH5 are the same as those described above with reference to Present Examples 19 to 23.

TABLE 5

| Examples | Dopant | Host | Operation voltage (V) | Maximum Luminous Quantum Efficiency (%, relative value) | EQE (%, relative value) | LT95 (%, relative value) |
|---|---|---|---|---|---|---|
| Present Example 24 | Compound 2 | GH1 | 4.23 | 130 | 129 | 127 |
| Present Example 25 | Compound 2 | GH2 | 4.21 | 132 | 129 | 126 |
| Present Example 26 | Compound 2 | GH3 | 4.22 | 130 | 128 | 127 |
| Present Example 27 | Compound 2 | GH4 | 4.22 | 131 | 129 | 128 |
| Present Example 28 | Compound 2 | GH5 | 4.23 | 132 | 129 | 128 |

It may be identified from the results of the above Table 2 and Table 3 that in the organic light-emitting diode in which the organometallic compound of each of Present Examples 1 to 18 which satisfies the Chemical Formula 1 according to the present disclosure is used as the dopant of the light-emitting layer of the diode, the operation voltage of the diode is lowered, the maximum luminous quantum efficiency, external quantum efficiency (EQE) and lifetime (LT95) of the diode are improved, compared to those in each of Comparative Examples 1 to 10.

A scope of protection of the present disclosure should be construed by the scope of the claims, and all technical ideas within the scope equivalent thereto should be construed as being included in the scope of the present disclosure. Although the embodiments of the present disclosure have been described in more detail with reference to the accompanying drawings, the present disclosure is not necessarily limited to these embodiments. The present disclosure may be implemented in various modified manners within the scope not departing from the technical idea of the present disclosure. Accordingly, the embodiments disclosed in the present disclosure are not intended to limit the technical idea of the present disclosure, but to describe the present disclosure. the scope of the technical idea of the present disclosure is not limited by the embodiments. Therefore, it should be understood that the embodiments as described above are illustrative and non-limiting in all respects. The scope of protection of the present disclosure should be interpreted by the claims, and all technical ideas within the scope of the present disclosure should be interpreted as being included in the scope of the present disclosure.

What is claimed is:

1. An organometallic compound represented by one selected from the group consisting of following compounds:

107

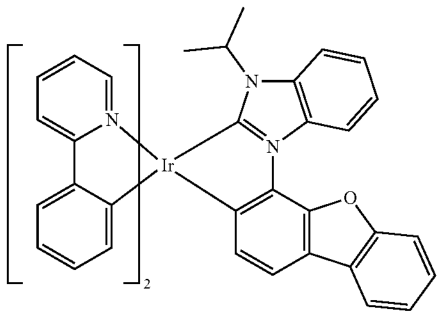

197

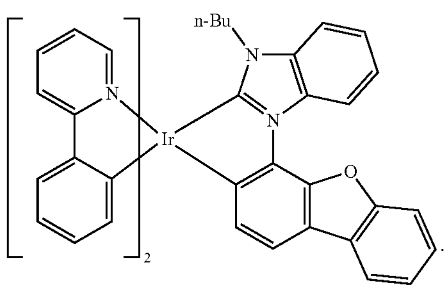

2. The organometallic compound of claim 1, wherein the compound is used as a green phosphorescent material.

3. An organic light-emitting diode comprising:

a first electrode;

a second electrode facing the first electrode; and an organic layer disposed between the first electrode and the second electrode;

wherein the organic layer includes a light-emitting layer, wherein the light-emitting layer contains the organometallic compound according to claim 1.

4. The organic light-emitting diode of claim 3, wherein the organometallic compound is used as dopant of the light-emitting layer.

5. The organic light-emitting diode of claim 3, wherein a host material of the light-emitting layer includes a compound containing a carbazole group.

6. The organic light-emitting diode of claim 5, wherein the compound containing the carbazole group includes at least one selected from compounds of following structures:

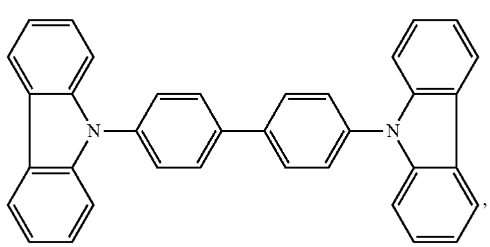

-continued

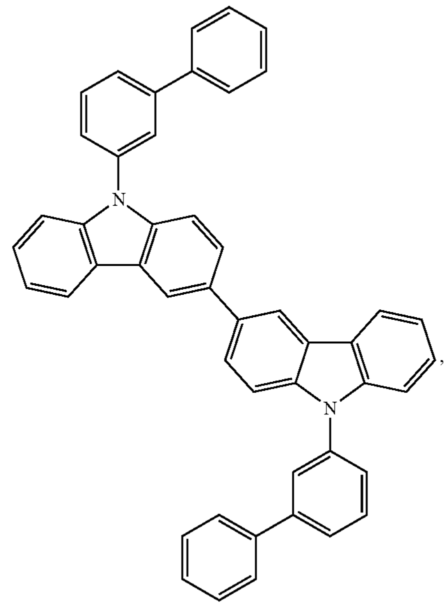

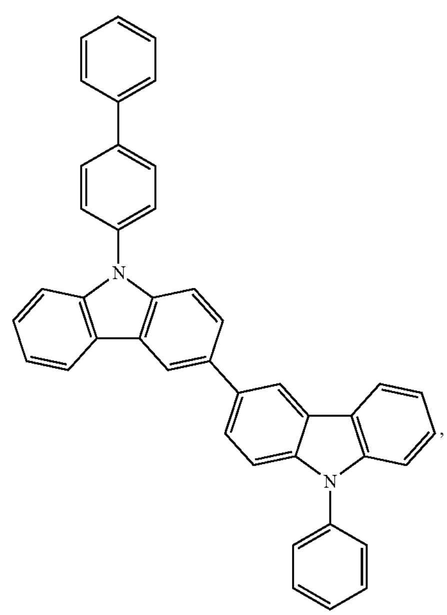

-continued

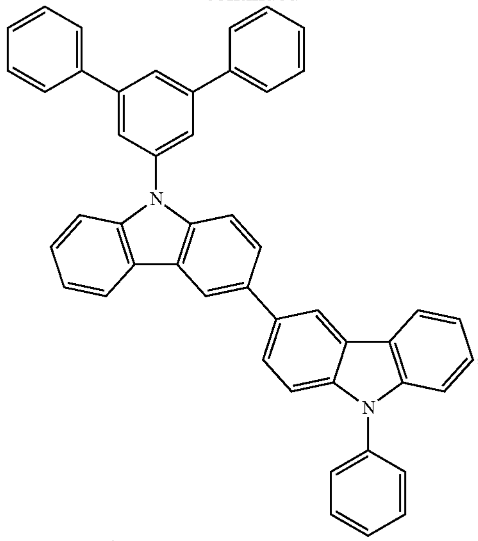

,

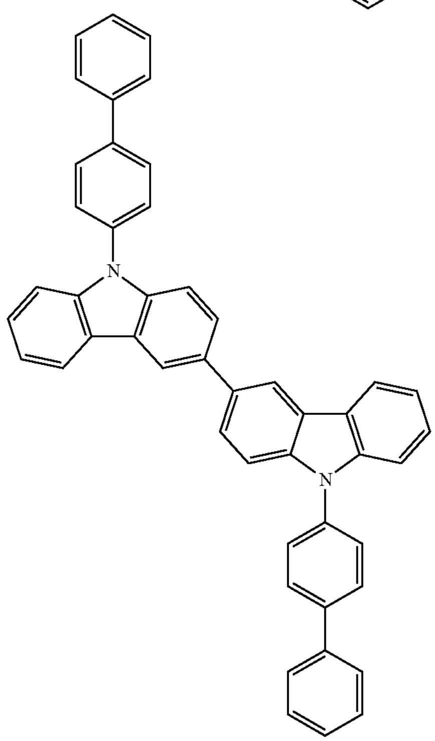

and

-continued

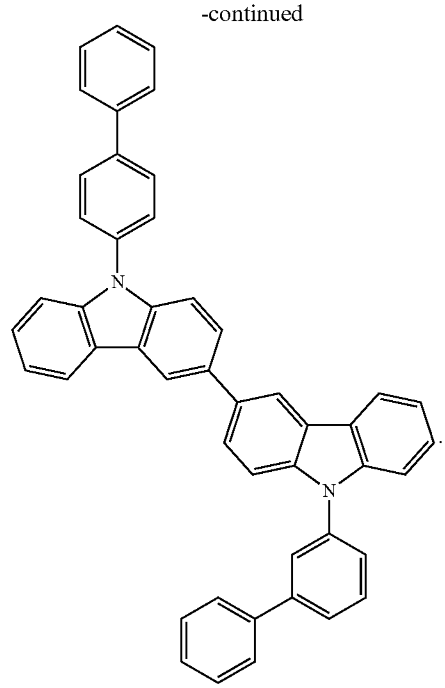

.

7. The organic light-emitting diode of claim 3, wherein the organic layer further includes at least one selected from a group consisting of a hole injection layer, a hole transport layer, an electron transport layer and an electron injection layer.

8. An organic light-emitting display device comprising:

a substrate;

a driving element positioned on the substrate; and an organic light-emitting element disposed on the substrate and connected to the driving element, wherein the organic light-emitting element includes the organic light-emitting diode according to claim 3.

* * * * *